US012103916B2

(12) United States Patent
Garneau-Tsodikova et al.

(10) Patent No.: US 12,103,916 B2
(45) Date of Patent: Oct. 1, 2024

(54) ANTIFUNGAL COMPOUNDS

(71) Applicant: University of Kentucky Research Foundation, Lexington, KY (US)

(72) Inventors: Sylvie Garneau-Tsodikova, Lexington, KY (US); Sanjib K Shrestha, Lexington, KY (US); Atefeh Garzan, Lexington, KY (US); Nishad Thamban Chandrika, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/836,675

(22) Filed: Dec. 8, 2017

(65) Prior Publication Data

US 2018/0194742 A1    Jul. 12, 2018

Related U.S. Application Data

(60) Provisional application No. 62/595,975, filed on Dec. 7, 2017, provisional application No. 62/431,679, filed on Dec. 8, 2016.

(51) Int. Cl.
| | |
|---|---|
| *C07D 249/08* | (2006.01) |
| *A01N 33/08* | (2006.01) |
| *A01N 43/60* | (2006.01) |
| *A01N 43/653* | (2006.01) |
| *A01N 43/84* | (2006.01) |
| *A01N 47/12* | (2006.01) |
| *A61P 31/10* | (2006.01) |
| *C07C 217/08* | (2006.01) |
| *C07C 271/16* | (2006.01) |
| *C07D 295/03* | (2006.01) |
| *C07D 403/06* | (2006.01) |
| *C07D 405/06* | (2006.01) |

(52) U.S. Cl.
CPC .......... *C07D 249/08* (2013.01); *A01N 33/08* (2013.01); *A01N 43/60* (2013.01); *A01N 43/653* (2013.01); *A01N 43/84* (2013.01); *A01N 47/12* (2013.01); *A61P 31/10* (2018.01); *C07C 217/08* (2013.01); *C07C 271/16* (2013.01); *C07D 295/03* (2013.01); *C07D 403/06* (2013.01); *C07D 405/06* (2013.01)

(58) Field of Classification Search
None
See application file for complete search history.

(56) References Cited

U.S. PATENT DOCUMENTS 4,927,839 A * 5/1990 Parry ............... A01N 43/64
514/383

FOREIGN PATENT DOCUMENTS

WO    WO0189447    * 11/2001

OTHER PUBLICATIONS

Aher et al., Synthesis and antifungal activity of 1,2,3-triazole containing fluconazole analogues. Bioorganic & Medicinal Chemistry Letters, 2009, 19, 759-763 (including supporting information).*
Hof, H. Critical Annotations to the Use of Azole Antifungals for Plant Protection. Antimicrobial Agents and Chemotherapy, 2001, 45, 2987-2990.*
Chemical Abstract Registry No. 149764-64-7, indexed in the Registry File on STN CAS Online Sep. 3, 1993.*
Chemical Abstract Registry No. 149764-62-5, indexed in the Registry File on STN CAS Online Sep. 3, 1993.*
Chemical Abstract Registry No. 54722-41-7, indexed in the Registry File on STN CAS Online Nov. 16, 1984.*
Chemical Abstract Registry No. 1430461-35-0, indexed in the Registry File on STN CAS Online May 8, 2013.*
Chemical Abstract Registry No. 132507-80-3, indexed in the Registry File on STN CAS Online Mar. 8, 1991.*
Chemical Abstract Registry No. 58905-16-1, indexed in the Registry File on STN CAS Cas Online Nov. 16, 1984.*
Chemical Abstract Registry No. 1342247-91-9, indexed in the Registry File on STN CAS Online Nov. 7, 2011.*
Ito et al., A medium-term rat liver bioassay for rapid in vivo detection of carcinogenic potential of chemicals. Cancer Science, 2003, 94, 3-8.*
Chemical Abstract Registry No. 63207-03-4, indexed in the Registry File on STN CAS Online Nov. 16, 1984.*
Chemical Abstract Registry No. 75937-12-1, indexed in the Registry File on STN CAS Online Nov. 16, 1984.*
Chemical Abstract Registry No. 84595-27-7, indexed in the Registry File on STN CAS Online Nov. 16, 1984.*
Chemical Abstract Registry No. 118227-30-8, indexed in the Registry File on STN CAS Online Dec. 30, 1988.*
Chemical Abstract Registry No. 86386-76-7 , indexed in the Registry File on STN CAS Online Nov. 16, 1984.*
Chemical Abstract Registry No. 54256-45-0, indexed in the Registry File on STN CAS Online Nov. 16, 1984.*
Chemical Abstract Registry No. 81886-66-0, indexed in the Registry File on STN CAS Online Nov. 16, 1984.*
Sheehan et al., Current and Emerging Azole Antifungal Agents. Clinical Microbiology Reviews, 1999, 12, 40-79.*
Sun et al., Synthesis and antifungal activity of triazole derivative. Chinese Journal of Medicinal Chemistry, 2004, 14, 14-18.*
CAPLUS printout of "Sun et al., Synthesis and antifungal activity of triazole derivative. Chinese Journal of Medicinal Chemistry, 2004, 14, 14-18."*
Chemical Abstract Registry No. 25727-93-9, indexed in the Regstry File on STN CAS Online Nov. 16, 1984.*
Zhang et al., Structure-Based Rational Screening of Novel Hit Compounds with Structural Diversity for Cytochrome P450 Sterol 14α-Demethylase from Penicillium digitatum. Journal of Chemical Information and Modeling, 2010, 50, 317-325.*

(Continued)

*Primary Examiner* — Po-Chih Chen
(74) *Attorney, Agent, or Firm* — Stites & Harbison PLLC; Mandy Wilson Decker

(57) ABSTRACT

Compounds and compositions having antifungal activity, and methods of using the antifungal compounds and compositions, are described for use in treating fungal infections.

7 Claims, 23 Drawing Sheets

(56) References Cited

OTHER PUBLICATIONS

Caplus printout of "Zhang et al., Synthesis and antifungal activity of triazolylpropanol derivatives. Zhejiang Yike Daxue Xuebao, 1992, 21, 251-255."*

Zhang et al., Synthesis and antifungal activity of triazolylpropanol derivatives. Zhejiang Yike Daxue Xuebao, 1992, 21, 251-255.*

Shrestha et al., Novel alkylated azoles as potent antifungals. European Journal of Medicinal Chemistry, 2017, 133, 309-318 and its supporting information.*

Tang et al., Synthesis and biological evaluation of novel triazole derivatives as antifungal agents. Chinese Chemical Letters, 2013, 24, 219-222.*

Caplus printout of "Tang et al., Synthesis and biological evaluation of novel triazole derivatives as antifungal agents. Chinese Chemical Letters, 2013, 24, 219-222."*

Zhou et al., Synthesis and antifungal activity of 2-(2,4-difluorophenyl)-1-(4-alkylpiperazine-1-yl)-3-(1,2,4-triazole-1-yl)-2-propanol. Huaxue Yanjiu Yu Yingyong, 2003, 15, 521-523.*

Baltzly, R., Unsymmetrically N-Substituted Piperazines. IV. N-Alkyl Derivatives. Journal of the American CHemical Society, 1954, 76, 1164-1165.*

Caplus printout of "Baltzly, R., Unsymmetrically N-Substituted Piperazines. IV. N-Alkyl Derivatives. Journal of the American CHemical Society, 1954, 76, 1164-1165."*

Shrestha, S. K.; Garzan, A.; Garneau-Tsodikova, S.; Novel alkylated azoles as potent antifungals. Eur. J. Med. Chem. 2017, 133, 309-318.

Shrestha, S. K.; Garzan, A.; Garneau-Tsodikova, S.; Supporting Information for Novel alkylated azoles as potent antifungals, pp. S1-S81.

Chandrika, et al., Novel fluconazole derivatives with promising antifungal activity, Bioorganic & Medicinal Chemistry 26 (2018) 573-580.

Chandrika, et al., Supporting Information for Novel fluconazole derivatives with promising antifungal activity, pp. S1-S32.

Chandrika, et al., Alkylated Piperazines and Piperazine-Azole Hybrids as Antifungal Agents, J. Med. Chem. 2018, 61, 158-173.

Chandrika, et al., Supporting Information for Alkylated Piperazines and Piperazine-Azole Hybrids as Antifungal Agents, pp. S1-S31.

* cited by examiner

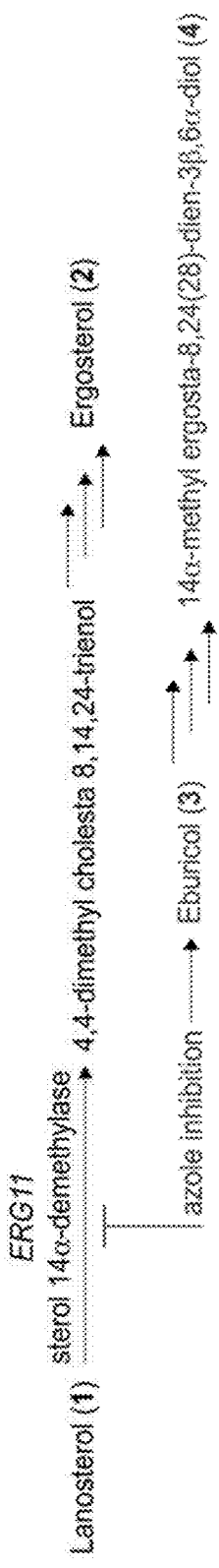
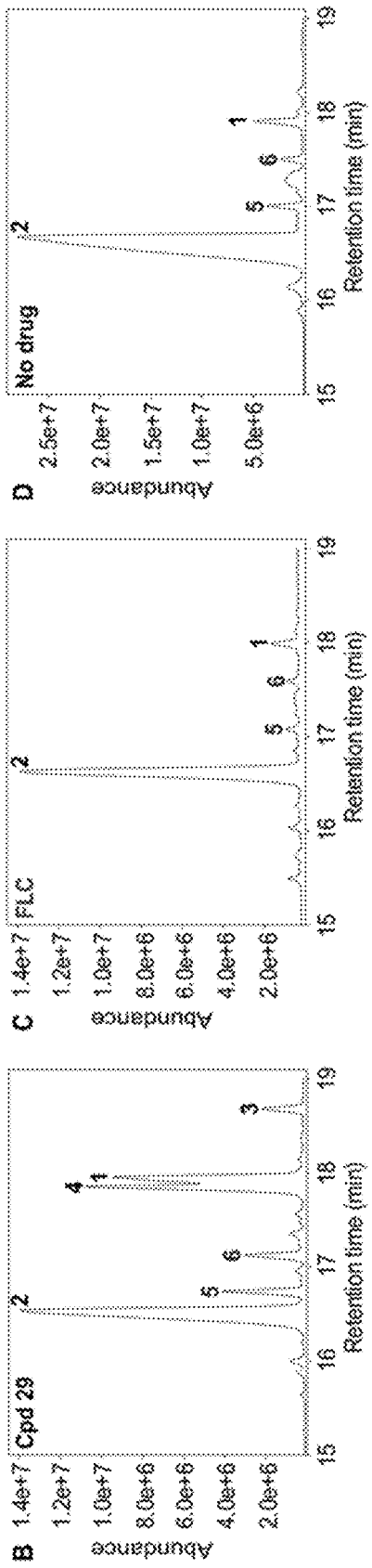
FIG. 7A
FIG. 7B
FIG. 7C
FIG. 7D

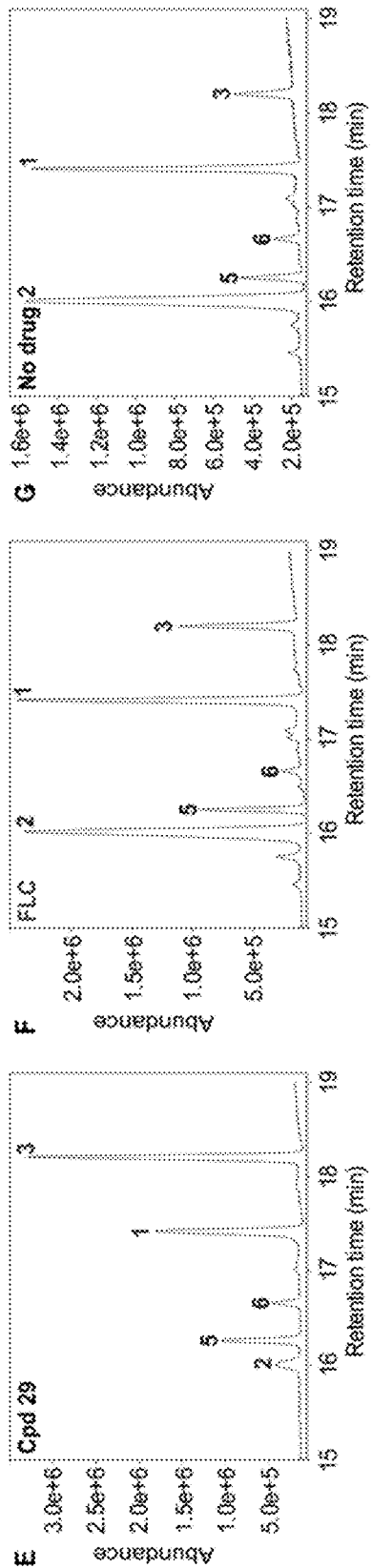

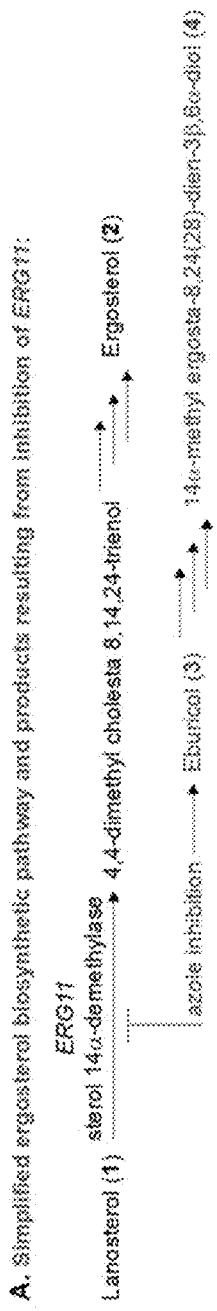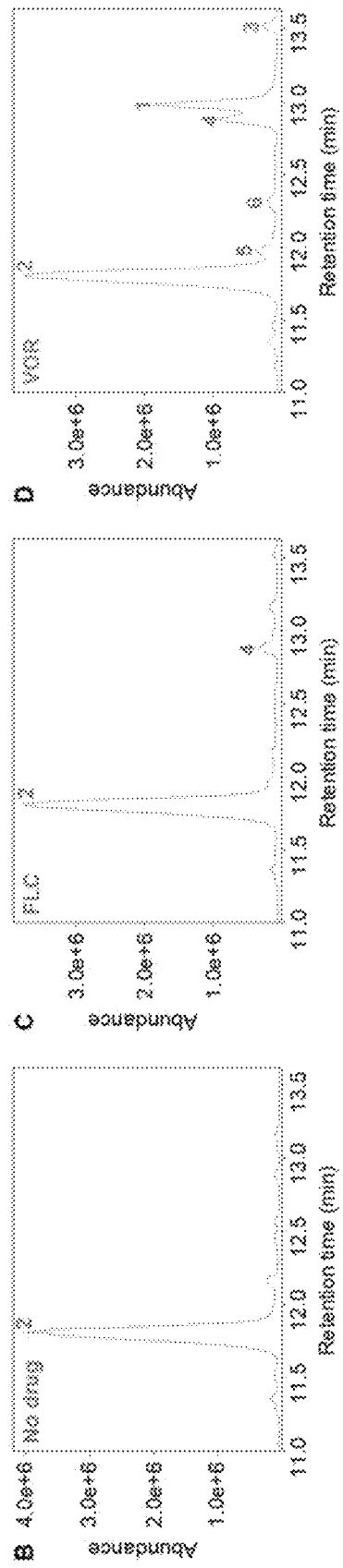
FIG. 13A
FIG. 13B
FIG. 13C
FIG. 13D

G. Sterol composition of untreated and FLC-, VOR-, cpd 20-, and cpd 26-treated C. albicans ATCC 10231:

| Sterol | Sterol composition (%) | | | | |
|---|---|---|---|---|---|
| | No drug | FLC | VOR | Cpd 20 | Cpd 26 |
| Lanosterol (1) | ND | ND | 18.49 | 33.37 | 29.49 |
| Ergosterol (2) | 100.00 | 95.90 | 64.93 | 30.15 | 50.64 |
| Eburicol (3) | ND | ND | 2.14 | 1.25 | 1.15 |
| 14α-methyl ergosta-8,24(28)-dien-3β,6α-diol (4) | ND | 4.10 | 10.05 | 15.40 | 11.05 |
| Unknown sterol (5) | ND | ND | 2.79 | 14.42 | 3.56 |
| Unknown sterol (6) | ND | ND | 1.56 | 2.80 | 4.08 |
| Unknown sterol (7) | ND | ND | ND | 2.55 | ND |

ND = not detected

ANTIFUNGAL COMPOUNDS

RELATED APPLICATIONS

This application claims priority from U.S. Provisional Application Ser. No. 62/595,975 filed Dec. 7, 2017, and 62/431,679 filed Dec. 8, 2016, the entire disclosure of which is incorporated herein by this reference.

TECHNICAL FIELD

The presently-disclosed subject matter generally relates to compounds and compositions having antifungal activity, and methods of using the antifungal compounds and compositions, including use for treating fungal infections.

INTRODUCTION

Fungal infections have been rapidly increasing worldwide and present a continuous threat to human health.[1] Drug resistance among fungal pathogens is an increasing problem, thus identification and development of compounds capable of overcoming resistance is a requisite.[2] The conventional antifungal agents used in the treatment of human fungal infections are azoles (e.g., fluconazole (FLC), voriconazole (VOR), itraconazole (ITC), and posaconazoe (POS)), polyenes (e.g., amphotericin B (AmB)) (FIG. 1), echinocandins (e.g., anidulafungin, caspofungin and micafungin), and allylamines (e.g., terbinafine and naftifine) (FIG. 1).[3]

The present inventors previously showed that kanamycin B (KANB) and tobramycin (TOB) analogues with linear alkyl chains comprising 12 and 14 carbons ($C_{12}$ and $C_{14}$; FIG. 1) display promising antifungal potency against *Candida albicans* and *Aspergillus* spp.[4, 5] Unlike the parent aminoglycoside antibiotics, the $C_{12}$ and $C_{14}$ KANB and TOB analogues appear to inhibit fungi by disrupting the fungal membrane as a novel mechanism of action. Similarly, the present inventors recently demonstrated that n-alkylated ebsulfur derivatives, especially that containing a $C_5$ alkyl chain, display strong antifungal activities, albeit without disrupting the fungal membrane.[6, 7]

Currently, azoles have been used with considerable success in the treatment of serious fungal infections due to their high therapeutic index, their favorable pharmacokinetic (PK) parameters, excellent activity against *Candida* spp., and good safety profile.[3] One of the most important members of the azoles family is FLC, which was one of the first azole drugs to contain a quaternary center comprising an hydroxyl moiety.[8] FLC has been widely applied clinically. However, it is not effective against invasive aspergillosis and the number of FLC-resistant strains has augmented significantly with the increased use of this antifungal agent.[9, 10]

ITC, one of the other azoles, shows stronger activity against *Aspergillus* spp. than does FLC, but has poor aqueous solubility and oral bioavailability.[11] Many novel azoles have been developed to overcome these disadvantages, including second-generation azoles such as VOR, POS, ravuconazole, isavuconazole, and albaconazole, which demonstrate favorable antifungal activities, improved PK properties, and acceptable toxicity profiles.[12] Some of these newer azole derivatives (e.g., VOR, POS, ITC, ravuconazole, isavuconaozle) were generated by replacing one of the triazole rings of FLC by other moieties.

An azole drug, hexaconazole (labeled compound 27 in FIG. 2 of this study) comprising a $C_4$ alkyl chain in its structure, is FDA-approved as an antifungal agent.[13, 14] Some types of fungal infections such as pulmonary infections with *Aspergillus* can cause swallowing difficulties, so there is a pressing medical need for injectable antifungal agents.[15]

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Herein, inspired by the clinical applicability of azoles, the use of hexaconazole as a fungicidal agent, and the promise of the $C_{12}$ and $C_{14}$ KANB and TOB analogues and $C_5$ ebsulfur derivative, the present inventors prepared a series of unique compounds. The compounds were tested for antifungal activity against a number of fungal strains including 3 non-albican *Candida* strains, 3 *Aspergillus* strains, as well as multiple *Candida albicans* strains. The majority of strains tested exhibited susceptibility to these compounds.

The compounds were also subjected to time kill assays against strains of *Candida albicans*, the results of which demonstrated dose-dependent killing and fungistatic effects. Notably, superior growth inhibition was reported for the compounds compared to the reference drug VOR.

The compounds were examined for potential hemolytic effect in determining relative safety profiles. The compounds displayed less hemolysis than the FDA-approved drug, AmB, used as a control. The compounds have also been shown to be non-toxic in mammalian cells, with a better safety profile than the FDA-approved drug, AmB. Separate from efficacy and safety studies, the potential mechanism of action of the compounds was investigated and it was determined that they do not disrupt the fungal membrane and therefore have a different mode of antifungal activity.

The presently-disclosed subject matter includes antifungal compounds. The presently-disclosed subject matter further includes a pharmaceutical composition that includes the antifungal compounds and a suitable pharmaceutical carrier.

The presently-disclosed subject matter further includes a method of treating a fungal infection, which involves administering an effective amount of a compound or composition as disclosed herein. In some embodiments, the method involves administering the compound or composition to a subject. In some embodiments, the subject is a human subject. In some embodiments, the method involves administering the compound or composition to a plant or crop.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 7A-FIG. 7H includes FIG. 7A. A simplified ergosterol biosynthetic pathway and products resulting from inhibition of ERG11. FIG. 7B-G. include GC-MS chromatograms of the sterols extracted from untreated and antifungals treated C. albicans strains. C. albicans ATCC 10231 (strain A) was treated with FIG. 7B compound 29 and FIG. 7C FLC at 0.125 ug/mL, or FIG. 7B DMSO (no drug) as a control. Likewise, C. albicans ATCC 64124 (strain B) was treated with FIG. 7E compound 29 and FIG. 7F FLC at 1.95 ug/mL, or FIG. 7G DMSO (no drug) as a control. The peaks are for lanosterol (1), ergosterol (2), eburicol (3), 14-alpha-methyl ergosta 8,24(28)-dien-3-beta,6-alpha-diol (4), and unknown sterols (5 and 6). FIG. 7H is a table summarizing the percentage of each sterol from panels B-G.

FIG. 11A. HEK-293, FIG. 11B. A549, and FIG. 11C. BEAS-2B. Cells were treated with various concentrations of compounds 7 (yellow bars), 9 (orange bars), 18 (green bars), 20 (turquoise bars), 22 (blue bars), 25 (purple bars), 26 (hot pink bars), and VOR (light pink bars). The positive control consisted of cells treated with Triton X-100® (TX, 12.5% v/v). The negative control consisted of cells treated with DMSO (no drug).

FIG. 13A. A simplified ergosterol biosynthetic pathway and products resulting from inhibition of ERG11. FIG. 13B-FIG. 13F. GC-MS chromatograms of the sterols extracted from untreated and antifungal-treated C. albicans ATCC 10231 (strain A). The fungal strain was treated with FIG. 13B DMSO (no drug control, panel B), FIG. 13C FLC at 1.95 μg/mL (panel C), FIG. 13D VOR at 0.12 μg/mL (panel D), FIG. 13E compound 20 at 0.48 μg/mL (panel E), and FIG. 13F compound 26 at 0.975 μg/mL (panel F). The peaks in these chromatograms are for lanosterol (1), ergosterol (2), eburicol (3), 14α-methyl ergosta-8,24(28)-dien-3β, 6α-diol (4), and three unknown sterols (5-7). FIG. 13G includes a table summarizing the percentage of each sterol from panels B-F.

Figures 19A, 19B, 19C:
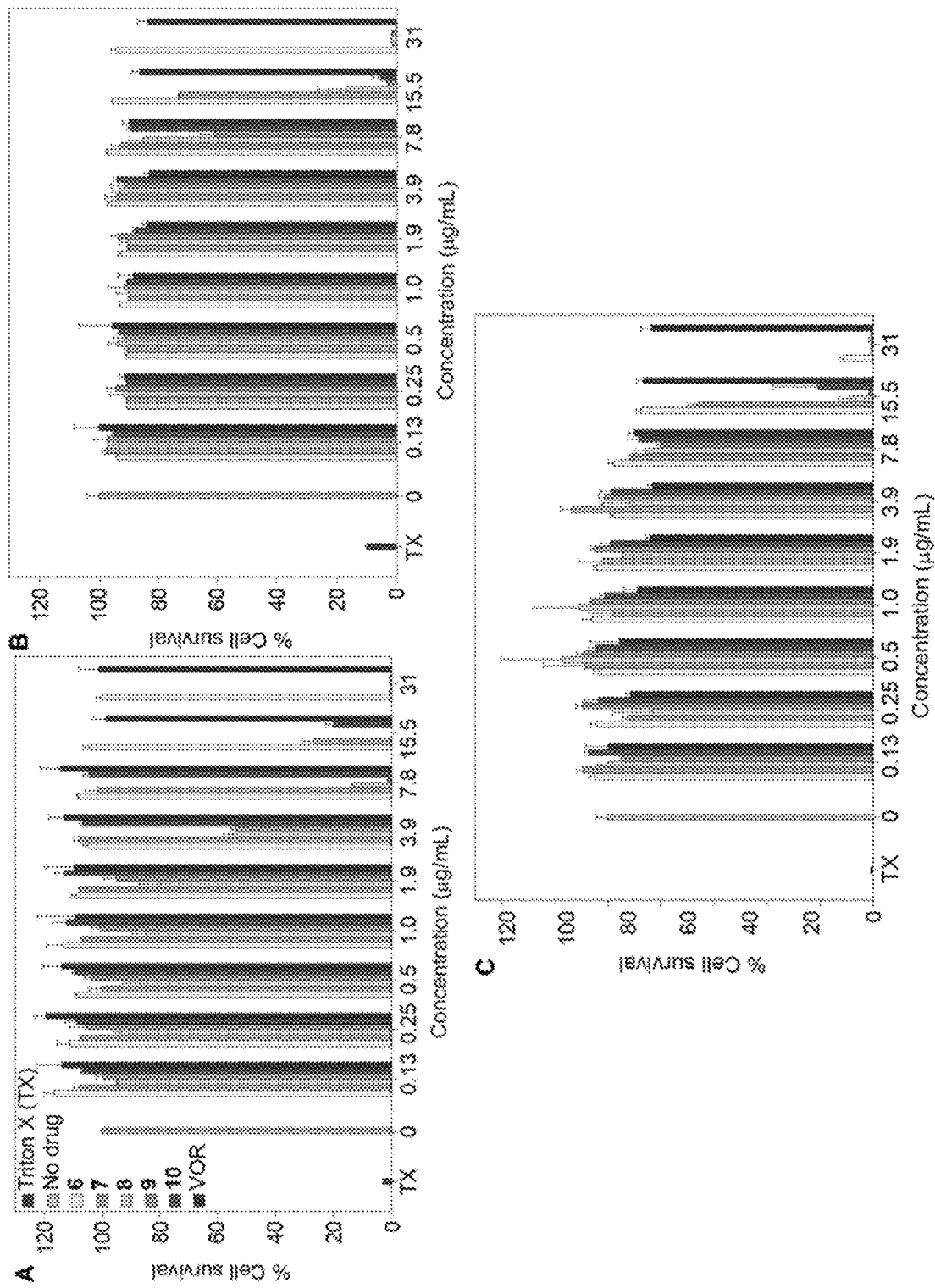
FIG. 19A-19C includes representative cytotoxicity assays of compounds 6-10 against three mammalian cell lines: FIG.

19A. HEK-293, FIG. 19B. BEAS-2B, and FIG. 19C. A549. Cells were treated with various concentrations of compounds 6 (yellow), 7 (orange), 8 (turquoise), 9 (blue), 10 (pink), and VOR (purple). The positive control consisted of cells treated with Triton X-100® (TX, 20% v/v, pink). The negative control consisted of cells treated with DMSO (no drug, green). The experiments were performed in duplicate.

Figure 20:
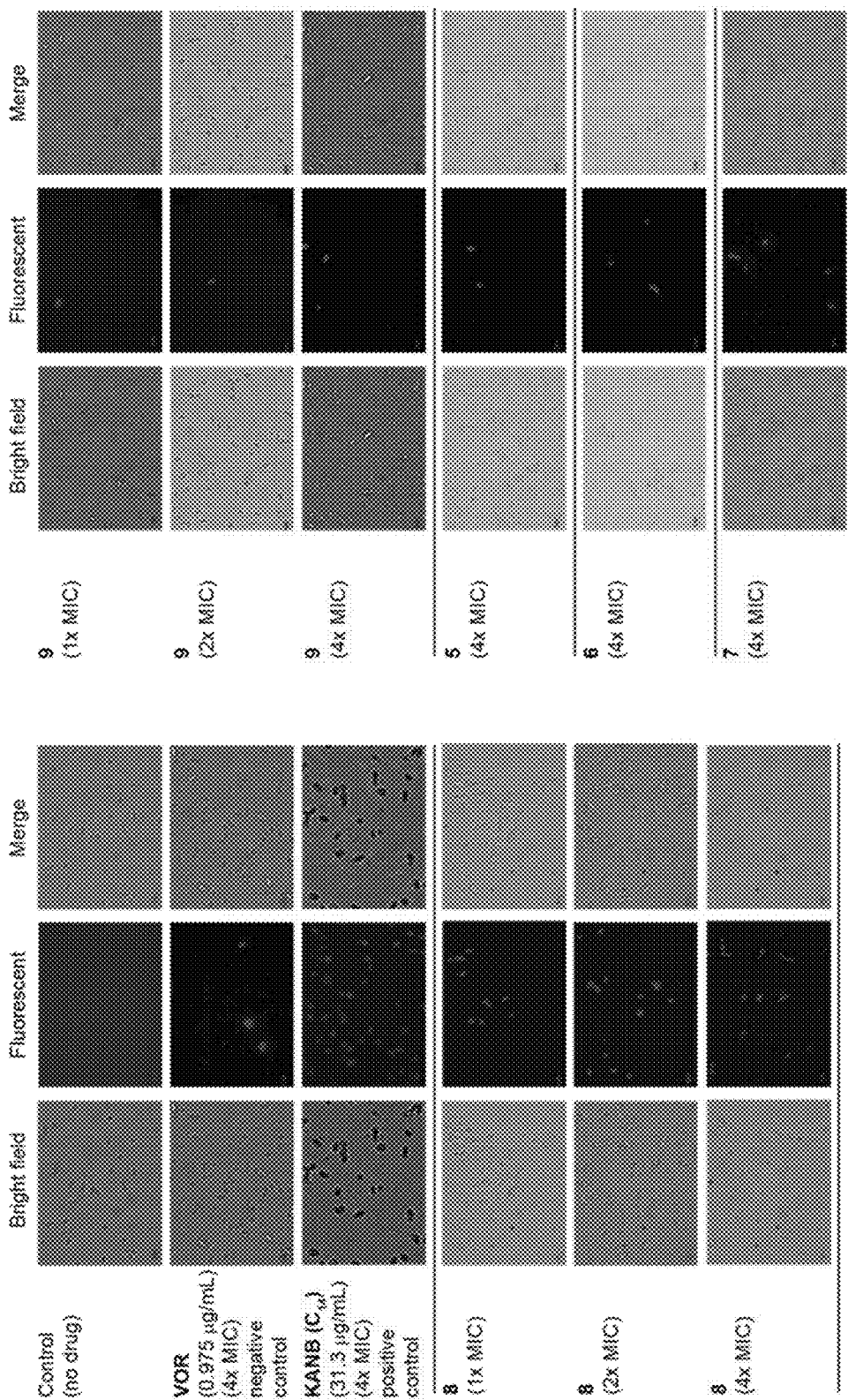

FIG. 20 includes the Effect of the controls VOR (negative) and KANB ($C_{14}$) (positive) as well as compounds 5-9 on the cell membrane integrity of *C. albicans* ATCC 10231 (strain A). For the three columns on the left from top to bottom: Propidium iodide (PI) dye uptake by yeast cells without drug, with VOR (0.975 μg/mL), KANB ($C_{14}$) (31.3 μg/mL), and compound 8 (1×, 2×, and 4×MIC). For the three columns on the right from top to bottom: Propidium iodide (PI) dye uptake by yeast cells with compound 9 (1×, 2×, and 4×MIC), as well as compound 5, 6, and 7 at 4×MIC. The experiments were performed in duplicate.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds having antifungal activity.

The terms "fungus" or "fungi" include a variety of nucleated, sporebearing organisms which are devoid of chlorophyll. Examples include yeasts, mildews, molds, rusts, and mushrooms. Examples of fungi include, but are not limited to *Aspergillus fumigatus, Aspergillus flavus, Aspergillus nidulans, Candida albicans, Candida glabrata, Candida guilliermondii, Candida krusei, Candida lusitaniae, Candida parapsilosis, Candida tropicalis, Cryptococcus neoformans, Issatchenkia orientalis, Coccidioides, Paracoccidioides, Histoplasma, Blastomyces*, and *Neurospora crassa*.

The term "antifungal agent" includes agents having fungistatic or fungicidal activity.

The term "antifungal activity" includes inhibiting the growth of a fungus (e.g., fungistatic activity), killing at least a portion of the fungus (e.g., fungicidal activity), and/or limiting the ability of the fungus to reproduce.

The term "inhibiting the growth of a fungus" includes both fungistatic and fungicidal activity. Fungistatic activity includes any decrease in the rate of growth of a fungal colony. Fungistatic activity may be manifested by a fungus maintaining its present size or failing to colonize the surrounding areas. Fungistatic activity may be a result of inhibition of the fungal reproductive processes. Fungicidal activity generally includes, for example, irradication of a fungus or fungal colony, killing a fungus or fungal colony or, in one embodiment, a decrease in the mass or size of a fungus or fungal colony.

In some embodiments, the compound is:

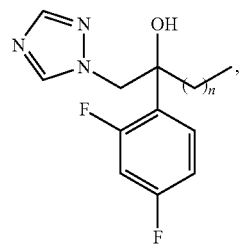

wherein n is 0-11, or

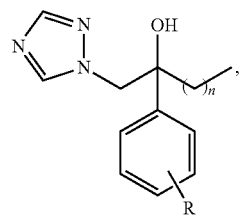

wherein n is 0-5, and R is 2,4-di-Cl, 2-F, 3-F, 4-F, 2-Cl, 3-Cl, or 4-Cl.

In some embodiments, the compound is selected from:

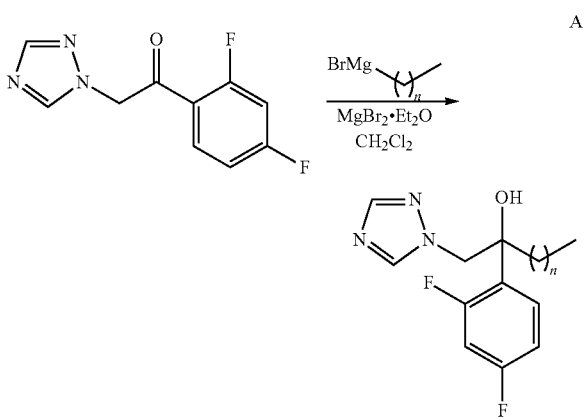

1: n = 0 (33%) 6: n = 5 (12%)
2: n = 1 (23%) 7: n = 7 (18%)
3: n = 2 (29%) 8: n = 9 (20%)
4: n = 3 (19%) 9: n = 11 (29%)
5: n = 4 (16%)

-continued
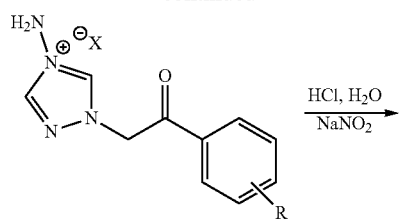
10: X = C, R = 2,4-di-Cl (94%)
11: X = Br, R = 2-F (96%)
12: X = Br, R = 3-F (90%)
13: X = Br, R = 4-F (88%)
14: X = Br, R = 2-Cl (90%)
15: X = Br, R = 3-Cl (96%)
16: X = Br, R = 4-Cl (91%)
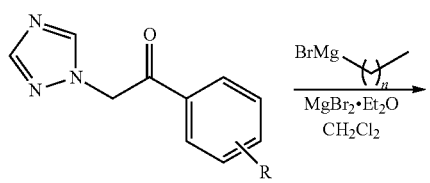
17: R = 2,4-di-Cl (75%)
18: R = 2-F (79%)
19: R = 3-F (63%)
20: R = 4-F (60%)
21: R = 2-Cl (25%)
22: R = 3-Cl (59%)
23: R = 4-Cl (72%)
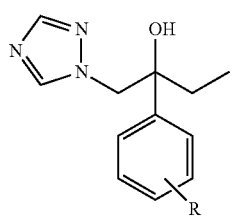
24: n = 0, R = 2,4-di-Cl (54%)
25: n = 1, R = 2,4-di-Cl (62%)
26: n = 2, R = 2,4-di-Cl (28%)
27: n = 3, R = 2,4-di-Cl (12%)
28: n = 4, R = 2,4-di-Cl (11%)
29: n = 5, R = 2-4-di-Cl (22%)
30: n = 4, R = 2-F (33%)
31: n = 5, R = 2-F (40%)
32: n = 4, R = 3-F (14%)
33: n = 5, R = 3-F (48%)
34: n = 4, R = 4-F (43%)
35: n = 5, R = 4-F (50%)
36: n = 4, R = 2-Cl (45%)
37: n = 5, R = 2-Cl (31%)
38: n = 4, R = 3-Cl (47%)
39: n = 5, R = 3-Cl (47%)
40: n = 4, R = 4-Cl (49%)
41: n = 5, R = 4-Cl (23%)
In some embodiments, the compound is selected from:
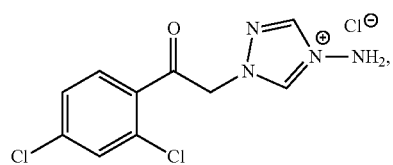
-continued
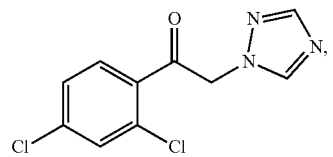
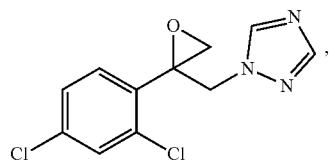
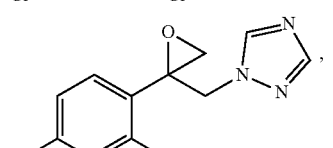
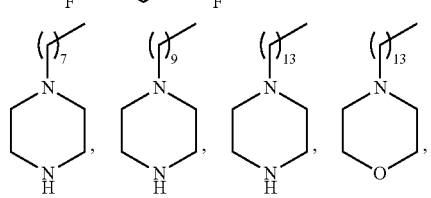
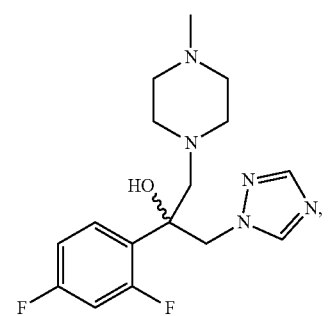
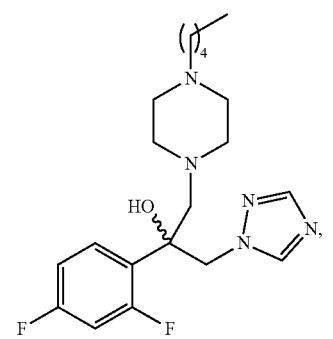
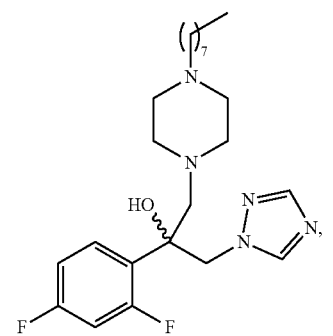

9
-continued
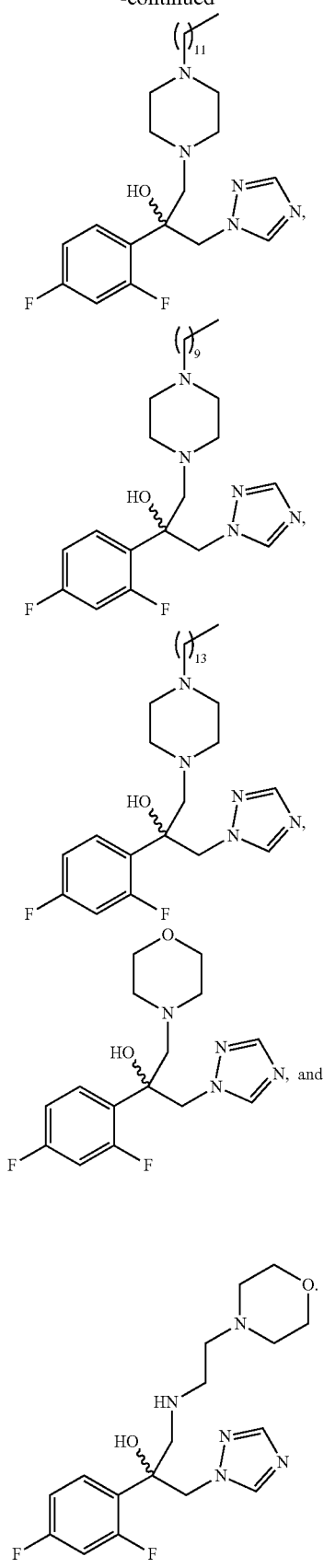
10
In some embodiments, the compound is selected from:
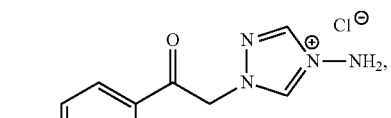
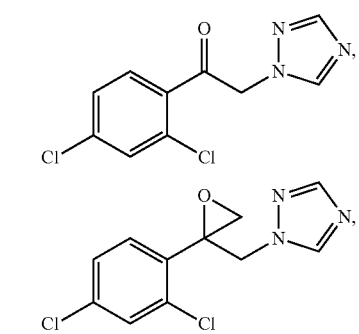
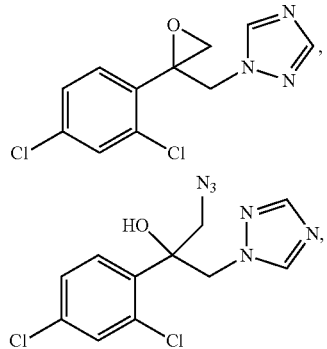
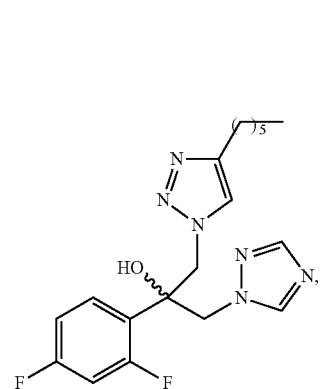
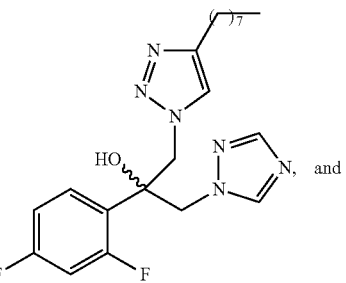

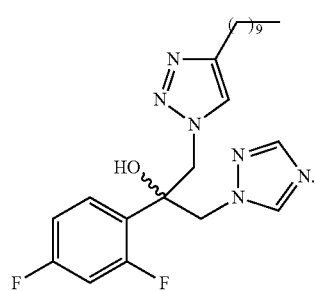
In some embodiments, the compound is selected from:
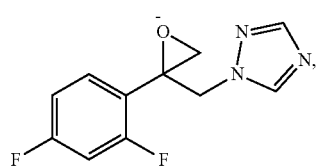
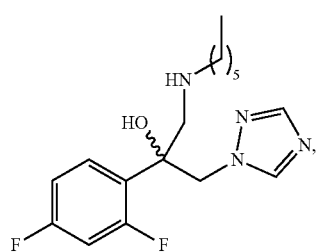
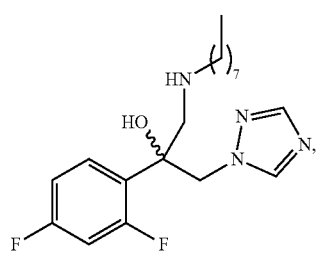
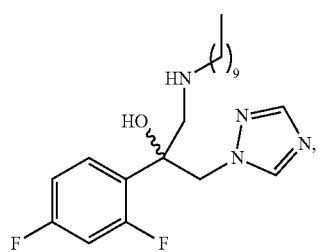
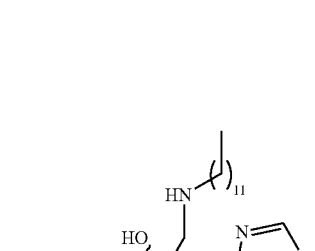
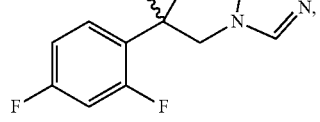
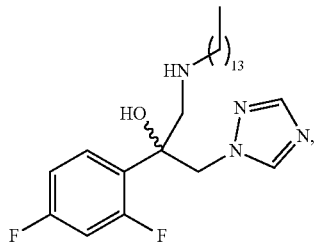
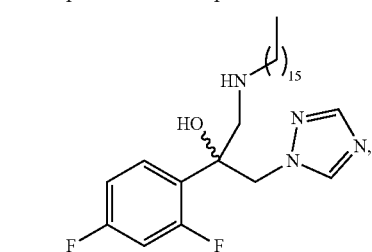
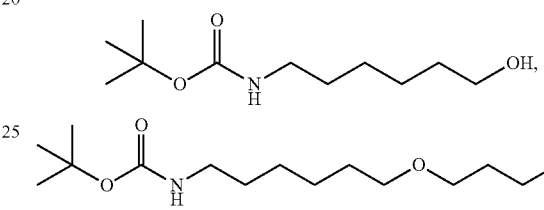
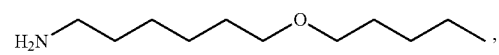
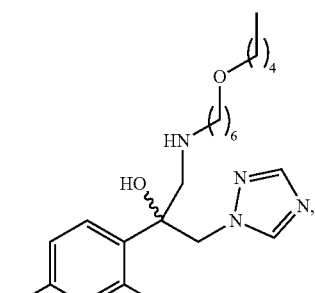
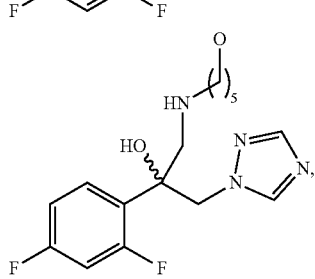
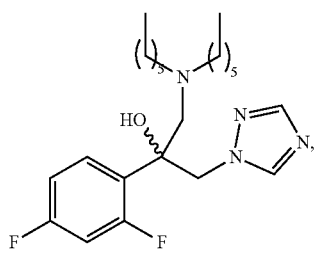

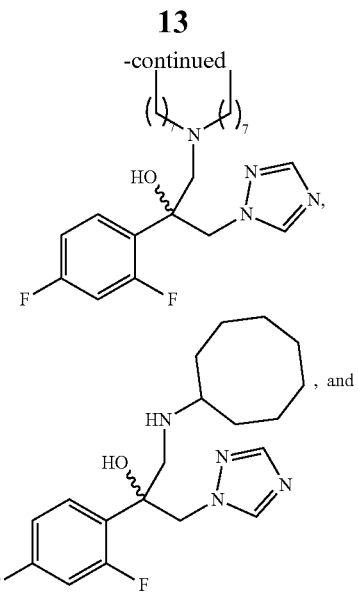
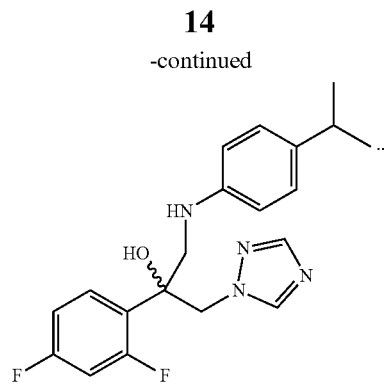
In some embodiments, the compound is selected from:
A
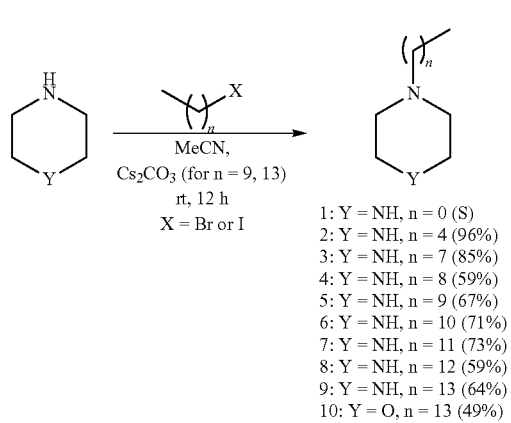
1: Y = NH, n = 0 (S)
2: Y = NH, n = 4 (96%)
3: Y = NH, n = 7 (85%)
4: Y = NH, n = 8 (59%)
5: Y = NH, n = 9 (67%)
6: Y = NH, n = 10 (71%)
7: Y = NH, n = 11 (73%)
8: Y = NH, n = 12 (59%)
9: Y = NH, n = 13 (64%)
10: Y = O, n = 13 (49%)
B
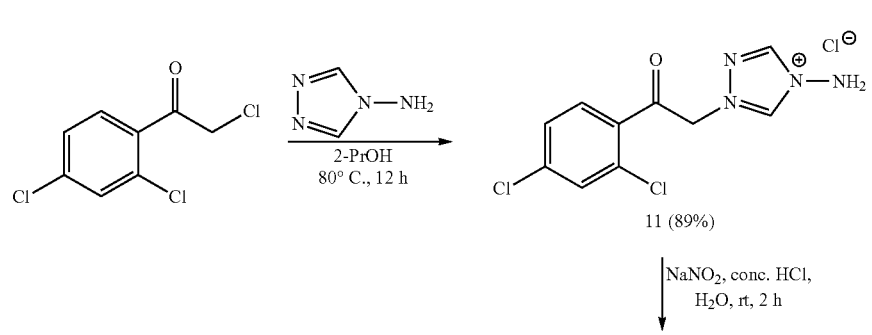

-continued
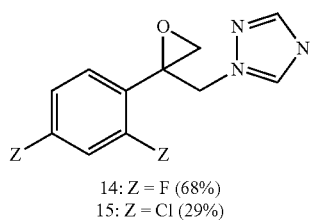
14: Z = F (68%)
15: Z = Cl (29%)
trimethylsulfoxonium iodide, cetyl bromide, NaOH, toluene, 60° C., 2 h
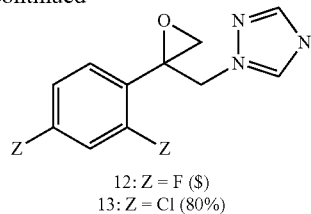
12: Z = F ($)
13: Z = Cl (80%)
morpholine, EtOH, Et₃N, 80° C., 12 h
or
4-(2-aminoethyl)morpholine, EtOH, Et₃N, 80° C., 12 h
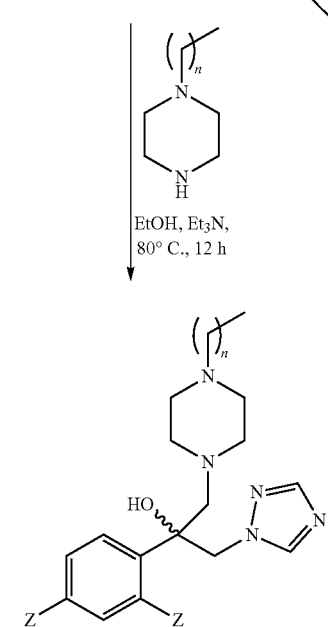
EtOH, Et₃N, 80° C., 12 h
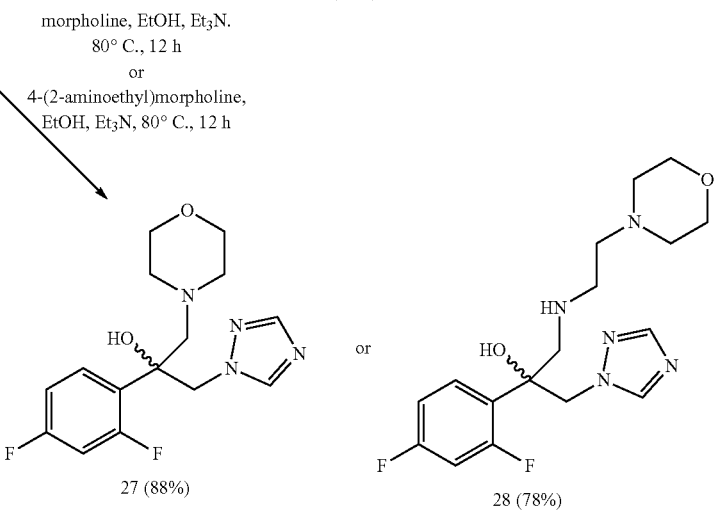
27 (88%)    28 (78%)
16: Z = F, n = 0 (77%)
17: Z = F, n = 4 (71%)
18: Z = F, n = 7 (53%)
19: Z = F, n = 8 (78%)
20: Z = F, n = 9 (73%)
21: Z = F, n = 10 (73%)
22: Z = F, n = 11 (80%)
23: Z = F, n = 12 (62%)
24: Z = F, n = 13 (83%)
25: Z = Cl, n = 9 (52%)
26: Z = Cl, n = 11 (45%)
In some embodiments, the compound is selected from:
A
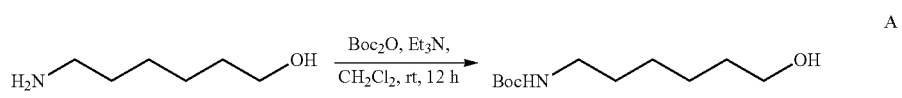
1: (79%)
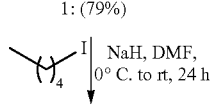
NaH, DMF, 0° C. to rt, 24 h
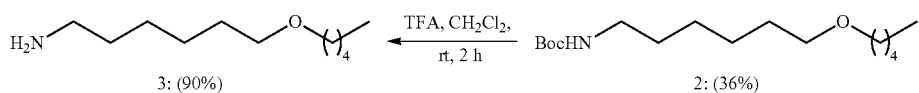
3: (90%)    2: (36%)

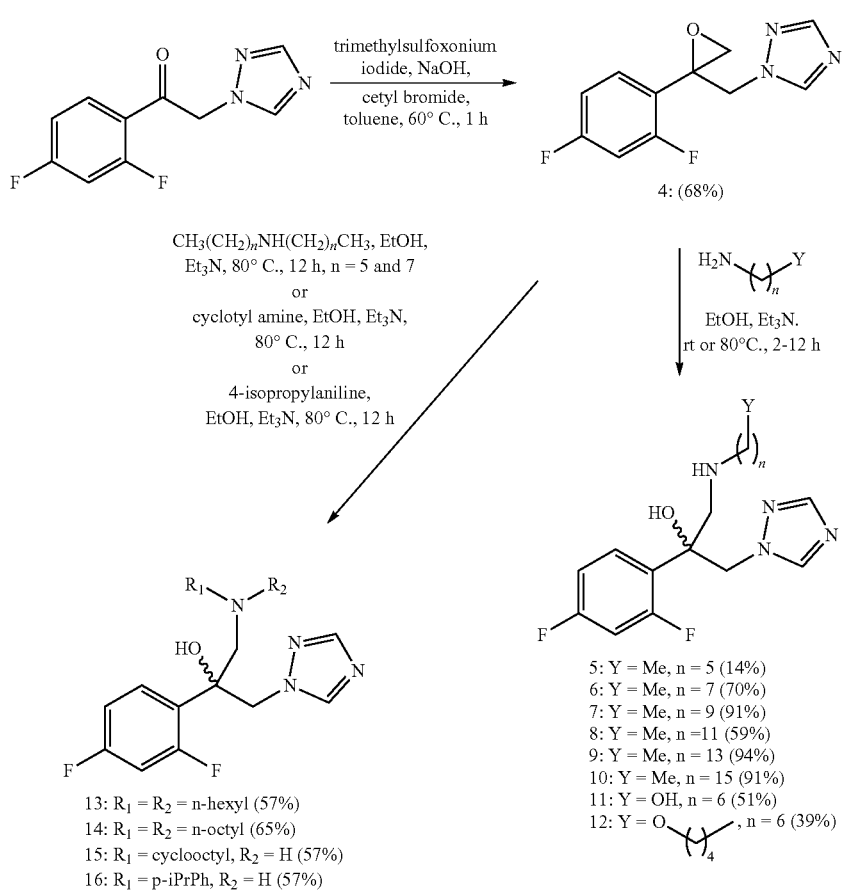

The presently-disclosed subject matter also includes pharmaceutical compositions including a compound as disclosed herein and a suitable pharmaceutical carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

The presently-disclosed subject matter also includes methods conferring antifungal activity and/or of treating a fungal infection, comprising administering an effective amount of a compound as disclosed herein.

As used herein, the term "effective amount" is the amount necessary or sufficient to inhibit the growth of fungus, or in certain instances, to kill the fungus, or in certain instances, to limit the ability of the fungus to reproduce In some embodiments of the method, the compound is administered to a subject.

As used herein, the term "subject" refers to a target of administration. The subject of the herein disclosed methods can be an animal, including vertebrates, such as a mammal, a fish, a bird, a reptile, or an amphibian. Thus, an animal subject can be a human or non-human, and veterinary uses are provided in accordance with the presently disclosed subject matter.

In some embodiments of the method, the compound is administered to a plant or to a crop. Accordingly, gardening and agricultural uses are contemplated.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732). The following abbreviations are used herein: FLC, fluconazole; VOR, voriconazole; ITC, itraconazole; POS, posaconazole; AmB, amphotericin B; KANB, kanamycin B; TOB, tobramycin; PK, pharmacokinetic; ATCC, American Type Culture Collection; mRBCs, mouse red blood cell; PI, propidium iodide dye; SAR, structure-activity-relationship.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

The presently-disclosed subject matter is further illustrated by the following specific but non-limiting examples. The following examples may include compilations of data that are representative of data gathered at various times during the course of development and experimentation related to the present invention.

EXAMPLES

Example 1

By developing a series of unique alkylated-FLC derivatives, we identified numerous promising antifungal agents with low hemolytic activity, low cytotoxicity, and great activity against *C. albicans*, non-*albicans Candida*, and *Aspergillus* strains. We showed that in contrary to what has generally been observed as a mechanism of action for molecules containing long alkyl chains (i.e., membrane disruption), our novel alkylated-FLC derivatives do not disrupt the fungal membrane, but instead target the ergosterol biosynthetic pathway by inhibiting the sterol 14α-demethylase enzyme involved in the first committed step responsible for the conversion of lanosterol into 4,4-dimethyl cholesta 8,14,24-trienol.

Design and Chemical Synthesis of Compounds 1-41

Figure 1:
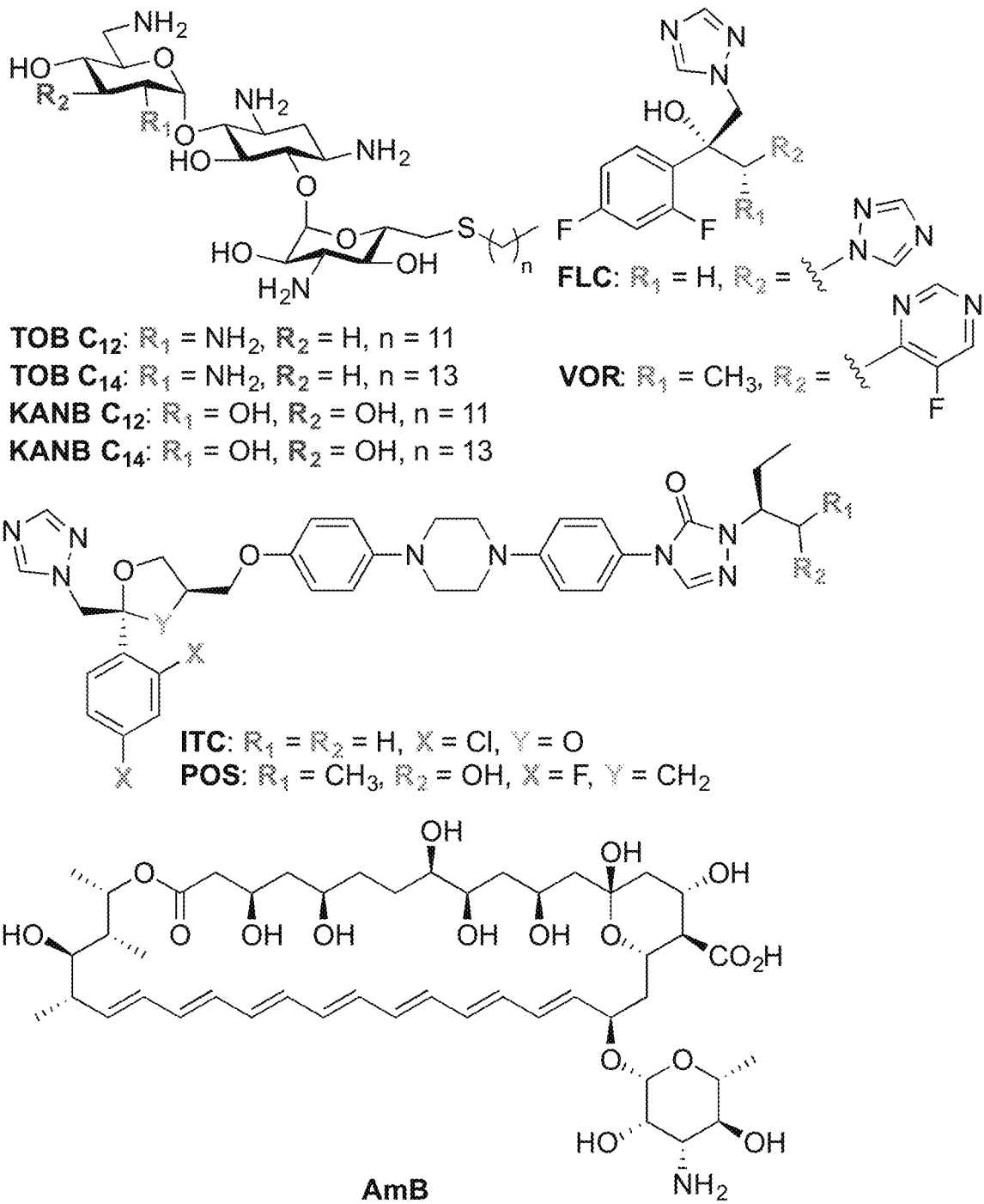
FIG. 1 includes the structures of certain compounds used in the studies described in the Examples.
Figures 2A, 2B:
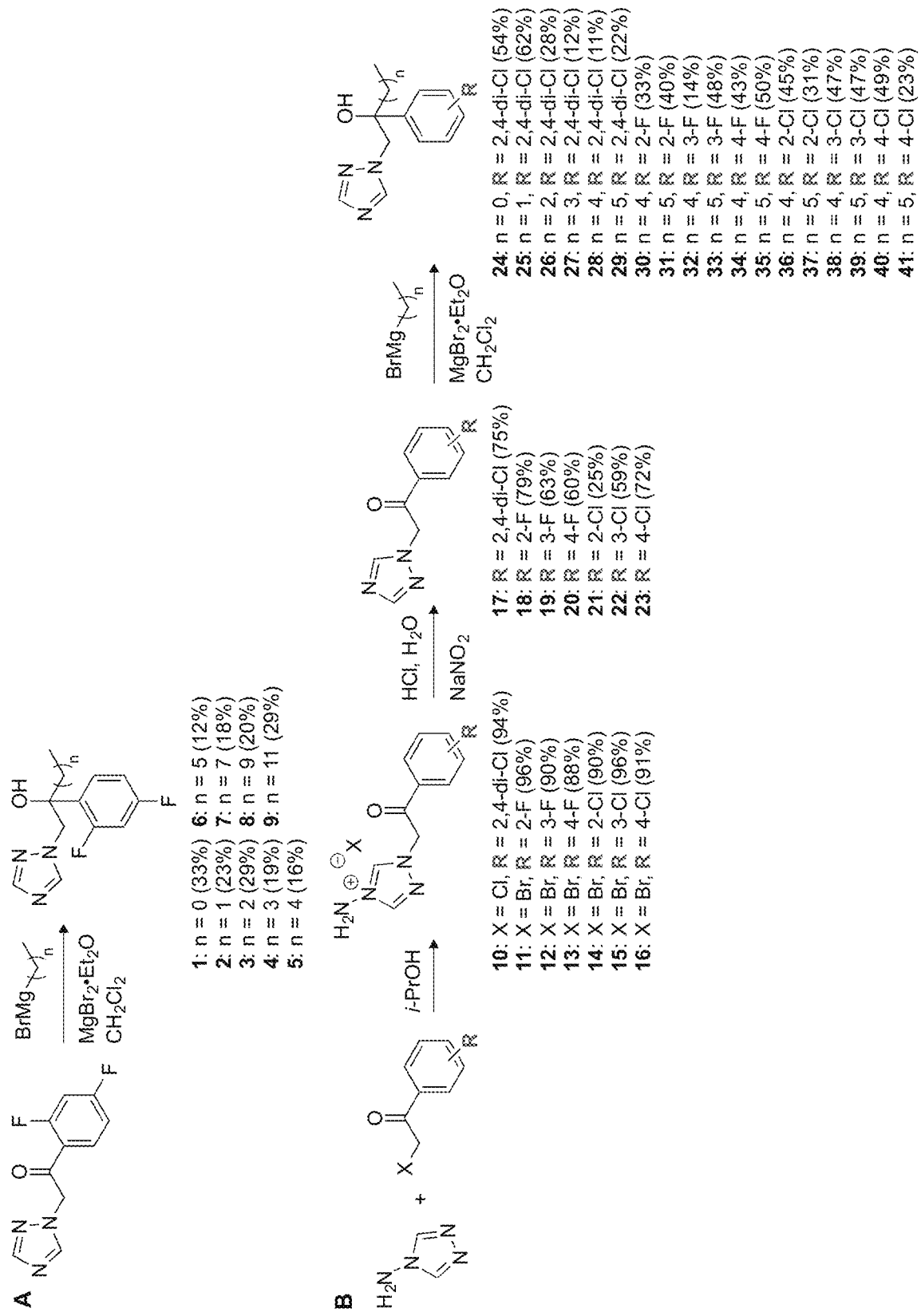
FIG. 2A-2B includes synthetic schemes for FIG. 2A the preparation of compounds 1-9 and FIG. 2B compounds 24-41.

The synthetic pathways for the preparation of target compounds 1-9 and 24-41 are depicted in FIG. 2. We synthesized compounds 1-9 using a straightforward strategy, which involved the Grignard reactions of 2,4-difluoro-α-(1H-1,2,4-triazolyl)acetophenone with different alkyl magnesium bromide in the presence of magnesium bromide ethyl etherate. Compounds 24-41 were prepared in three steps. 4-Amino-1,2,4-triazole was reacted with various 2-haloacetophenone in refluxing isopropanol to give 10-16 in excellent yields (88-96%). Compounds 10-16 were conveniently deaminated by $NaNO_2$ in aqueous HCl at room temperature. The desired products 17-23 were precipitated after neutralization of the reaction with potassium carbonate. The precipitates were collected by filtration and washed with water to afford pure products. No further purification was required because the excess of reactants was soluble in water and removed by filtration.

Compounds 17-23 were further converted to the corresponding products 24-41 by Grignard reaction in the presence of different alkyl magnesium bromide. With these compounds in hand, we aimed to answer the six following questions in terms of structure-activity-relationship (SAR) (Note: We put the identity of the compounds used to answer these questions into parentheses after the questions): (i) what is/are the optimal length(s) of the newly added alkyl chains to confer antifungal activity? (compounds 1-9); (ii) are these optimal chain lengths for compounds 1-9 the same as that of other families of n-alkylated molecules (e.g., aminoglycoside, benzimidazole, and ebsulfur derivatives)?; (iii) for a given alkyl chain length, would a 2,4-dichlorinated phenyl ring (compounds 24-29) confer better or worse antifungal activity than the 2,4-difluorinated phenyl ring (compounds 1-6)?; (iv) for a mono-substituted phenyl ring, which halogen substituent is best? (compounds 30-35 versus their counterparts 36-41); (v) for a specific alkyl chain length, which level of substitution (mono- versus di-) confer the best antifungal activity? (compound 5 versus compounds 30, 32, and 34; compound 6 versus compounds 31, 33, and 35; compound 28 versus compounds 36, 38, and 40; compound 29 versus compounds 37, 39, and 41); and (vi) for a given substituent, what is the optimal position (ortho, meta, or para) for mono-substitution on the phenyl ring? (compounds 30 versus 32 versus 34; compounds 31 versus 33 versus 35; compounds 36 versus 38 versus 40; compounds 37 versus 39 versus 41).

Antifungal Activity

The antifungal activity of our new azole compounds 1-9 and 24-41 was first evaluated against a panel of seven *Candida albicans* strains (A-G), three non-*albicans Candida* strains (H-I), and three *Aspergillus* strains (K-M) in a concentration range of 0.03-31.2 µg/mL (Table 1). Out of the *C. albicans* strains, two were classified as sensitive (strains C and E), one as intermediate (strain A), and four as resistant (strains B, D, F, and G) to FLC and ITC as defined by the American Type Culture Collection (ATCC). For all of our azole derivatives we report their MIC-0 values against *C. albicans* ATCC 10231 (strain A) and all *Aspergillus* strains (K-M), which correspond to complete growth inhibition of these fungi. However, as all other *Candida* strains tested (B-J) display a trailing growth effect, we report the MIC-2 values of our derivatives, which correspond to 50% growth inhibition of these fungal strains. The commercially available antifungals AmB, FLC, ITC, POS, and VOR were used as reference drugs for comparison. The MIC values presented for these five control drugs were either tested herein or correspond to our previously published data[5, 16] as indicated in Table 1. From here on, we designate antifungal activity as either excellent (<0.03-1.95 µg/mL), moderate (3.9-7.8 µg/mL), or poor (15.6-≥31.2 µg/mL) based on MIC values.

By performing a broad survey of the MIC data presented in Table 1, we rapidly could identify the following general trends. The three non-*albicans Candida* strains (strains H-I) tested were extremely susceptible to the majority of our compounds with strain J being the most susceptible, followed by strain I and then by strain H. Likewise, most of our compounds displayed excellent antifungal activities against two of the three *Aspergillus* spp. tested (strains L and M). However, against *Aspergillus flavus* ATCC MYA-3631 (strain K) only compounds 27-30 and 37-38 displayed moderate antifungal activity. When focusing on the *C. albicans* strains, we observed that our compounds were very effective against the majority of these strains (A, C-G), with the exception of the azole-resistant strain B. In fact, against strain B only two compounds (28 and 29) showed excellent antifungal activity and six compounds (5, 6, 7, 26, 27, and 40) displayed moderate antifungal activity. It is noteworthy to point out that most of our compounds maintained a high degree of activity against most of the azole-resistant strains of *C. albicans* tested. From these general observations, we identified compounds 28 and 29 to be our best FLC derivatives based on their excellent antifungal activities against 11 fungal strains, and moderate activities against 2 fungal strains out of all 13 strains evaluated. In addition, six compounds stood out (7, 27, 30, 31, 36, and 37) as they showed good to moderate antifungal activities against 10-13 fungal strains. It was promising to observe that only three compounds (1, 2, and 39) showed poor antifungal activities.

TABLE 1

MIC values$^a$ (in µg/mL) determined for compounds 1-9, 24-41, and for five control antifungal agents (AmB, FLC, ITC, POS, and VOR) against various yeast strains and filamentous fungi.

| | Yeast strains | | | | | | | | | | Filamentous fungi | | |
|---|---|---|---|---|---|---|---|---|---|---|---|---|---|
| Cpd # | A | B | C | D | E | F | G | H | I | J | K | L | M |
| 1 | >31.2 | >31.2 | >31.2 | >31.2 | >31.2 | >31.2 | 15.6 | >31.2 | >31.2 | 3.9 | >31.2 | 31.2 | >31.2 |
| 2 | 15.6 | >31.2 | 15.6 | 31.2 | >31.2 | >31.2 | 7.8 | >31.2 | 7.8 | 0.48 | >31.2 | 31.2 | >31.2 |
| 3 | 3.9 | 31.2 | 15.6 | 15.6 | 7.8 | 31.2 | 3.9 | >31.2 | 0.06 | 0.06 | >31.2 | 7.8 | 15.6 |
| 4 | 1.95 | 15.6 | 7.8 | 15.6 | 31.2 | 15.6 | 3.9 | 31.2 | 0.06 | <0.03 | 15.6 | 1.95 | 15.6 |
| 5 | 1.95 | 7.8 | 7.8 | 3.9 | 7.8 | 7.8 | 1.95 | 7.8 | 0.24 | <0.03 | 15.6 | 0.975 | >31.2 |
| 6 | 1.95 | 7.8 | 1.95 | 1.95 | 3.9 | 1.95 | 1.95 | 3.9 | 0.12 | <0.03 | 15.6 | 0.48 | 7.8 |
| 7 | 1.95 | 3.9 | 1.95 | 1.95 | 1.95 | 1.95 | 1.95 | 1.95 | 0.24 | ≤0.06 | 31.2 | 0.48 | 7.8 |
| 8 | 7.8 | 15.6 | 7.8 | 31.2 | 7.8 | >31.2 | >31.2 | 7.8 | 0.24 | 0.12 | >31.2 | 0.24 | 3.9 |
| 9 | >31.2 | >31.2 | 7.8 | >31.2 | 7.8 | 7.8 | >31.2 | 0.975 | >31.2 | 1.95 | >31.2 | 0.48 | 3.9 |
| 24 | >31.2 | >31.2 | 7.8 | 1.95 | >31.2 | >31.2 | >31.2 | 3.9 | 3.9 | 0.24 | >31.2 | 1.95 | >31.2 |
| 25 | 3.9 | >31.2 | 0.975 | 0.24 | 0.975 | 0.975 | 1.95 | 3.9 | 0.975 | <0.03 | 15.6 | 7.8 | 3.9 |
| 26 | 0.24 | 3.9 | 1.95 | 3.9 | 3.9 | 7.8 | 0.975 | 3.9 | 0.06 | <0.03 | 15.6 | 1.95 | 3.9 |
| 27 | 0.24 | 3.9 | 1.95 | 1.95 | 1.95 | 7.8 | 0.975 | 3.9 | 0.06 | <0.03 | 3.9 | 0.24 | 0.975 |
| 28 | 0.24 | 1.95 | 0.975 | 1.95 | 1.95 | 1.95 | 0.975 | 1.95 | 0.48 | <0.03 | 3.9 | 0.48 | 3.9 |
| 29 | 0.24 | 1.95 | 0.975 | 1.95 | 1.95 | 1.95 | 0.975 | 1.95 | 0.03 | <0.03 | 3.9 | 0.48 | 3.9 |
| 30 | 3.9 | >31.2 | 0.975 | 0.48 | 0.975 | 0.975 | 3.9 | 0.975 | 0.06 | 0.12 | 7.8 | 0.48 | 3.9 |
| 31 | 1.95 | >31.2 | 0.975 | 0.24 | 0.975 | 0.975 | 3.9 | 0.975 | 0.06 | 0.12 | 15.6-31.2 | 0.48 | 3.9 |

TABLE 1-continued

MIC values$^a$ (in μg/mL) determined for compounds 1-9, 24-41, and for five control antifungal agents (AmB, FLC, ITC, POS, and VOR) against various yeast strains and filamentous fungi.

| | Yeast strains | | | | | | | | | | Filamentous fungi | | |
|---|---|---|---|---|---|---|---|---|---|---|---|---|---|
| Cpd # | A | B | C | D | E | F | G | H | I | J | K | L | M |
| 32 | >31.2 | >31.2 | 3.9 | 3.9 | 3.9 | 3.9 | >31.2 | 7.8 | 3.9 | 3.9 | ≥31.2 | 0.24 | 3.9 |
| 33 | >31.2 | >31.2 | 1.95 | 1.95 | 1.95 | 0.975 | 31.2 | 7.8 | 3.9 | 1.95 | >31.2 | 3.9 | 31.2 |
| 34 | 3.9 | >31.2 | 7.8 | 0.975 | 3.9 | 1.95 | >31.2 | 7.8 | 0.975 | 0.48 | >31.2 | 3.9 | 31.2 |
| 35 | 15.6 | >31.2 | 7.8 | 0.975 | 7.8 | 31.2 | 7.8 | 7.8 | 0.975 | 0.48 | >31.2 | 1.95 | 15.6 |
| 36 | 7.8 | >31.2 | 0.975 | 0.48 | 0.975 | 0.975 | 7.8 | 0.975 | 0.975 | 0.12 | >31.2 | 0.975 | 15.6 |
| 37 | 7.8 | >31.2 | 0.975 | 1.95 | 1.95 | 0.975 | 7.8 | 0.975 | 0.12 | 0.12 | 1.95-3.9 | 0.06 | 0.48 |
| 38 | >31.2 | 31.2 | >31.2 | 3.9 | 1.95 | 1.95 | >31.2 | >31.2 | >31.2 | >31.2 | 3.9 | 0.06 | 0.48 |
| 39 | >31.2 | 31.2 | >31.2 | 7.8 | 7.8 | 7.8 | >31.2 | >31.2 | >31.2 | >31.2 | >31.2 | 3.9 | >31.2 |
| 40 | 1.95 | 7.8 | 15.6 | 1.95 | 15.6 | 3.9 | 1.95 | 3.9 | 0.12 | 0.06 | >31.2 | 7.8 | >31.2 |
| 41 | 1.95 | 31.2 | 7.8 | 3.9 | 31.2 | 3.9 | 1.95 | >31.2 | 1.95 | >31.2 | >31.2 | 3.9 | 15.6 |
| AmB | 3.9 | 3.9 | 1.95 | 0.975 | 1.95 | 3.9 | 3.9 | 1.95 | 3.9 | 1.95 | 15.6 | 15.6 | 3.9 |
| FLC | 62.5$^b$ | >125$^b$ | 15.6$^b$ | >125$^b$ | >125$^b$ | 62.5$^b$ | 62.5$^b$ | >31.2$^c$ | >31.2$^c$ | 1.95$^c$ | 62.5$^c$ | 62.5$^c$ | 62.5$^c$ |
| ITC | 0.5$^b$ | >62.5$^b$ | 7.8$^b$ | 31.2$^b$ | 31.2$^b$ | 31.2$^b$ | 31.2$^b$ | 7.8$^c$ | 0.48$^c$ | 0.12$^c$ | 0.48$^c$ | 0.195$^b$ | 0.975$^c$ |
| POS | 0.5$^b$ | >62.5$^b$ | 7.8$^b$ | 31.2$^b$ | 31.2$^b$ | 15.6$^b$ | 15.6$^b$ | 0.12$^c$ | 0.06$^c$ | <0.03$^c$ | 0.24$^c$ | 0.195$^b$ | 0.48$^c$ |
| VOR | 0.24$^c$ | 3.9$^c$ | 1.95$^c$ | 1.95$^c$ | 0.975$^c$ | 7.8$^c$ | 1.95$^c$ | 0.06$^c$ | 0.12$^c$ | <0.03$^c$ | 0.24$^c$ | 0.03$^c$ | 0.12$^c$ |

Yeast strains: A = *Candida albicans* ATCC 10231, B = *C. albicans* ATCC 64124, C = *C. albicans* ATCC MYA-2876(S), D = *C. albicans* ATCC 90819(R), E = *C. albicans* ATCC MYA-2310(S), F = *C. albicans* ATCC MYA-1237(R), G = *C. albicans* ATCC MYA-1003(R), H = *Candida glabrata*. ATCC 2001, I = *Candida krusei* ATCC 6258, J = *Candida parapsilosis* ATCC 22019.
NOTE:
Here, the (S) and (R) indicate that ATCC reports these strains to be susceptible (S) and resistant (R) to ITC and FLC.
Filamentous fungi: K = *Aspergillus flavus* ATCC MYA-3631, L = *Aspergillus nidulans* ATCC 38163, M = *Aspergillus terreus* ATCC MYA- 3633.
Known antifungal agents: AmB = amphotericin B, FLC = fluconazole, ITC = itraconazole, POS = posaconazole, and VOR = voriconazole.
$^a$For yeast strain A and all filamentous fungi MIC-0 are reported for compounds 1-9 and 24-41, whereas for all other strains tested, MIC-2 are reported for these compounds.
Note:
MIC-0 values are reported for AmB, whereas MIC-2 values are reported for the control azoles FLC, ITC, POS, and VOR.
$^{b,c}$Values previously reported in refs$^5$ and$^{16}$.

SAR Analysis

In concordance with our antifungal results discussed above (Table 1), we approached the eight questions raised at the beginning of this study.

(i) What is/are the optimal length(s) of the newly added alkyl chains to confer antifungal activity? In order to decipher which chain length confers optimal antifungal activity, we synthesized nine compounds (1-9) by replacing one of the two triazole rings of FLC with linear alkyl chains varying in length from 1-12 carbons ($C_1$-$C_{12}$) (Table 1). When glancing at the MIC data in Table 1, we observed that compounds 1-4 with shorter $C_1$-$C_4$ alkyl substituents and compounds 8 and 9 with longer $C_{10}$ and $C_{12}$ alkyl moieties were in general not great at stopping fungal cell growth. However, compounds 5-7 with alkyl chains of medium lengths, $C_5$, $C_6$, and $C_8$, were in general great antifungals. When carefully analyzing the MIC data presented in Table 1, we determined that in most cases, compounds 1 and 2 with the two shortest alkyl chains exhibited the worse antifungal profile with most MIC values varying between 15.6-≥31.2 μg/mL against 10 (strains A-F, H, and K-M) of the 13 fungal strains tested. In addition, compound 1 with a methyl substituent also displayed poor antifungal activity (MIC=15.6-≥31.2 μg/mL) against strains G and I. Actually compound 1 only displayed moderate activity against *C. parapsilosis* ATCC 22019 (strain J), whereas compound 2 displayed excellent activity (0.48 μg/mL) against this strain J and moderate activity (MIC=7.8 μg/mL) against strains G and I. Likewise, compounds 3 and 4 with $C_3$ and $C_4$ alkyl chains were found to be poor antifungals (15.6-≥31.2 μg/mL) against 6 (strains B, D, F, H, K, and M) of the 13 strains tested. It is to note that the growth of these 6 strains was also not easily inhibited by compounds 1 and 2. However, unlike compounds 1 and 2, compounds 3 and 4 showed some improvement in terms of their antifungal activity against strains A, C, E, G, and L. Compound 3 displayed moderate antifungal activity (3.9-7.8 μg/mL) against strains A, E, G, and L, whereas compound 4 displayed moderate activity only against strains C and G. On a good note, compounds 3 and 4 displayed excellent antifungal activity (<0.03-0.06 μg/mL) against strains I and J. When looking at compounds 5-7 with alkyl chains of medium lengths, we observed that they exerted moderate to excellent antifungal activity against all the strains tested with the exception of strain K against which they displayed poor activity. We noticed that compound 7 exerted the best antifungal activities followed by compound 6 and then by compound 5. In general, compound 7 showed excellent antifungal activity against 10 (strains A, C-J, and L), moderate antifungal activity against two (strains B and M), and poor activity against one (strain K) out of the 13 fungal strains tested. Similarly, compound 6 showed excellent antifungal activity against 8 (strains A, C-G, I-J, and L), and moderate antifungal activity against 4 (strains B, E, H, and M) out of the 13 fungal strains tested. Finally, compound 5 exhibited excellent antifungal activity against 5 (strains A, G, I, J, and L), moderate antifungal activity against 6 (strains B-F, and H), and poor antifungal activity against two (strains K and M) of the 13 strains tested. From these observations, we determined that increasing the length of the alkyl chain substituent results in an overall increase in antifungal activity. This prompted us to explore compounds 8 and 9 with longer $C_{10}$ and $C_{12}$ alkyl moieties. We observed that compounds 8 and 9 displayed poor antifungal activity against 5 (strains B, D, F, G, and K) and 6 (strains A, B, D, G, I, and K) out of 13 fungal strains, respectively. Additionally, we observed moderate inhibition of 5 (strains A, C, E, H, and M) and 4 (strains C, E, F, and M) of the 13 strains tested by compounds 8 and 9, respectively. On the basis of our in-depth analysis of the MIC data for compounds 1-9, we concluded that the optimal chain length required for the FLC derivatives to confer maximal antifungal activity were $C_5$-$C_8$.

(ii) Are these optimal $C_5$-$C_8$ chain lengths for our FLC derivatives the same as that of other families of n-alkylated molecules (e.g., aminoglycoside, benzimidazole, and ebsulfur derivatives)? In recent years, the addition of linear alkyl chains to drug scaffolds has gained popularity as it has been demonstrated that it improves the activity of the compounds when compared to the parent non-alkylated molecules. Aminoglycosides are of the families of antibiotics to which alkyl chains have been added. It was shown that the optimal chain lengths required for maximal antifungal activity were $C_8$ for kanamycin A[17] and $C_{12}$-$C_{14}$ for kanamycin B[4] and tobramycin.[5] For n-alkylated ebsulfur derivatives, the optimal chain lengths required to confer antifungal activity were reported to be $C_5$-$C_6$.[6] Interestingly, alkyl chains varying in length between 1-3 carbons ($C_1$-$C_3$) were found to confer optimal antifungal activity when attached to a benzimidazole core.[16] From these data, it is clear that there is no universal alkyl chain length that can be utilized to confer prime antifungal activity. Consequently, one should always test a range of alkyl chains to determine the optimal length(s) for any new drug scaffold to be derivatized.

(iii) For a given alkyl chain length, would a 2,4-dichlorinated phenyl ring confer better or worse antifungal activity than the 2,4-difluorinated phenyl ring? Although compound 7 was identified as the best antifungal in our series based on its MIC values, we were concerned that the longer alkyl chain ($C_8$) could cause potential toxicity to mammalian cells. Therefore, for the next step in our SAR study, we decided to keep the length of the alkyl chains present in compounds 24-29 between 1-6 carbons. To explore the importance of the two fluoro groups on the phenyl ring of compounds 1-6, we generated their dichlorinated counterparts 24-29. By performing a pairwise comparison of for the MIC values of compounds 1 versus 24, 2 versus 25, 3 versus 26, 4 versus 27, 5 versus 28, and 6 versus 29, we concluded that the compounds with the 2,4-dichlorinated phenyl ring always displayed better antifungal activities than those containing the two fluoro groups. We also determined that the compounds displaying the best overall antifungal activities in this series were 28 and 29, which contained $C_5$ and $C_6$ alkyl chains, respectively. For this reason, we next generated molecules 30-41 with $C_5$ and $C_6$ alkyl chains and monosubstituted (with fluoro or chloro) phenyl rings.

(iv) For a mono-substituted phenyl ring, which halogen substituent (fluoro or chloro) is best? After establishing that two chloro groups were better than two fluoro moieties, we wanted to determine if the trend would remain when only one halogen substituent was attached to the phenyl ring. In order to shed light on this, we synthesized 12 additional compounds, 30-41, and performed direct pairwise comparisons (30 versus 36, 31 versus 37, 32 versus 38, 33 versus 39, 34 versus 40, 35 versus 41) in terms of their activity against the fungal strains tested based on our MIC data (Table 1). Interestingly, in contrary to what we observed with the dihalogenated molecules, we found that, in most cases, the mono-substituted phenyl rings with a fluoro substituent displayed better antifungal activities than its counterpart with a chloro substituent. Briefly, we found that compound 30 (with a 2-F) repeatedly showed better antifungal activity against *C. albicans* strains, non-*albicans Candida* strains, and *Aspergillus* strains when compared to its counterpart 36 (with a 2-Cl). Compounds 31 (with a 2-F) and 32 (with a 3-F) displayed better antifungal activities against *C. albicans* as well as non-*albicans Candida* strains, whereas their respective counterpart 37 and 38 showed better activity only against *Aspergillus* strains. Similarly, compound 33 (with a 3-F) exhibited better antifungal activity against *C. albicans* strains than compound 39 (with a 3-Cl). Both compounds 33 and 39 showed almost identical activity against *Aspergillus* strains. Finally, compound 34 (with a 4-F) showed better antifungal activity against *C. albicans* strains, worse antifungal activity against non-*albicans Candida* strains, and equivalent antifungal activities against *Aspergillus* strains than its counterpart compound 40 (with a 4-Cl). Likewise, compound 35 (with a 4-F) showed worse antifungal activity against *C. albicans* as well as non-*albicans Candida* strains, but identical antifungal activity against *Aspergillus* strains than its counterpart compound 41 (with a 4-Cl).

(v) For a specific alkyl chain length, which level of substitution (mono- versus di-) confer the best antifungal activity? As previously mentioned, based on our MIC data we concluded that compounds with $C_5$-$C_6$ chain lengths confer the best antifungal activities. We next decided to explore the effect of the level of substitution (mono- versus di-) on the phenyl ring for our compounds with $C_5$-$C_6$ alkyl chain length based by comparing the MIC data obtained for compound 5 versus compounds 30, 32, and 34; compound 6 versus compounds 31, 33, and 35; compound 28 versus compounds 36, 38, and 40; as well as compound 29 versus compounds 37, 39, and 41. We noticed that the 2,4-difluorinated compounds 5 and 6 displayed inferior antifungal activity when compared to their mono-2-substituted counterparts 30 and 31. On the other hand, both compounds 5 and 6 showed better antifungal activities than their mono-3-substituted counterparts 32 and 33, and than their mono-4-substituted counterparts 34 and 35. Interestingly, we observed that the 2,4-dichlorinated compounds 28 and 29 always displayed better antifungal activity than any of their mono-substituted counterparts.

(vi) For a given substituent (fluoro of chloro), what is the optimal position (ortho, meta, or para) for mono-substitution on the phenyl ring? Finally based on a direct comparison of compounds 30 versus 32 versus 34; compounds 31 versus 33 versus 35; compounds 36 versus 38 versus 40; compounds 37 versus 39 versus 41, we found that substitution at the ortho position (compounds 30, 31, 36, and 37) confers greater antifungal activity than does that at the para position (compounds 34, 35, 40, and 41). Substitution at the meta position (compounds 32, 33, 38, and 39) is the least optimal to confer antifungal activity.

Time-Kill Assay

Figures 3A, 3B:
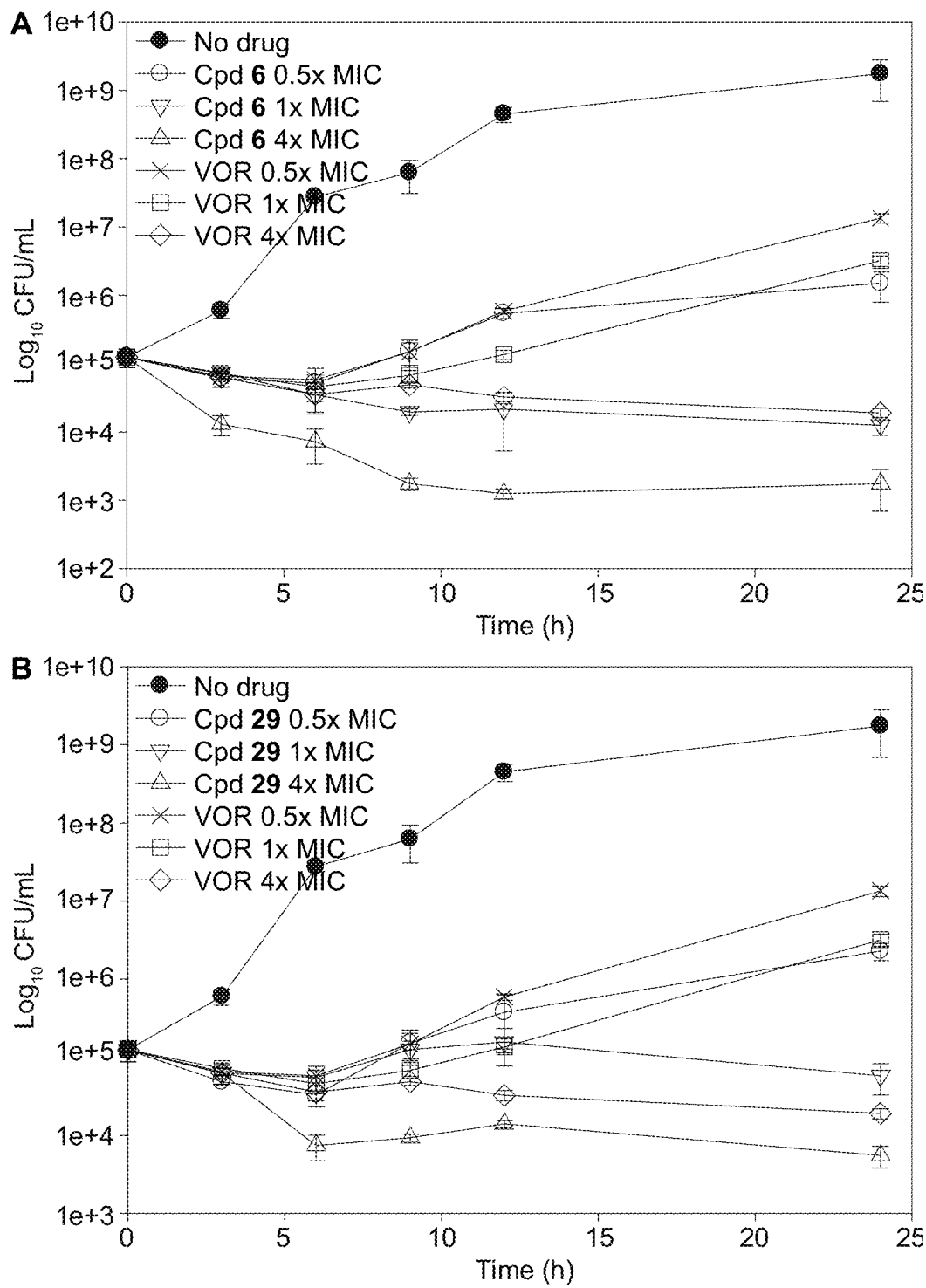
FIG. 3A-3B includes representative time-kill studies of compounds 6 and 29, and VOR against C. albicans ATCC 10231 (strain A). Yeast cells were either treated with FIG. 3A. compound 6 (white circle (0.5 MIC), inverted white triangle (1×MIC), and white triangle (4×MIC)) or FIG. 3B. compound 29 (white circle (0.5×MIC), inverted white triangle (1×MIC), and white triangle (4×MIC)). In both panels A and B VOR was used as a control (cross (0.5×MIC), white square (1×MIC), and white diamond (4×MIC)). A no drug control (black circle) is also presented in both panels.

Our in-depth SAR analysis has identified several potential newly synthesized antifungals among which compounds 6 and 29 stood to be the best. Therefore, compounds 6 and 29 were further examined for their antifungal potency against a representative *C. albicans* strain ATCC 10231 (strain A) by performing a time-kill assay over a 24-h period (FIG. 3). In general, we observed dose-dependent killing effect by our compounds 6 and 29 as well as by a reference drug voriconazole (VOR) against *C. albicans* ATCC 10231 (strain A). At 0.5×MIC, compounds 6 and 29 showed fungistatic effects against strain A for the first 12 h of growth, and after that the growth was increased by 1 $\log_{10}$ CFU at 24 h for both of these compounds. Similarly, at 1×MIC, both compounds maintained the fungistatic effect up until 12 h followed by a reduction in CFU of strain A by 1 $\log_{10}$ by compound 6 and 0.25 $\log_{10}$ by compound 29 at 24 h. However, at 4×MIC, compounds 6 and 29 displayed fungicidal effect by achieving ≥2 $\log_{10}$ and 1.25 $\log_{10}$ reduction of CFU of strain A at 9 h and 6 h, respectively (FIG. 3). More importantly, we also noticed that our compounds 6 and 29 showed either superior or comparable growth inhibitory effect against *C. albicans*

ATCC 10231 (strain A) when compared to the reference drug (VOR) under similar conditions.

Hemolysis Assay

Figure 4:
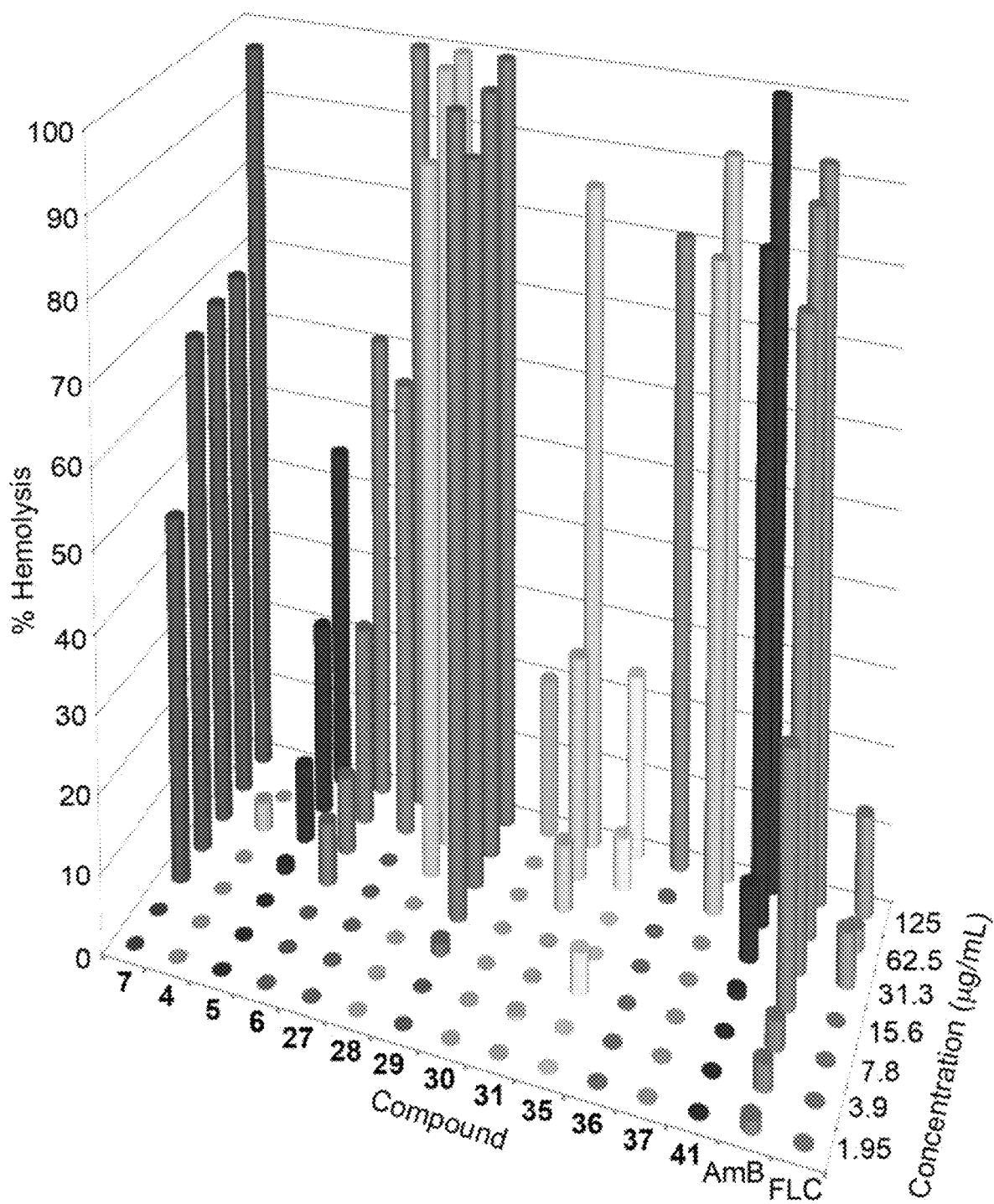
FIG. 4 is a 3D bar graph depicting the dose-dependent hemolytic activity of fluconazole derivatives against mouse erythrocytes. Mouse erythrocytes were treated and incubated for 1 h at 37° C. with compounds 4-6, 27-31, 35-37, 41, AmB, and FLC at concentrations ranging from 1.95-125 μg/mL. Triton X-100® (1% v/v) was used as a positive control (100% hemolysis, not shown).

With the promising antifungal activity of our newly synthesized alkylated FLC derivatives, we wanted to confirm that they would display none or reasonable (i.e., <50% at 10×MIC) hemolytic activity against red blood cells. In order to determine the selectivity of our FLC derivatives towards fungal cells, we selected our 13 best compounds (4-7, 27-31, 35-37, and 41) out of 27 to evaluate their hemolytic effect against mouse red blood cells (mRBCs) (FIG. 4). As observed with their antifungal activity, compounds 4-7 also showed chain-length-dependent hemolytic activity on mRBCs in the order of 4 ($C_4$)<5 ($C_5$)<6 ($C_6$)<7 ($C_8$). Briefly, no measurable hemolysis was detected for compound 4 even at the highest concentration of 125 µg/mL used. Likewise, compounds 5 and 6 lysed 45% of mRBCs at 125 µg/mL (4 to 4096-folds higher concentration than their antifungal MIC values) and 26% of mRBCs at 62.5 µg/mL (4 to 2048-folds higher concentration than their antifungal MIC values), suggesting a minimal hemolytic effect by compounds 5 and 6. On the other hand, compound 7 induced 47% lysis of mRBCs at 7.8 µg/mL, which was either lower concentration or 64-fold higher concentration than its antifungal MIC values. Although compound 7 with a $C_8$ alkyl chain was one of the most active compound, it readily lysed the mRBCs as well and, therefore, we were right about our hypothesis that the longer chain could be problematic. Next, we analyzed the hemolytic activity of the dichlorinated compounds 27-29 and compared them with that of their difluorinated counterparts 4-6. Like compounds 4-6, compounds 27-29 showed the chain-length-dependent hemolytic activity in the order of 27 ($C_4$)<28 ($C_5$)<29 ($C_6$). However, the 2,4-dichlorinated compounds were more hemolytic against mRBCs when compared to their 2,4-difluorinated counterparts. Concisely, compound 27 lysed 59% of mRBCs at 62.5 µg/mL, which was 16 to 2048-folds higher concentration than its antifungal MIC values. Similarly, compound 28 showed no detectable hemolysis at up to 15.6 µg/mL (4 to 512-folds higher concentration than its antifungal MIC values), but significantly increased by 90% at above that concentration. Additionally, compound 29 did not show hemolysis at up to 7.8 µg/mL, but the effect was bumped up to 100% at the concentration above that. We also found that the 2,4-difluorinated compounds 5 and 6 displayed either more or equal hemolytic activity than their mono-fluorinated counterparts 30 and 31. However, the 2,4-difluorinated compounds 5 and 6 were always less hemolytic than their mono-chlorinated counterparts 36 and 37. On the other hand, the dichlorinated compounds 28 and 29 consistently showed more hemolytic activity than their mono-fluorinated (36 and 37) as well as mono-chlorinated (30 and 31) counterparts against mRBCs. Finally, by performing pair-wise comparisons of the hemolytic activity of our compounds (30 versus 36, 31 versus 37, and 35 versus 41), we evaluated the effects of the halide substituent identity (fluoro versus chloro) and position(s) (ortho versus para) on the phenyl ring. In general, the 2-F group (compounds 30 and 31) resulted in less hemolytic effect than the 2-Cl (compounds 36 and 37). Likewise, the 4-F (compound 35) exhibited less hemolytic activity than the 4-Cl (compound 41). Notably, we noticed that the majority of our newly synthesized FLC derivatives displayed less hemolytic effect than the control drug AmB.

Cytotoxicity Assay

Figures 5A, 5B:
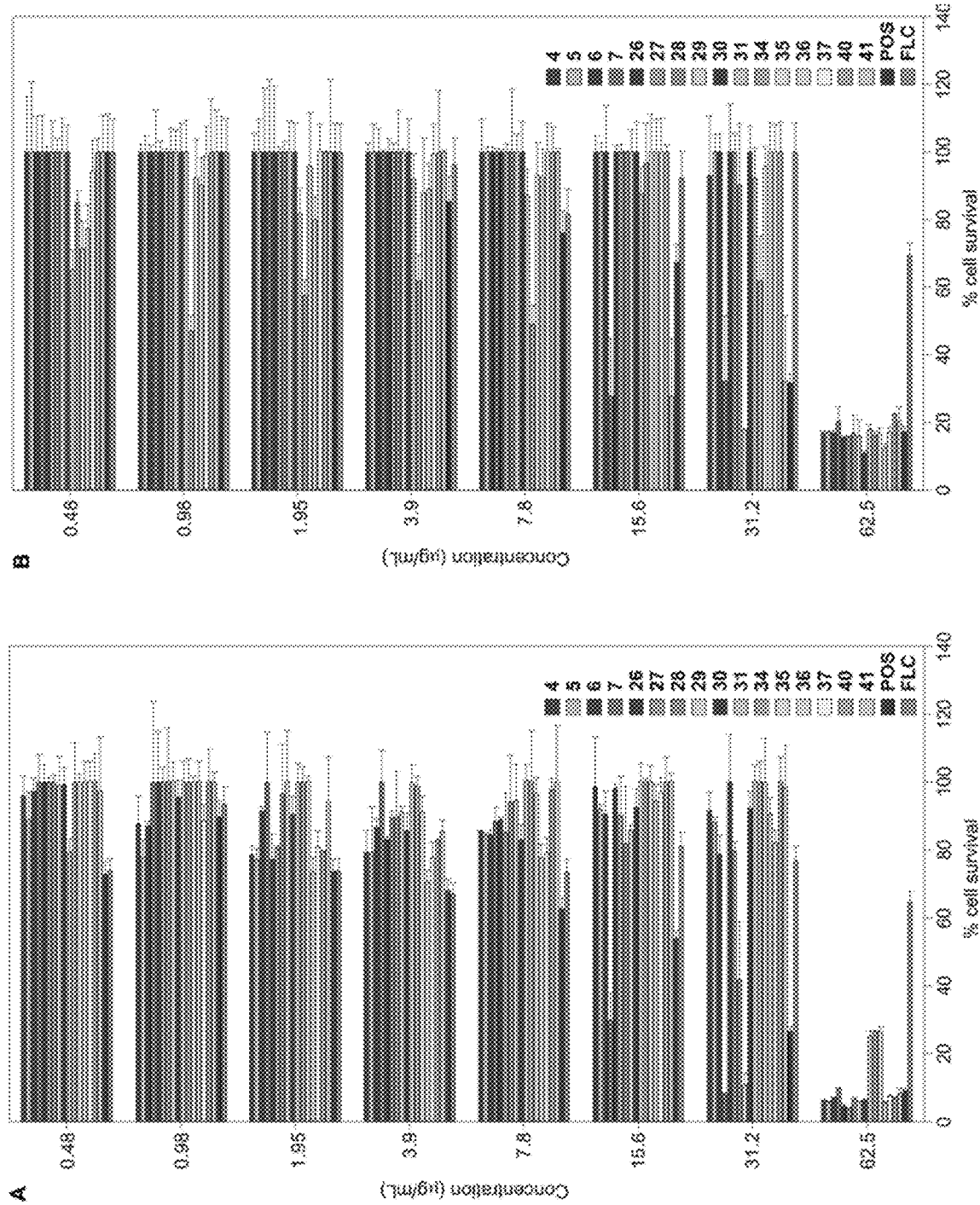
FIG. 5A-5B charts mammalian cell toxicity of compounds 4-7, 26-31, 34-37, 40, and 41, as well as the control drugs FLC and POS against FIG. 5A. A549 cell line and FIG. 5B. BEAS-2B cell line.

Fungi are eukaryotes that share similar cellular and biochemical features with mammalian cells. As a result, the drugs that are designed to target fungi could cause unwanted side effects on mammalian cells. To further determine the selectivity of our FLC derivatives towards fungal cells, we tested our 16 best compounds (4-7, 26-31, 34-37, and 40-41) for their toxicity against two nucleated mammalian cell lines, A549 and BEAS-2B (FIG. 5). In parallel, we also used two FDA approved antifungal agents, AmB and FLC, as comparators. Encouragingly, we observed that the majority of our difluorinated compounds (4-6, with the exception of 7) were generally non-toxic to both mammalian cell lines tested with $IC_{50}$ values of >31.2 µg/mL. These $IC_{50}$ values are 4 to 1024-folds higher than the respective antifungal MIC values for these derivatives. Although compound 7 (one of the best antifungal in the series) was relatively toxic among the difluorinated group, it showed no toxicity at up to a concentration of 7.8 µg/mL against both mammalian cell lines. Similarly, our dichlorinated compounds 26-29 were also found to be non-toxic as they allowed for >85% cell survival at 15.6 µg/mL. Additionally, no cytotoxicity was detected for our compounds with 2-F (compounds 30 and 31), 4-F (compounds 34 and 35), 2-Cl (compounds 36 and 37), and 4-Cl (compounds 40 and 41) against both cell lines tested, with $IC_{50}$ values of >31.2 µg/mL. We were also excited by the fact that our FLC derivatives exhibited better safety profile than the FDA approved drug AmB (only 30% cell survival at 15.6 µg/mL).

Membrane Permeabilization Assay

Figure 6:
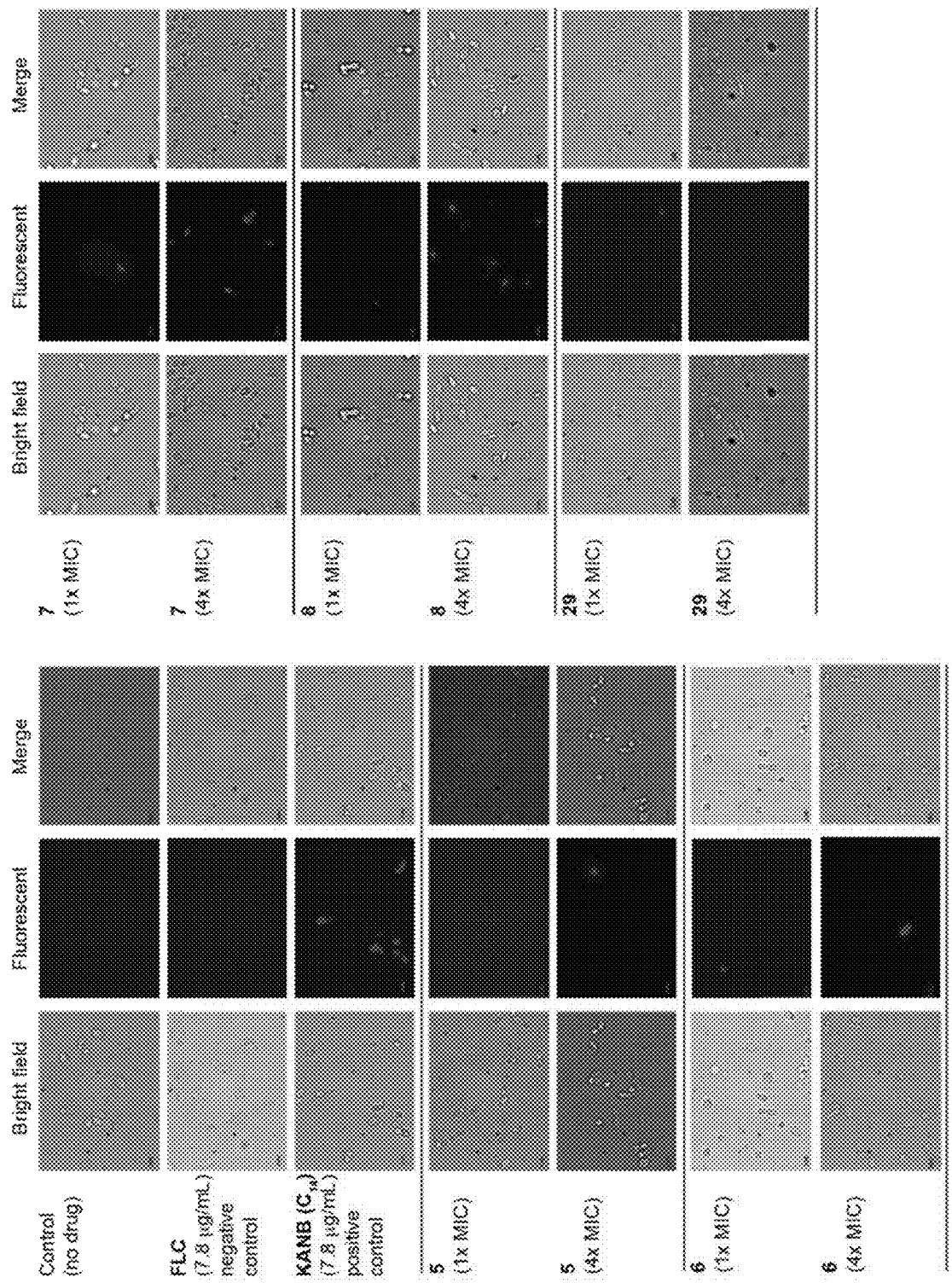
FIG. 6 illustrates the effect of FLC and its analogues 6 and 29 on the cell membrane integrity of C. albicans ATCC 10231 (strain A). From top to bottom: propidium iodide (PI) dye uptake by yeast cells without drug, with FLC (7.8 μg/mL), KANB ($C_{14}$) (7.8 μg/mL), compound 6 (at 1×MIC and 4×MIC), and compound 29 (at 1×MIC and 4×MIC).

We previously demonstrated that amphiphilic molecules can exert their activity by disrupting the membrane of fungal cells.[5, 6, 16-19] Based on these findings, we also speculated that our alkylated FLC derivatives could potentially cause antifungal activity by disrupting the fungal membrane. To investigate the mechanism of action of our FLC derivatives, we tested compounds 5-8 and 29 to evaluate their effect on fungal membrane integrity using propidium iodide dye (PI) (FIG. 6). PI is a membrane impermeable dye that cannot enter the intact cell unless the cell membrane is damaged. Using these compounds, we also wanted to determine how do the lengths of the alkyl side chains correlate with the membrane disruption potential of these antifungal agents. We also used a kanamycin B derivative KANB ($C_{14}$) with a linear alkyl chain of 14 carbons and FLC as positive and negative controls, respectively. Interestingly, we found that none of our compounds 5-8 and 29 (at either 1×MIC or 4×MIC) induced cellular uptake of PI dye into *C. albicans* ATCC 10231 (strain A) regardless of their alkyl chain length. These data indicated that the antifungal mode of action of our FLC derivatives is not membrane disruption.

Determination of Sterol Composition

Based on our membrane permeabilization assay, we ascertained that none our FLC derivatives are able to cause membrane disruption of *C. albicans* ATCC 10231 (strain A) (FIG. 6). This prompted us to investigate by gas chromatography-mass spectrometry (GC-MS) the potential of our FLC derivatives to exert their antifungal action by inhibiting the sterol 14α-demethylase enzyme of the ergosterol biosynthetic pathway, similarly to the parent FLC (FIG. 7A). We selected one of our best compound, 29, to evaluate its effect on sterol composition of two strains, *C. albicans*

ATCC 10231 (strain A, FIG. 7B) and *C. albicans* ATCC 64124 (strain B, FIG. 7E), at the sub-MIC levels of 0.125 µg/mL and 1.95 µg/mL, respectively. We also used FLC at 0.125 µg/mL (against strain A, FIG. 7C) and at 1.95 µg/mL (against strain B, FIG. 7F) as a comparator. No drug controls were also performed (FIGS. 7D and G).

Based on our sterol profile results (summarized in FIG. 7H), we determined that in the absence of an azole drug strain A accumulated ~91% ergosterol, suggesting that sterol biosynthesis was fully functional in this fungal strain. Interestingly, in the absence of an azole drug we observed a different trend against strain B. Indeed, strain B accumulated a relatively low amount of ergosterol (~54%) and an increased amount of lanosterol (~29%) and eburicol (~6%) in comparison to what was observed with strain A. It is important to note that *C. albicans* ATCC 64124 (strain B) is an azole-resistant strain with a mutation in the sterol 14α-demethylase enzyme, which probably contributed to its different sterol profile. Similarly, when strain A was treated with FLC (0.125 µg/mL), ergosterol (~93%) was found to be the predominant sterol in the cells, indicating that FLC had no effect on ergosterol biosynthesis in this specific fungal strain. This observation could be easily explained by the fact that the concentration of FLC utilized in the assay was ~500-fold lower than the antifungal MIC value (62.5 µg/mL) for FLC against this strain. However, when strain B was treated with FLC (1.95 µg/mL), we detected a relatively low amount of ergosterol (~48%) and an increased amount of lanosterol (~30%) and eburicol (~12%) comparison to what was observed with strain A. In contrary to what we observed with the non-treated and FLC-treated strain A, with compound 29, we detected a reduction in the amount of ergosterol (~49%) with the concomitant increase 3β,6α-diol (~19%). Interestingly, when strain B was treated with compound 29, we saw a significant decrease in the amount of ergosterol (~6%) and a drastic increase in the amount of eburicol (~48%). In addition, no traces of the fungistatic metabolite 14α-methylergosta-8,24,(28)-dien-3β,6α-diol were detected in compound 29-treated strain B. These results indicated that our compound 29 inhibits the sterol 14α-demethylase enzyme of fungal cells, and thereby affects the ergosterol biosynthetic pathway.

Example 2

Figure 8A:
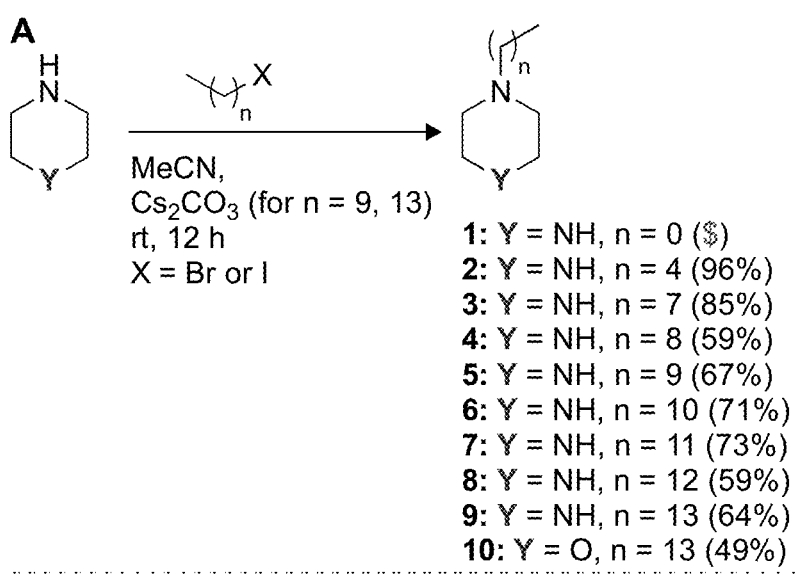
FIG. 8A is a Synthetic scheme for the preparation of piperazine derivatives 1-9 and morpholine derivative 10.
Figure 8B:
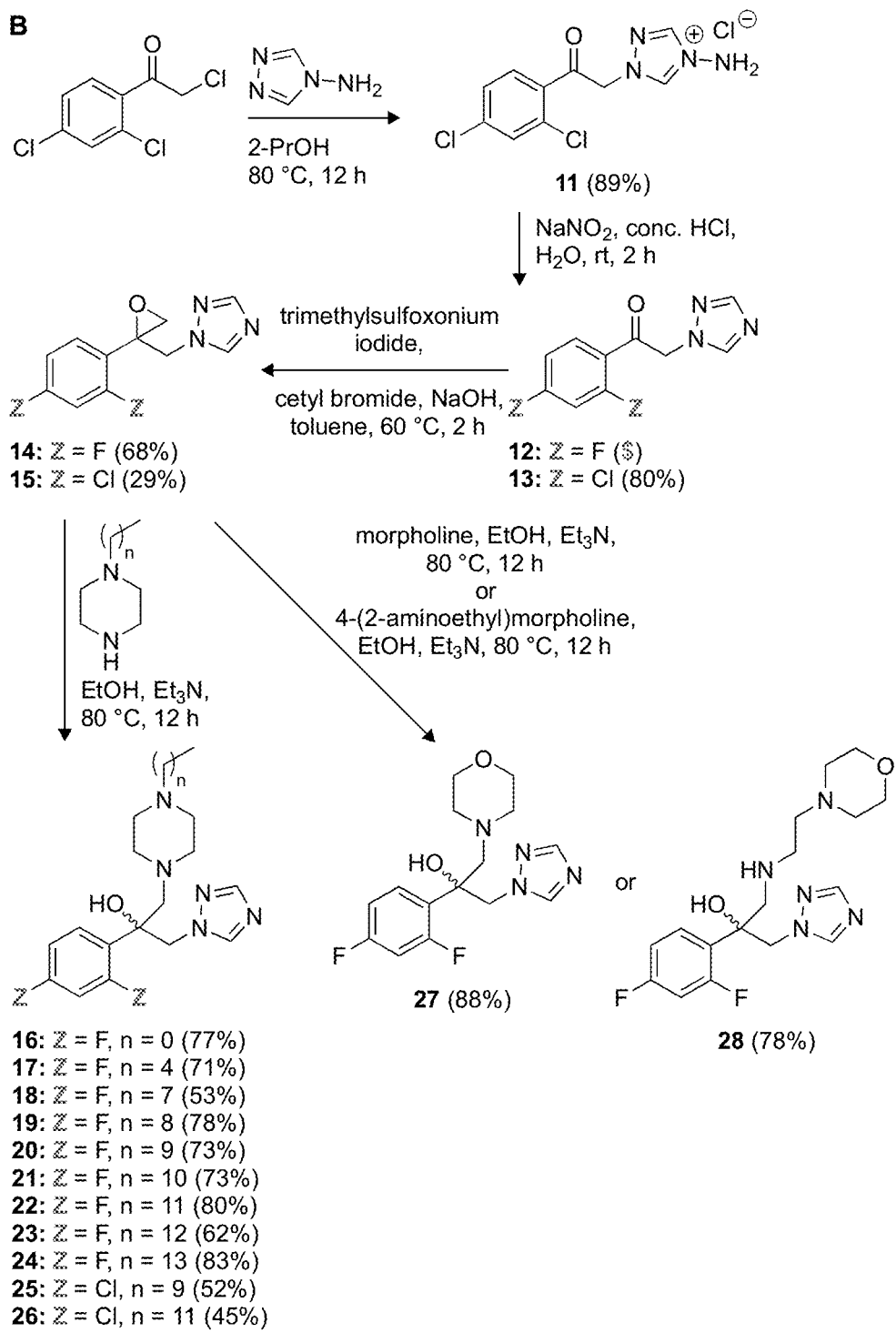
FIG. 8B is a synthetic scheme for the preparation of novel azole analogues 16-28.

Design and synthesis of two families of antifungal compounds. We synthesized the alkylated piperazine derivatives 1-9 and morpholine derivative 10 in a single step. The nucleophilic substitution reactions of piperazine and morpholine with linear alkyl chain halides generated derivatives 1-10 (FIG. 8A). The alkylated piperazines 1-9 were used in the preparation of alkylated piperazine-azole hybrids 16-26, which proceeded in two steps from either the commercially available fluorinated compound 12 or its synthesized chlorinated counterpart 13[32] (FIG. 8B). The carbonyl group of compounds 12 and 13 was first converted to an epoxide by using trimethylsulfoxonium iodide in the presence of a strong base and a surfactant to yield the oxirane intermediates 14 and 15, respectively, which were then reacted under mild basic conditions with piperazines 1-9 to afford hybrids 16-26. Two additional hybrids, 27 and 28, were also synthesized by reacting intermediate 14 with morpholine and 4-(2-aminoethyl)morpholine, respectively.

Antifungal activity in the absence or presence of serum. The antifungal activity of the newly prepared alkylated piperazine/morpholine-azole hybrids 16-28, of intermediate 14 that we used to verify that only final compounds exert antifungal activity, as well as that of alkylated piperazine/morpholine derivatives 1-10 were first evaluated against a panel of seven *C. albicans* (ATCC 10231 (A), ATCC 64124 (R) (B), ATCC MYA-2876(S) (C), ATCC 90819(R) (D), ATCC MYA-2310(S) (E), ATCC MYA-1237(R) (F), and ATCC MYA-1003(R) (G)), three non-*albicans Candida* (*C. glabrata* ATCC 2001 (H), *C. krusei* ATCC 6258 (I), and *C. parapsilosis* ATCC 22019 (J)), and three *Aspergillus* (*A. flavus* ATCC MYA-3631 (K), *A. nidulans* ATCC 38163 (L), and *A. terreus* ATCC MYA-3633 (M)) strains using a concentration range of 0.03-31.3 µg/mL (Table 2).

TABLE 2

MIC values[a] (in µg/mL) (Note: MIC values in micromolar are presented in parentheses) determined for compounds 1-10, 14, and 16-28, as well as for four control antifungal agents (AmB, CAS, FLC, and VOR) against various yeast strains and filamentous fungi.

| Cpd # | Yeast strains | | | | | | |
|---|---|---|---|---|---|---|---|
| | A | B | C | D | E | F | G |
| 1 | >31.3 | >31.3 | >31.3 | >31.3 | >31.3 | >31.3 | >31.3 |
| | (>312.5) | (>312.5) | (>312.5) | (>312.5) | (>312.5) | (>312.5) | (>312.5) |
| 2 | >31.3 | >31.3 | >31.3 | >31.3 | >31.3 | >31.3 | >31.3 |
| | (>200.3) | (>200.3) | (>200.3) | (>200.3) | (>200.3) | (>200.3) | (>200.3) |
| 3 | >31.3 | >31.3 | >31.3 | >31.3 | >31.3 | >31.3 | >31.3 |
| | (>157.8) | (>157.8) | (>157.8) | (>157.8) | (>157.8) | (>157.8) | (>157.8) |
| 4 | 31.3 | >31.3 | >31.3 | 31.3 | 31.3 | 31.3 | >31.3 |
| | (147.4) | (>147.4) | (>147.4) | (147.4) | (147.4) | (147.4) | (>147.4) |
| 5 | 15.6 | 15.6 | 15.6 | 15.6 | 15.6 | 15.6 | 15.6 |
| | (68.9) | (68.9) | (68.9) | (68.9) | (68.9) | (68.9) | (68.9) |
| 6 | 7.8 | 7.8 | 15.6 | 7.8 | 7.8 | 7.8 | 15.6 |
| | (32.4) | (32.4) | (64.8) | (32.4) | (32.4) | (32.4) | (64.8) |
| 7 | 1.95 | 7.8 | 3.9 | 7.8 | 3.9 | 3.9 | 3.9 |
| | (7.7) | (30.7) | (15.3) | (30.7) | (15.3) | (15.3) | (15.3) |
| 8 | 0.975 | 0.975 | 1.95 | 0.975 | 1.95 | 1.95 | 1.95 |
| | (3.6) | (3.6) | (7.2) | (3.6) | (7.2) | (7.2) | (7.2) |
| 9 | 0.975 | 0.975 | 0.975 | 1.95 | 0.975 | 1.95 | 1.95 |
| | (3.5) | (3.5) | (3.5) | (6.9) | (3.5) | (6.9) | (6.9) |
| 10 | >31.3 | >31.3 | >31.3 | >31.3 | >31.3 | >31.3 | >31.3 |
| | (>110.4) | (>110.4) | (>110.4) | (>110.4) | (>110.4) | (>110.4) | (>110.4) |
| 14 | >31.3 | >31.3 | >31.3 | >31.3 | >31.3 | >31.3 | >31.3 |
| | (>132.0) | (>132.0) | (>132.0) | (>132.0) | (>132.0) | (>132.0) | (>132.0) |

TABLE 2-continued

MIC values[a] (in μg/mL) (Note: MIC values in micromolar are presented in parentheses) determined for compounds 1-10, 14, and 16-28, as well as for four control antifungal agents (AmB, CAS, FLC, and VOR) against various yeast strains and filamentous fungi.

| 16 | 7.8 | 31.3 | 7.8 | 31.3 | 7.8 | 31.3 | 31.3 |
|---|---|---|---|---|---|---|---|
|  | (23.1) | (92.8) | (23.1) | (92.8) | (23.1) | (92.8) | (92.8) |
| 17 | >31.3 | >31.3 | >31.3 | 31.3 | >31.3 | >31.3 | >31.3 |
|  | (>79.5) | (>79.5) | (>79.5) | (79.5) | (>79.5) | (>79.5) | (>79.5) |
| 18 | 3.9 | 31.3 | 31.3 | 15.6 | >31.3 | 31.3 | 0.975-31.3 |
|  | (9.0) | (71.9) | (71.9) | (35.8) | (>71.9) | (71.9) | (2.2-71.9) |
| 19 | 0.975 | 7.8 | 3.9 | 7.8 | 15.6 | 15.6 | 15.6 |
|  | (2.2) | (17.6) | (8.8) | (17.6) | (35.2) | (35.2) | (35.2) |
| 20 | 0.975 | 3.9 | 7.8 | 3.9 | 7.8 | 7.8 | 3.9 |
|  | (2.1) | (8.4) | (16.8) | (8.4) | (16.8) | (16.8) | (8.4) |
| 21 | 1.95 | 15.6 | 7.8 | 15.6 | 15.6 | 15.6 | 15.6 |
|  | (4.1) | (32.8) | (16.4) | (32.8) | (32.8) | (32.8) | (32.8) |
| 22 | 1.95 | 7.8 | 3.9 | 3.9 | 7.8 | 7.8 | 15.6 |
|  | (3.9) | (15.9) | (7.9) | (7.9) | (15.9) | (15.9) | (31.7) |
| 23 | 1.95 | 7.8 | 1.95 | 1.95 | 3.9 | 3.9 | 3.9 |
|  | (3.9) | (15.4) | (3.9) | (3.9) | (7.7) | (7.7) | (7.7) |
| 24 | 1.95 | 31.3 | 7.8 | 1.95 | 3.9 | 3.9 | 1.95 |
|  | (3.8) | (60.2) | (15.0) | (3.8) | (7.5) | (7.5) | (3.8) |
| 25 | 1.95 | 15.6 | 7.8 | 3.9 | 7.8 | 7.8 | 7.8 |
|  | (3.9) | (31.4) | (15.7) | (7.9) | (15.7) | (15.7) | (15.7) |
| 26 | 1.95 | 7.8 | 3.9 | 3.9 | 3.9 | 3.9 | 1.95 |
|  | (3.7) | (14.9) | (7.4) | (7.4) | (7.4) | (7.4) | (3.7) |
| 27 | >31.3 | >31.3 | >31.3 | 3.9-31.3 | 7.8-31.3 | >31.3 | 31.3 |
|  | (>96.5) | (>96.5) | (>96.5) | (12.0-96.5) | (24.0-96.5) | (>96.5) | (96.5) |
| 28 | 31.3 | 31.3 | 31.3 | >31.3 | >31.3 | 31.3 | >31.3 |
|  | (85.2) | (85.2) | (85.2) | (85.2) | (>85.2) | (85.2) | (>85.2) |
| AmB | 3.9 | 3.9 | 1.95 | 0.975 | 1.95 | 3.9 | 3.9 |
|  | (4.2) | (4.2) | (2.1) | (1.1) | (2.1) | (4.2) | (4.2) |
| CAS | 0.975 | 0.24 | 0.06 | 0.12 | 0.12 | 0.24 | 0.48 |
|  | (0.8) | (0.2) | (0.05) | (0.1) | (0.1) | (0.2) | (0.4) |
| FLC | 62.5 | >125 | 15.6 | >125 | >125 | 62.5 | 62.5 |
|  | (204.1) | (>408.1) | (50.9) | (>408.1) | (>408.1) | (204.1) | (204.1) |
| VOR | 0.24 | 3.9 | 1.95 | 1.95 | 0.975 | 7.8 | 1.95 |
|  | (0.69) | (11.2) | (5.6) | (5.6) | (2.8) | (22.3) | (5.6) |

| | | Yeast strains | | | Filamentous fungi | | |
|---|---|---|---|---|---|---|---|
| Cpd # | | H | I | J | K | L | M |
| 1 | | >31.3 | >31.3 | >31.3 | >31.3 | >31.3 | >31.3 |
|  | | (>312.5) | (>312.5) | (>312.5) | (>312.5) | (>312.5) | (>312.5) |
| 2 | | >31.3 | >31.3 | >31.3 | >31.3 | >31.3 | >31.3 |
|  | | (>200.3) | (>200.3) | (>200.3) | (>200.3) | (>200.3) | (>200.3) |
| 3 | | >31.3 | >31.3 | >31.3 | >31.3 | >31.3 | >31.3 |
|  | | (>157.8) | (>157.8) | (>157.8) | (>157.8) | (>157.8) | (>157.8) |
| 4 | | 31.3 | 31.3 | >31.3 | 31.3 | >31.3 | >31.3 |
|  | | (147.4) | (147.4) | (>147.4) | (147.4) | (>147.4) | (>147.4) |
| 5 | | 7.8 | 7.8 | 15.6 | 31.3 | 15.6 | 15.6 |
|  | | (34.5) | (34.5) | (68.9) | (138.2) | (68.9) | (68.9) |
| 6 | | 7.8 | 7.8 | 7.8 | 31.3 | 15.6 | 15.6 |
|  | | (32.4) | (32.4) | (32.4) | (129.6) | (64.8) | (64.8) |
| 7 | | 1.95 | 1.95 | 1.95 | 3.9 | 1.95 | 7.8 |
|  | | (7.7) | (7.7) | (7.7) | (15.3) | (7.7) | (30.7) |
| 8 | | 0.48 | 0.975 | 1.9 | 1.95 | 0.975 | 1.95 |
|  | | (1.8) | (3.6) | 5(7.2) | (7.2) | (3.6) | (7.2) |
| 9 | | 0.975 | 0.975 | 0.975 | 0.975 | 0.975 | 0.975 |
|  | | (3.5) | (3.5) | (3.5) | (3.5) | (3.5) | (3.5) |
| 10 | | >31.3 | >31.3 | >31.3 | >31.3 | >31.3 | >31.3 |
|  | | (>110.4) | (>110.4) | (>110.4) | (>110.4) | (>110.4) | (>110.4) |
| 14 | | >31.3 | >31.3 | >31.3 | >31.3 | >31.3 | >31.3 |
|  | | (>132.0) | (>132.0) | (>132.0) | (>132.0) | (>132.0) | (>132.0) |
| 16 | | 31.3 | 15.6 | 0.975 | 31.3 | 0.975 | 31.3 |
|  | | (92.8) | (46.2) | (2.9) | (92.8) | (2.9) | (92.8) |
| 17 | | >31.3 | >31.3 | 15.6 | >31.3 | >31.3 | >31.3 |
|  | | (>79.5) | (>79.5) | (39.6) | (>79.5) | (>79.5) | (>79.5) |
| 18 | | 15.6 | 7.8 | 0.03 | 1.95 | 3.9 | 3.9 |
|  | | (35.8) | (17.9) | (0.1) | (4.5) | (9.0) | (9.0) |
| 19 | | 3.9 | 0.975 | 0.24 | 0.48 | 0.975 | 1.95 |
|  | | (8.8) | (202) | (0.55) | (1.1) | (2.2) | (4.4) |
| 20 | | >31.3 | 1.95 | 0.015 | 0.24 | 0.975 | 0.975 |
|  | | (>67.5) | (4.2) | (0.03) | (0.5) | (2.1) | (2.1) |
| 21 | | 3.9 | 1.95 | 0.24 | 1.95 | 1.95 | 1.95 |
|  | | (8.2) | (4.1) | (0.50) | (4.1) | (4.1) | (4.1) |
| 22 | | 0.975 | 0.48 | 0.015 | 1.95 | 3.9 | 3.9 |
|  | | (2.0) | (0.98) | (0.03) | (3.9) | (7.9) | (7.9) |

TABLE 2-continued

MIC values[a] (in μg/mL) (Note: MIC values in micromolar are presented in parentheses) determined for compounds 1-10, 14, and 16-28, as well as for four control antifungal agents (AmB, CAS, FLC, and VOR) against various yeast strains and filamentous fungi.

| | | | | | | |
|---|---|---|---|---|---|---|
| 23 | 0.975 | 0.975 | <0.24 | 0.975 | 0.975 | 0.975 |
| | (1.9) | (1.9) | (<0.47) | (1.9) | (1.9) | (1.9) |
| 24 | >31.3 | 0.975 | >31.3 | 0.48 | 1.95 | 0.975 |
| | (>60.2) | (1.9) | (>60.2) | (0.9) | (3.8) | (1.9) |
| 25 | 0.975 | 1.95 | 0.24 | 3.9 | 3.9 | 3.9 |
| | (2.0) | (3.9) | (0.48) | (7.9) | (7.9) | (7.9) |
| 26 | 0.975 | 1.95 | 0.24 | 3.9 | 1.95 | 1.95 |
| | (1.9) | (3.7) | (0.46) | (7.4) | (3.7) | (3.7) |
| 27 | 31.3 | >31.3 | 31.3 | 7.8 | 1.95 | 15.6 |
| | (96.5) | (>96.5) | (>96.5) | (24.0) | (6.0) | (48.1) |
| 28 | 31.3 | >31.3 | 31.3 | >31.3 | >31.3 | >31.3 |
| | (85.2) | (>85.2) | (85.2) | (>85.2) | (>85.2) | (>85.2) |
| AmB | 1.95 | 3.9 | 1.95 | 15.6 | 3.9 | 3.9 |
| | (2.1) | (4.2) | (2.1) | (15.6) | (4.2) | (4.2) |
| CAS | 0.06 | 0.48 | 1.95 | >31.3 | >31.3 | >31.3 |
| | (0.05) | (0.4) | (1.6) | (>25.8) | (>25.8) | (>25.8) |
| FLC | >31.3 | >31.3 | 1.95 | 62.5 | 62.5 | 62.5 |
| | (>102.2) | (>102.2) | (6.4) | (204.1) | (204.1) | (204.1) |
| VOR | 0.06 | 0.12 | <0.03 | 0.24 | 0.12 | 0.12 |
| | (0.17) | (0.34) | (<0.06) | (0.69) | (0.34) | (0.34) |

Yeast strains: A = *Candida albicans* ATCC 10231, B = *C. albicans* ATCC 64124(R), C = *C. albicans* ATCC MYA-2876(S), D = *C. albicans* ATCC 90819(R), E = *C. albicans* ATCC MYA-2310(S), F = *C. albicans* ATCC MYA-1237(R), G = *C albicans* ATCC MYA-1003(R), H = *Candida glabrata* ATCC 2001, I = *Candida krusei* ATCC 6258, J = *Candida parapsilosis* ATCC 22019.
NOTE:
Here, the (S) and (R) indicate that ATCC reports these strains to be susceptible (S) and resistant (R) to ITC and FLC.
Filamentous fungi: K = *Aspergillus flavus* ATCC MYA-3631, L = *Aspergillus nidulans* ATCC 38163, M = *Aspergillus terreus* ATCC MYA-3633.
Known antifungal agents: AmB = amphotericin B, FLC = fluconazole, VOR = voriconazole.
[a]For yeast strains: MIC-0 values are reported for FLC analogues 1-10, 14, 16-28, AmB and CAS, whereas MIC-2 values are reported for FLC and VOR.
[a]For filamentous fungi (strains K-M), MIC-0 values are reported for all compounds.

Commercially available antifungal agents such as AmB, CAS, FLC, and VOR were used as positive controls for comparison. For final compounds 1-10 and 16-28, intermediate 14, as well as the reference drugs AmB and CAS, we reported MIC-0 values, which correspond to no visible growth of the thirteen fungal strains tested. We reported MIC-2 values (i.e., 50% growth inhibition) for FLC and VOR against all fungal strains tested with the exception of strain A by VOR. Out of the seven *C. albicans* strains; two were classified as sensitive (strains C and E), one as intermediate (strain A), and four as resistant (strains B, D, F, and G) against FLC and ITC as defined by American Type Culture Collection (ATCC). Henceforth, we define antifungal activity as excellent (0.03-1.95 μg/mL), good (3.9 μg/mL), moderate (7.8-15.6 μg/mL), or poor (≥31.3 μg/mL) based on MIC values. It is important to note that all comparisons to follow will be done by using the MIC values reported in μg/mL as the data were collected that way. However, we also present in parentheses in Table 2 the corresponding values in micromolar.

From a quick glance at the MIC data reported in Table 2, we could rapidly make the following observations. The inactivity of 14 confirmed that the intermediates generated during the synthesis of our target compounds did not exert any antifungal activity. In the case of the alkylated piperazines, the longer chains displayed better antifungal activity. Compounds 1-4 displayed poor activity against all fungal strains tested. Compounds 5 and 6 were found to be moderately active against all strains tested, with the exception of *Aspergillus flavus* (strain K). Compound 7 was found to display good activity against five (strains A, C, and E-G) of the seven *C. albicans* strains tested, all three non-*albicans Candida* (strains H-J), and two (strains K and L) of the three *Aspergillus* strains tested. Among the alkylated piperazines, compounds 8 and 9 were found to be the best. It exhibited an excellent and broad spectrum of activity. Surprisingly, the corresponding morpholine analogue of 9, compound 10, displayed poor activity against all of the tested strains.

Overall, we found the morpholine-azole hybrids 27 and 28 to be inactive as antifungal agents, with the exception of compound 27 against strains K (7.8 μg/mL) and L (1.95 μg/mL). In general, for the alkylated piperazine-azole hybrids 16-26, we observed better activity against non-*albicans Candida* and *Aspergillus* strains than against *C. albicans*. Overall, compounds 20-26 displayed good to excellent antifungal activity against most strains tested. Compounds 16 and 18, although generally not as efficient as 20-26, also displayed good to excellent activity against a few fungal strains. However, compound 17 was found to basically be inactive against all fungal strains tested.

When focusing on *Aspergillus* strains, we observed that compounds 19-21, 23, and 24 displayed excellent activity against strains K-M. Compounds 18, 22, 25, and 26 were good against strains K-M, whereas compounds 16 and 17 were completely inactive, with the exception of compound 16 against strain L (0.975 μg/mL). When looking at the non-*albicans Candida*, we found that the three strains tested were susceptible to the majority of the alkylated piperazine-azole hybrids, with strain J being the most susceptible. Indeed, compounds 16, 18-23, 25, and 26 showed excellent activity against strain J. In most cases, compounds 18-26 displayed moderate to excellent activity against strains H and I. When examining the MIC values against *C. albicans* strains A-G, we observed that compounds 19-26 exhibited good to moderate activity, whereas compounds 16-18 generally displayed poor activity. From all of these observations made on compounds 1-28, we can conclude that compounds 7-9, 20, 22, 23, 25, and 26 displayed better overall activity. It is important to point out that these compounds maintained activity against the azole-resistant *C. albicans* strains.

As it is known that some of the azole antifungals on the market tend to bind to proteins and be less efficient in intracellular matrices, we tested the best compounds 7, 9, 20, 22, 25, and 26 against strains A, J, and L in presence and absence of fetal bovine serum (FBS) (Table 2), in order to test the potential effect of protein binding to our compounds. We found that the alkylated piperazine-azole hybrids 20, 22, 25, and 26 retained their full antifungal activity in the presence of FBS, whereas the alkylated piperazine derivatives 7 and 9 exhibited a 2 to 8-fold decrease in activity in the presence of this agent. It is important to note that even with this small loss in activity, compounds 7 and 9 remained good antifungals.

Structure-activity-relationship (sar) summary. From a deeper analysis of the antifungal MIC data (Table 2), we could answer the five following questions: (i) Which chain length confers better activity to the alkylated piperazine derivatives 1-9? (ii) Which chain length confers superior activity to the alkylated piperazine-azole hybrids 16-26? (iii) Which scaffold (alkylated piperazine versus alkylated piperazine-azole hybrid) produces the best antifungal activity? (iv) Does the identity of the halogen atoms on the phenyl ring play a role in antifungal activity? (v) How do the compounds generated compare to antifungals currently used in the clinic?

For the alkylated piperazine derivatives 1-9, the optimal chain lengths for maximal activity were found to be $C_{14}$, $C_{13}$, and $C_{12}$, and the general trend for activity versus chain length was $C_{14}=C_{13}>C_{12}>C_{10}>C_9=C_8=C_5=C_1$. For the alkylated piperazine-azole hybrids 16-26, the optimal chain lengths were found to be $C_{13}$, $C_{12}$, and $C_{10}$, and the general trend for activity versus chain length was $C_{13}>C_{12}>C_{10}>C_{14}>C_{11}>C_9>C_8>C_1>C_5$. By performing pairwise comparisons of the activity of alkylated piperazine derivatives 1-9 to that of their direct azole hybrid counterparts 16-24 (e.g., 1 versus 16, 2 versus 17, etc), we determined that the hybrids conferred superior antifungal activity, with the exception of compounds 8 and 9, which displayed overall superior antifungal activity than hybrids 23 and 24. By investigating the activity of the dichlorinated hybrids 25 and 26, and comparing them to those of the difluorinated counterpart 20 and 22, respectively, we observed that the identity of the halogen atoms on the phenyl ring did not greatly influence the antifungal activity of the compounds. For the $C_{10}$-containing hybrids (20 and 25) a slightly superior activity was observed with the difluorinated compound 20, whereas for $C_{12}$-containing hybrids (22 and 26) comparable antifungal activity was observed with both compounds against all strains tested. In general, we found that the most potent antifungal compounds synthesized (7-9, 20, 22, 23, 25, and 26) displayed better activity than FLC and similar or better activity than AmB against all fungal strains tested, as well as better activity than CAS against the three *Aspergillus* strains tested. For the reminder of the study, we decided to use active compounds with alkyl chains containing an even number carbons are representatives.

Antibiofilm activity of synthetic compounds. Biofilms are complex functional communities of one or more species of microorganisms that are encased in extracellular polymeric substances and attached to both a solid surface and to each other. Being complex matrices, antifungal agents have difficulty reaching the pathogens embedded in these difficult-to-treat networks. The antibiofilm activity of compounds 7, 9, 20, 22, 25, and 26, as well as that of VOR were evaluated against biofilms of *C. albicans* ATCC 64124 (strain B) by XTT reduction assay (Table 4).

TABLE 4

Antibiofilm activity of compounds 5, 6, 16, 17, 19, and 20, as well as VOR against *C. albicans* ATCC 64124 (strain B) biofilms.

| Cpd # | SMIC$_{50}$ (µg/mL) | SMIC$_{80}$ (µg/mL) |
| --- | --- | --- |
| 5 | 7.8 | 31.3 |
| 6 | 15.6 | 62.5 |
| 16 | 15.6 | 62.5 |
| 17 | 7.8 | 15.6 |
| 19 | 15.6 | 31.3 |
| 20 | 15.6 | 31.3 |
| VOR | 62.5 | 62.5 |

SMIC$_{50}$ = sessile minimum inhibitory concentration that reduced the metabolic activity of biofilms by 50%.
SMIC$_{80}$ = sessile minimum inhibitory concentration that reduced the metabolic activity of biofilms by 80%.

The SMIC$_{50}$ and SMIC$_{80}$ values (SMIC$_{50}$ and SMIC$_{80}$ are defined as the drug concentration required to inhibit the metabolic activity of the biofilm by 50% and 80%, respectively) for all tested compounds ranged between 7.8-15.6 µg/mL and 31.3-62.5 µg/mL, respectively, and were both 62.5 µg/mL for VOR, indicating the superiority of the alkylated piperazine-azole hybrids as *C. albicans* antibiofilm agents. Although it has been reported that *Candida* biofilms can exhibit higher degree of resistance (with 30 to 2,000-times higher MIC values than their corresponding planktonic MIC values) to current antifungals such as AmB and azoles,[33] we found the MIC values of alkylated piperazine-azole hybrids to not be greatly affected in biofilms. By comparing the SMIC$_{50}$ and SMIC$_{80}$ values to the MIC values in liquid cultures for each compound, we found that compounds worked best in biofilms in the following order: 22 and 25 (0 to 2-fold increase in MIC in biofilms)>7 (1 to 4-fold increase)>26 (2 to 4-fold increase)>20 (4 to 16-fold increase)>9 (16 to 64-fold increase). Our results suggested that all hybrids tested, with the exception of 9, could eliminate pre-formed biofilms of *C. albicans* ATCC 64124 (strain B), at least in vitro.

Figures 9A, 9B, 9C, 9D:
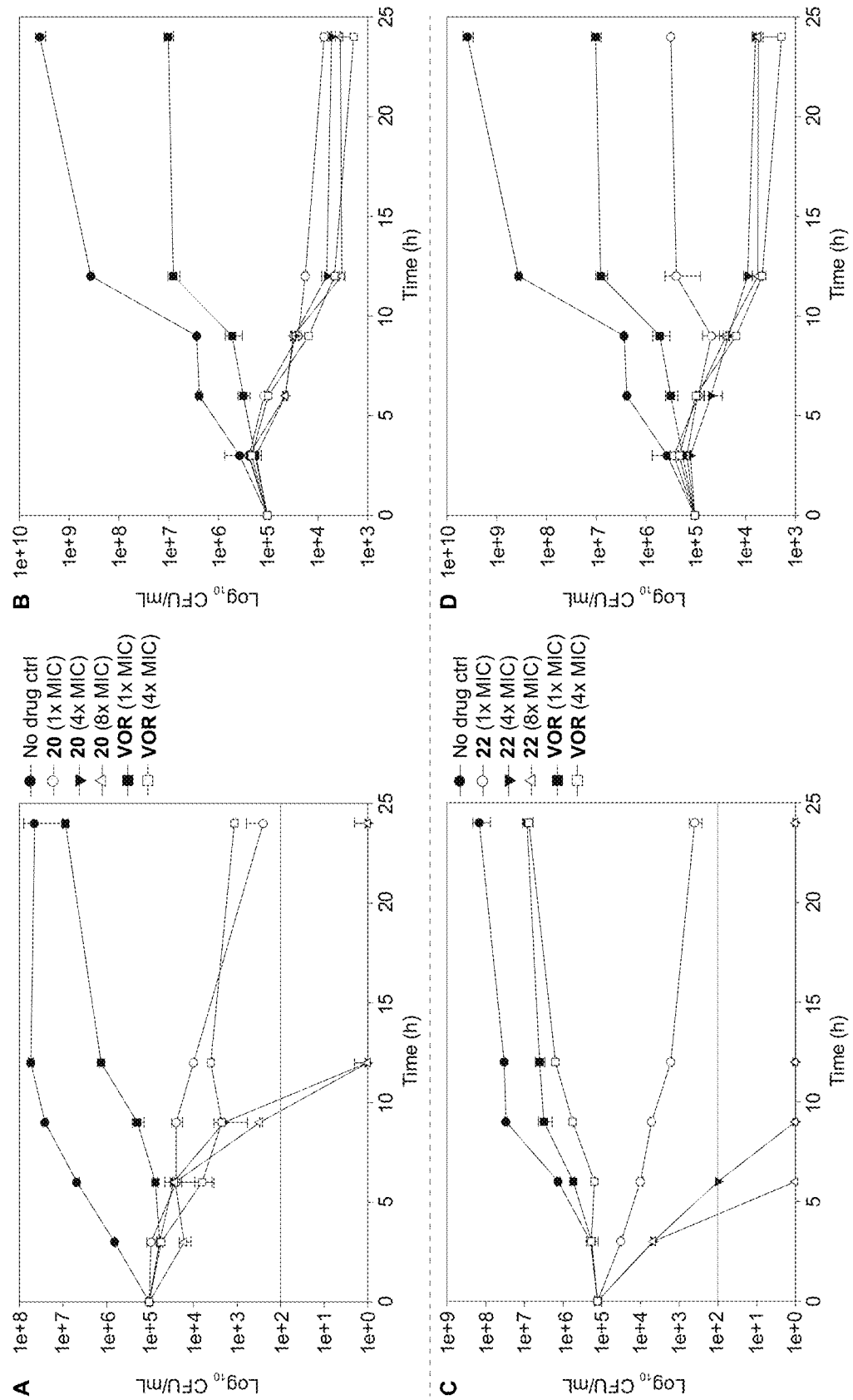
FIG. 9A-9D include Representative time-kill curves for compound 20 against FIG. 9A. C. albicans ATCC 10231 (strain A) and FIG. 9B. C. parapsilosis ATCC 22019 (strain J), as well as for compound 22 against FIG. 9C. C. glabrata ATCC 2001 (strain H), and FIG. 9D. strain J. Fungal strains were treated with no drug (black circles), 1×MIC (white circles), 4×MIC (inverted black triangles), or 8×MIC (white triangles) of compounds 20 or 22, or with 1×MIC (black squares) or 4×MIC (white squares) of VOR. The detection limit of this assay was 100 CFU/mL (represented by the red line in panels A and C).

Time-kill assays. To determine if the antifungal activity of the alkylated piperazine-azole hybrids is fungistatic or fungicidal, we performed time-kill assays over 24-hour periods by using compounds 20 and 22, each against two fungal strains (strains A and J for 20; H and J for 22) (FIG. 9). We found compounds 20 and 22 to be fungicidal at 4× their respective MIC values against strains A and H, respectively. With their fungicidal activity, compounds 20 and 22 appear to be better antifungals than the control FDA-approved drug VOR, which displayed fungistatic activity against these two fungal strains. However, when tested against strain J, both compounds displayed fungistatic activity at up to 8× their MIC values. Although fungistatic against strain J, at 1× their respective MIC values, compounds 20 and 22 displayed a larger reduction in fungal growth than VOR, confirming their superiority as antifungals.

Hemolysis assay. Since our synthetic hybrids exhibited promising antifungal activity, we wanted to confirm that they would display none or reasonable (<50% hemolysis at 10×MIC) hemolytic activity against murine red blood cells (mRBCs). We first investigated the alkylated piperazine derivatives 7 and 9 and found them to exhibit 52% and 93% hemolysis of mRBCs at 7.8 µg/mL (1 to 8-fold higher concentration than their overall antifungal MIC values), potentially indicating that very long alkyl chains might not be optimal for the development of these compounds as antifungals. We next tested all of the alkylated piperazine-azole hybrids generated, with the exception of compound 17 that we had found to be inactive. Compounds 16 ($C_1$) and 18

($C_8$) displayed <10% hemolysis at a concentration 62.5 µg/mL, which is 2 to 1024-fold higher than their overall MIC values. Similarly, compound 20 induced only 23% lysis at 31.3 µg/mL, which is 1 to 1024-fold higher than the MIC values reported for this compound. Since compound 20 is one of the best molecules in terms of MIC values, the low hemolytic activity for this analogue is highly encouraging. However, similarly to their counterparts 7 and 9, hybrids 22 and 24 with $C_{12}$ and $C_{14}$ alkyl chains were found to display >50% hemolysis at 7.8 µg/mL, confirming that very long alkyl chains are not optimal. Subsequently, we analyzed the hemolytic activity of the dichlorinated compounds 25 and 26 and compared them with their difluorinated counterparts 20 and 22. Similarly to compounds 20 and 22, hybrids 25 and 26 showed chain-dependent hemolytic activity in the order of 26 ($C_{12}$)>25 ($C_{10}$). Compound 25 showed only 22% hemolysis at 7.8 µg/mL (1 to 65-fold higher concentration than its antifungal MIC values). However, at that same concentration of 7.8 µg/mL, compound 26 displayed 85% hemolysis of mRBCs. Overall, the difluorinated analogues 20 and 22 displayed lower or equal hemolytic activity when compared to their dichlorinated counterparts 25 and 26. Importantly, the newly synthesized compound 20 displayed less hemolytic effect than the FDA-approved control drug VOR.

Figure 10:
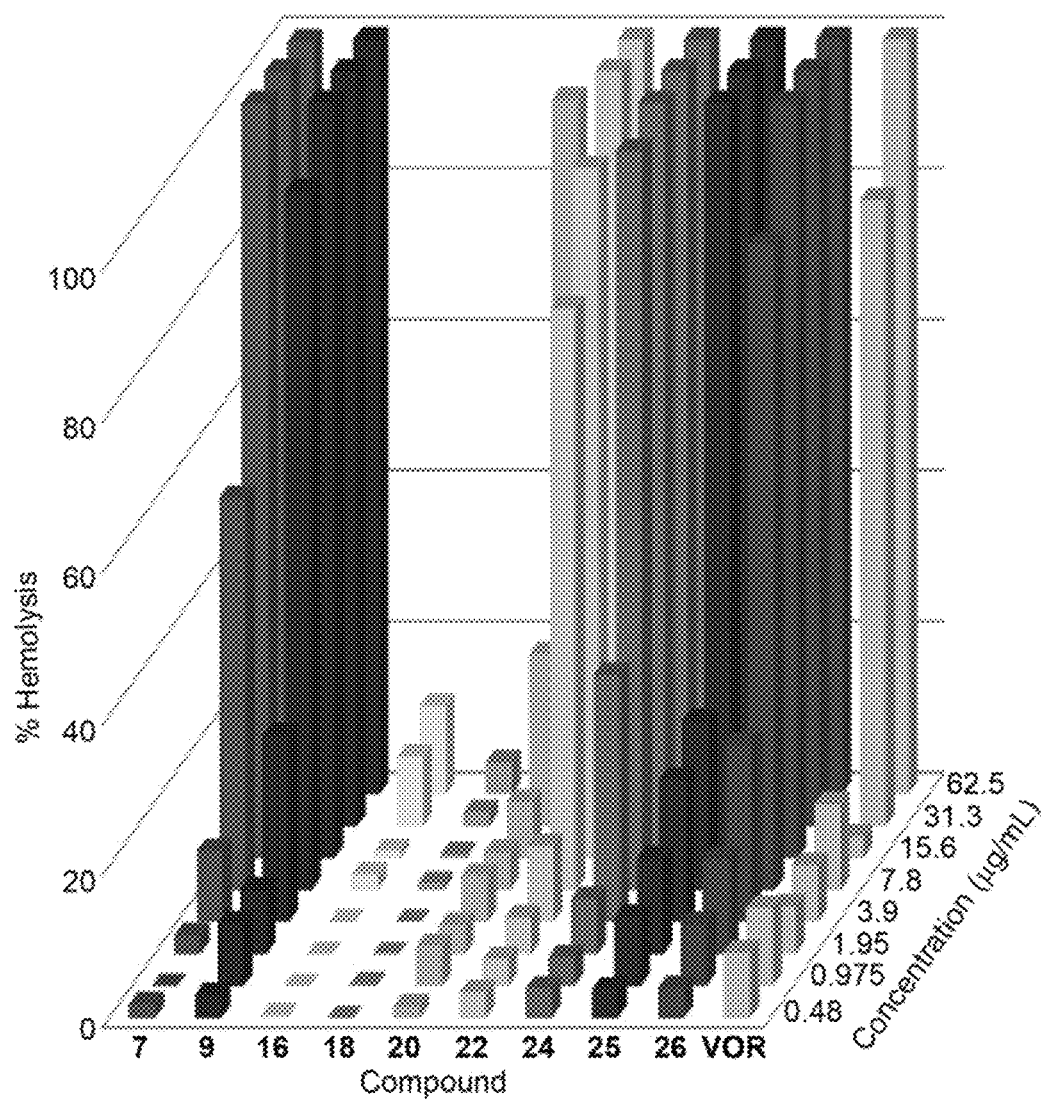
FIG. 10 is a 3D bar graph depicting the dose-dependent hemolytic activity of azole derivatives against mouse erythrocytes. Mouse erythrocytes were treated and incubated for 1 h at 37° C. with compounds 7, 9, 16, 18, 20, 22, and 24-26, and VOR at concentrations ranging from 0.48-62.5 μg/mL. Triton X-100® (1% v/v) was used as a positive control (100% hemolysis, not shown).
Figures 11A, 11B, 11C:
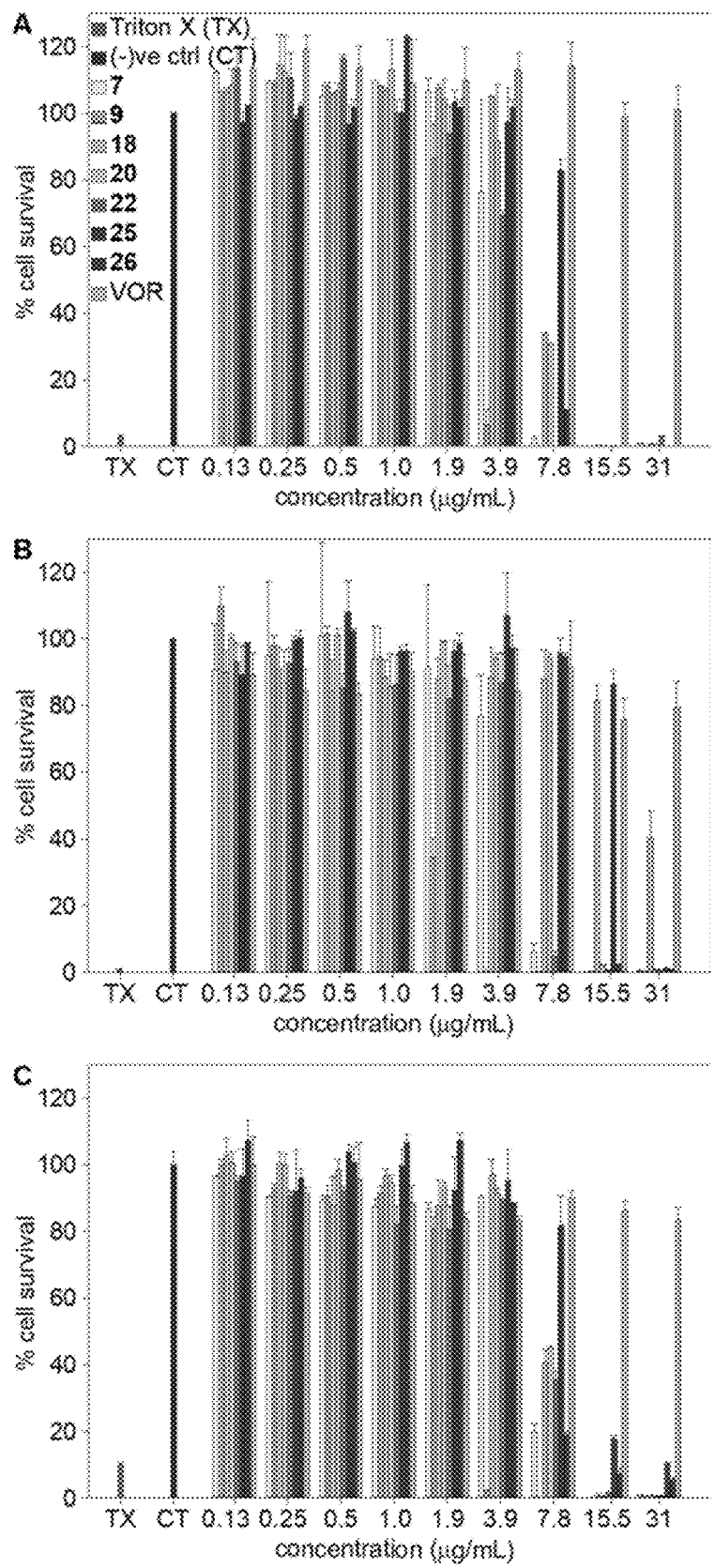
FIG. 11A-11B includes representative cytotoxicity assays of piperazine and azole analogues against three mammalian cell lines.

In vitro cytotoxicity assay. Since fungi are eukaryotes with similar biological properties, the drugs that are designed to target fungal cells may cause unwanted toxicity to mammalian cells. Therefore, a crucial parameter to consider when developing antifungal drugs is their selectivity for fungal over mammalian cells. To determine the selectivity of the synthetic hybrids towards fungi, we tested the most active compounds 7, 9, 18, 20, 22, 25, and 26 against three different cell lines, HEK-293, A549, and BEAS-2B, along with the FDA-approved antifungal agent VOR as a positive control (FIG. 10). We observed that the alkylated piperazine derivatives 7 and 9 were toxic to all three cell lines tested, with the longer alkyl chains resulting in higher toxicity to mammalian cells. Compound 18 ($C_8$) was non-toxic to A549 at up to 15.5 µg/mL, but exhibited some toxicity against HEK-293 and BEAS-2B at 7.8 µg/mL (1 to 1024-fold higher concentration than its overall antifungal MIC values). Similarly, hybrid 20 displayed no toxicity at up to 7.8 µg/mL against A549, and also exhibited some toxicity against HEK-293 and BEAS-2B at 7.8 µg/mL, which is 1 to 2048-fold higher than the MIC values reported for this compound. As we postulated, for compound 22 with the longer alkyl chain, less than 40% cell survival was reported against all three cell lines when tested at a concentration of 7.8 µg/mL (1 to 2048-fold higher concentration than its overall antifungal MIC values). The dichlorinated compounds 25 and 26 exhibited similar trends and the cytotoxicity values were 1 to 128-fold higher concentration than the overall antifungal MIC values reported for these compounds. Overall, when considering the very low MIC values for hybrids 18, 20, 22, 25, and 26 against specific fungal strains, these cytotoxicity data are encouraging.

Figure 12:
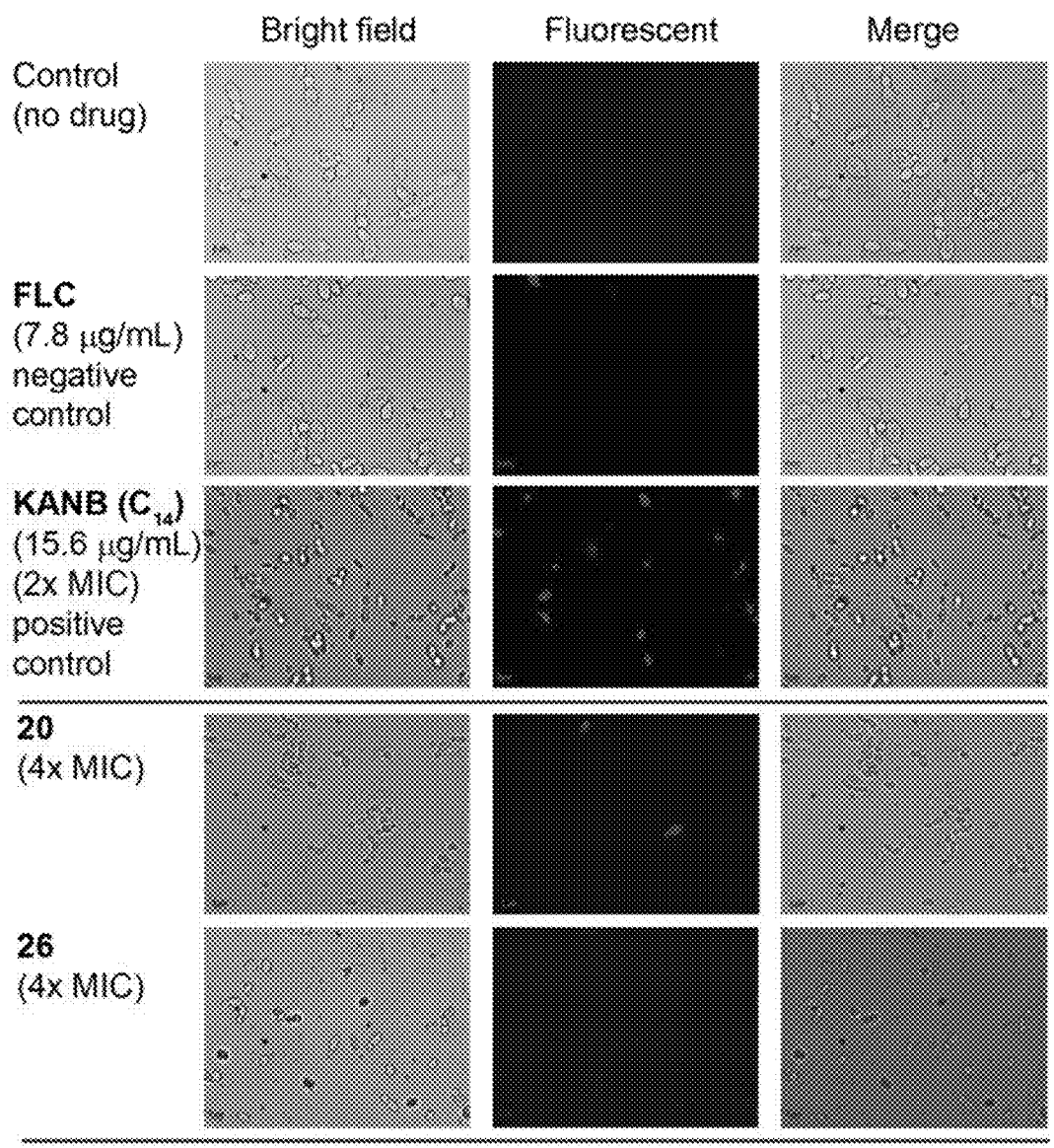
FIG. 12 shows Effect of FLC and compounds 20 and 26 on the cell membrane integrity of C. albicans ATCC 10231 (strain A). From the top to bottom: Propidium iodide (PI) dye uptake by yeast cells without drug, with FLC (7.8 μg/mL), KANB ($C_{14}$) (15.6 μg/mL), compound 20 (4×MIC), and compound 26 (4×MIC).

Membrane permeabilization assay. Previous studies from our group have demonstrated that amphiphilic molecules can cause membrane disruption to result in fungal cell death. Based on these findings, we assumed that the hybrids generated in this study could also potentially cause fungal death by disrupting the fungal membrane. To investigate this possible mechanism of action, we evaluated the effect of compounds 20 and 26 on fungal cell membrane integrity by using propidium iodide (PI) dye as a probe (FIG. 12). The PI dye can only enter the cells with compromised membrane. Afterwards, the dye binds to nucleic acid and fluoresces, which can be observed under a fluorescence microscope. We used compounds 20 and 26 with $C_{10}$ and $C_{12}$ linear alkyl chains to determine the impact of chain length on membrane disruption. The KANB ($C_{14}$) derivative with a 14-carbon linear alkyl chain, and FLC were used as positive and negative controls, respectively. At 2×MIC, the positive control KANB ($C_{14}$) significantly increased PI dye uptake by C. albicans ATCC 10231 (strain A). As expected, at 7.8 µg/mL, the highest concentration achievable in this assay, the negative control FLC did not allow for PI uptake by the fungal cells. Regardless of their chain length, neither compound 20 nor 26 (at 4×MIC) induced cellular uptake of PI dye into C. albicans ATCC 10231 (strain A). From this study, we concluded that the possible mechanism of action of our compounds is not membrane disruption.

Figures 13E, 13F, 13G:
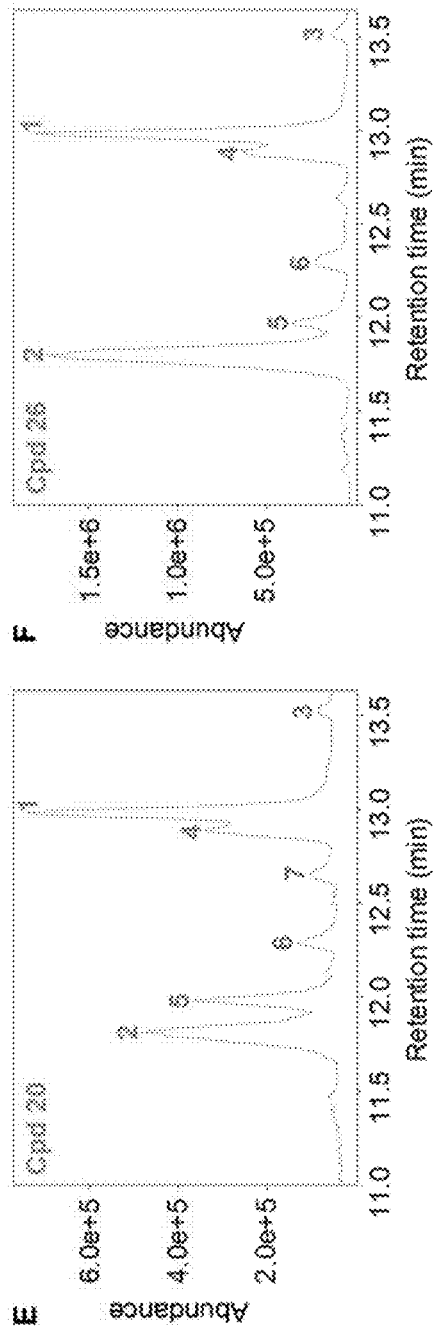

Determination of sterol composition in c. albicans in the presence and absence of drugs. Since our synthetic hybrids did not cause membrane disruption of C. albicans ATCC 10231 (strain A) in the membrane permeabilization assay, we predicted they could potentially act like the other conventional azoles, and decided to explore their effect on sterol composition. By using gas chromatography-mass spectrometry (GC-MS), we investigated the potential of the synthetic compounds to exert their antifungal activity by inhibiting the sterol 14α-demethylase enzyme of the ergosterol biosynthetic pathway (FIG. 13). We selected two of the best compounds, 20 and 26, and evaluated their effect on sterol composition in C. albicans ATCC 10231 (strain A) at sub-MIC levels of 0.48 µg/mL (FIG. 13E) and 0.975 µg/mL (FIG. 13F), respectively. We also used FLC and VOR at 1.95 µg/mL and 0.12 µg/mL, respectively, for comparison studies (FIGS. 13C and 13D). A no drug control was also performed (FIG. 13A). The sterol profile results are summarized in FIG. 13G. The sterol profile in the absence of drug indicated that strain A accumulated 100% ergosterol (2), suggesting that the sterol biosynthesis was fully functional in this fungal strain. When treated with FLC, we found predominance of ergosterol (2, 95.90%) in strain A, which indicated that FLC had no effect on ergosterol biosynthesis in this specific fungal strain. This observation could be easily explained by the fact that we have used FLC concentration that corresponds to 32-fold lower than the antifungal MIC value (62.5m/mL) for FLC against this strain. When treating strain A with VOR, we detected a lower amount of ergosterol (2, 64.93%), and an increased amount of lanosterol (1, 18.49%) and eburicol (3, 2.14%) in comparison to what we observed with FLC. However, when strain A was treated with compound 26, we observed a relatively low amount of ergosterol (2, 50.64%), as well as a higher quantity of lanosterol (1, 29.49%), eburicol (3, 1.15%), and the fungistatic metabolite 14α-methyl ergosta-8,24(28)-diene-3β,6α-diol (4, 11.05%). Interestingly, when strain A was treated with compound 20, we detected a greater reduction in the amount of ergosterol (2, 30.15%) along with a related increase in lanosterol (1, 33.37%), eburicol (3, 1.25%) and the fungistatic metabolite 14α-methyl ergosta-8,24(28)-diene-3β,6α-diol (4, 15.40%). Finally, both compounds inhibited the ergosterol biosynthesis better than the azole drug controls FLC and VOR. These results indicated that the synthetic analogues 20 and 26 act by inhibiting 14α-demethylase enzyme present fungal cells, thereby affecting the ergosterol biosynthetic pathway.

Figures 14A, 14B:
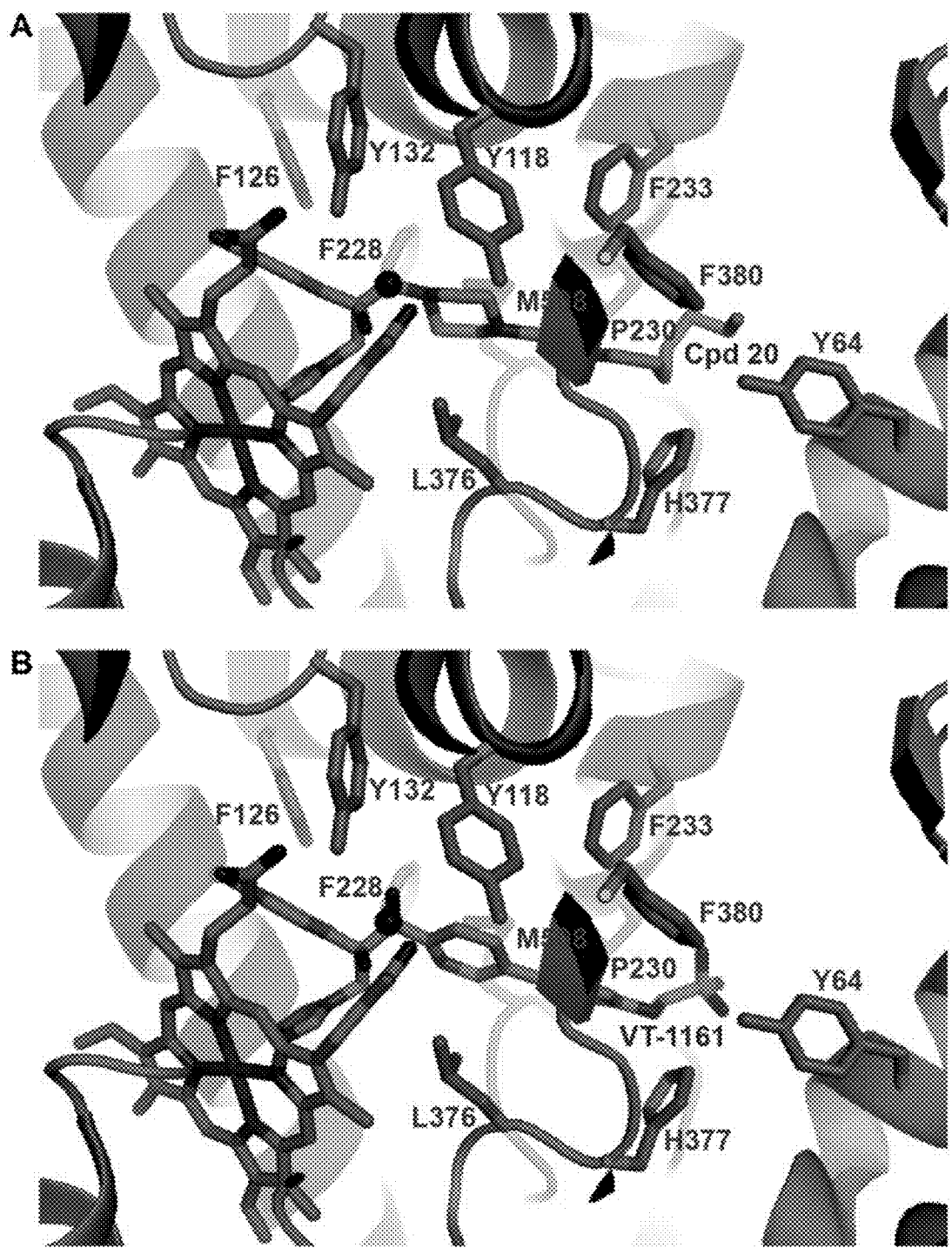
FIG. 14A. Docking of compound 20 to the C. albicans sterol 14α-demethylase CYP51 (PDB ID: 3P99[34]).
FIG. 14B. Co-crystal structure of VT-1161 bound to the C. albicans sterol 14α-demethylase CYP51 (PDB ID: 3P99[34]). In both panels the residues interacting with the bound molecules are shown as orange sticks. A water molecule is depicted as a purple sphere. The heme is shown as green sticks with its iron in dark orange. Compounds 20 and VT-1161 as depicted as turquoise sticks with their oxygen, nitrogen, and fluorine atoms in red, blue, and dark turquoise.
Figure 15:
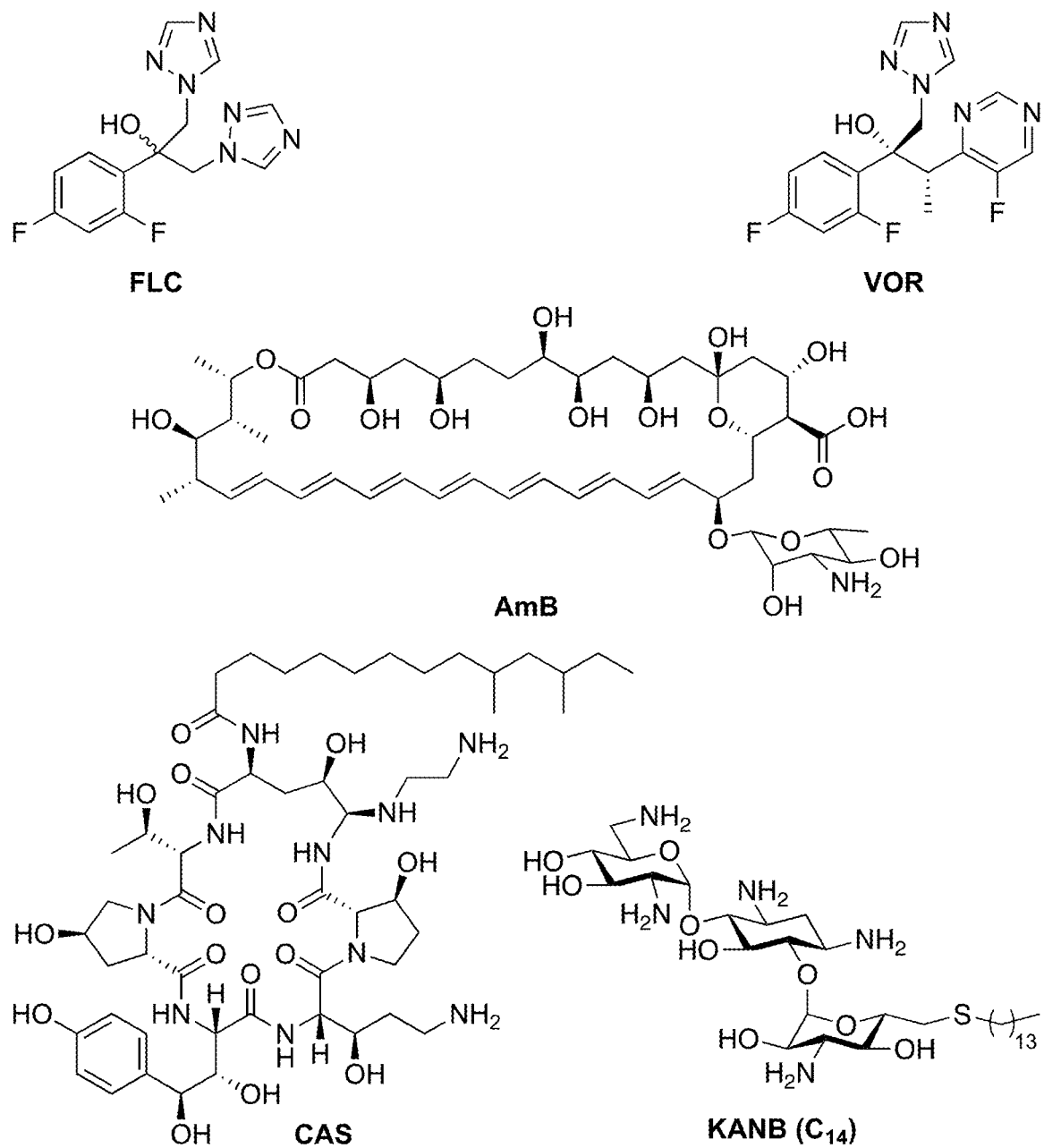
FIG. 15 Structures of all antifungal agents used as controls in this study.

Molecular docking study. To provide further confirmation of the inhibition of sterol 14α-demethylase with the new FLC derivatives, we performed docking studies of analogue 20 with the C. albicans CYP51. The synthetic analogue 20 was docked based on the crystal structure of VT-1161 with C. albicans CYP51 (PDB ID: 3P99[34]) (FIG. 14). The pharmacophore of 20 was unambiguously positioned based on VT-1161 and the rest of the molecule was positioned isosterically with the features of the inhibitor VT-1161. The difluorophenyl ring, triazole, and piperazine ring of the synthetic analogue 20 are isosteric with the difluorophenyl ring, tetrazole, and pyridine ring of VT-1161. The alkyl chain of 20 is isosteric with the 4-(2,2,2-trifluoroethoxy) phenyl ring of VT-1161. Even though the alkyl chain is longer, it fits perfectly in to the hydrophobic region. The triazole ring is coordinated to the iron (Fe) of the heme and the difluorophenyl ring is largely occupying the hydrophobic environment of Phe126, Ile131, Phe228, and on the other side Tyr132. The hydroxyl group of 20 makes water molecule mediated hydrogen bonding with the hydroxyl of Tyr132 and carboxylate group of the heme. The piperazine ring is surrounded by Leu121, Met508, and Leu376, which is favored hydrophobically. Additional hydrophobic interactions with the phenyl ring of Tyr118 was observed for the piperazine ring. Similarly to the 4-(2,2,2-trifluoroethoxy) phenyl group of VT-1161, the alkyl chain of compound 20 occupies a large solvent accessible predominantly hydrophobic pocket surrounded by Tyr64, Leu87, Leu88, Pro230, Val234, and His377. In sum, the synthetic analogue 20 exhibited many favorable interactions with the CYP51 enzyme, which further support the results observed by the determination of sterol composition experiments.

Chemical and physical properties. FLC is known for its bioavailability, but in bulk form, it appears crystalline and is only slightly soluble in water compared to organic solvents such as DMSO where it is highly soluble. Our best compounds, 7, 8, 9, 20, 22, 23, 25, and 26, displayed similar solubility behaviors to that of FLC. The Lipinski's rule of five is often used as a starting point to evaluate drug likeness or determine if a compound with a certain pharmacological or biological activity has properties that would make it a likely active drug in humans. We calculated the Log P values of all the compounds (Table S2). In general, an orally active drug is allowed no more than one violations of the rule of five. We investigated compound 7, 8, 9, 20, 22, 23, 25, and 26 for potential violations of the rule of five. In the case of the alkylated piperazines 7, 8, and 9, we observed only one violation (their Log P values was greater than 5), but their molecular weight <500, not more than 5 hydrogen bond donors, and 10 hydrogen bond acceptors were in line with the rule of five. Similar results were observed for the alkylated piperazine-azole hybrids 20, 22, 23, 25, and 26. Compounds 20, 22, 23, and 25 exhibited <500, <5 hydrogen bond donors and <10 hydrogen bond acceptors with Log P values higher than 5. Only compound 26 displayed two violations with greater than 500 molecular weight and Log P value greater than 5. From these observations, we can conclude that these compounds will be, in the future (outside the scope of this study), be investigated in animal studies.

CONCLUSION

In summary, we have synthesized nine novel alkylated piperazine derivatives (1-9) as well as eleven alkylated piperazine-azole hybrids (16-26) along with an alkylated morpholine derivative (10) and two morpholine-azole hybrids (27-28) with alkyl chains of various lengths ($C_1$, $C_5$, $C_8$-$C_{14}$). We did not detect any antifungal activities with the alkylated morpholine derivative and the two morpholine-azole hybrids. We observed that the antifungal activity of alkylated piperazines and alkylated piperazine-azole hybrids depended on the length of the alkyl chains. We identified compounds 7, 9, 20, 22, 25, and 26 as promising antifungal agents with low hemolytic activity, low cytotoxicity, and great activity against C. albicans, non-albicans Candida, and Aspergillus strains. In most cases, compounds 7-9, 20, 22, 23, 25, and 26 displayed enhanced or comparable antifungal activity against fungal strains when compared to the commercial antifungal drugs AmB, CAS, and FLC. These compounds also exhibited superior activity compared to the control drug VOR against Candida biofilms. Contrary to the mechanism of action (i.e., membrane disruption) previously reported for molecules containing long alkyl chains, the compounds in this study did not disrupt the fungal membrane. Instead, the molecules studied killed the fungal cells by disrupting ergosterol biosynthesis by targeting the sterol 14α-demethylase enzyme of the ergosterol biosynthetic pathway.

Example 3

1. This Example Relates To Generation Of Unique FLC Derivatives In Which The Triazole Ring On The Carbon Alpha To The Dihalophenyl Ring Of FLC Was Displaced By Various Linear Alkyl-, Aryl-, Dialkyl-, And Cycloalkyl-Amino Substituents.

We report the synthesis of twelve novel FLC derivatives (FIG. 16) and their antifungal activity against a variety of C. albicans, non-albicans Candida, Aspergillus, and Cryptococcus strains as established by in vitro MIC determination as well as by time-kill studies. We explore the hemolytic activity as well as cytotoxicity of these compounds against murine erythrocytes and mammalian cell lines, respectively. Finally, we investigate the potential mechanism of action of selected compounds by probing their ability to disrupt fungal membrane.

2. Results and Discussion 2.1. Design and Synthesis of Antifungal Agents 5-16.

Figures 16A, 16B:
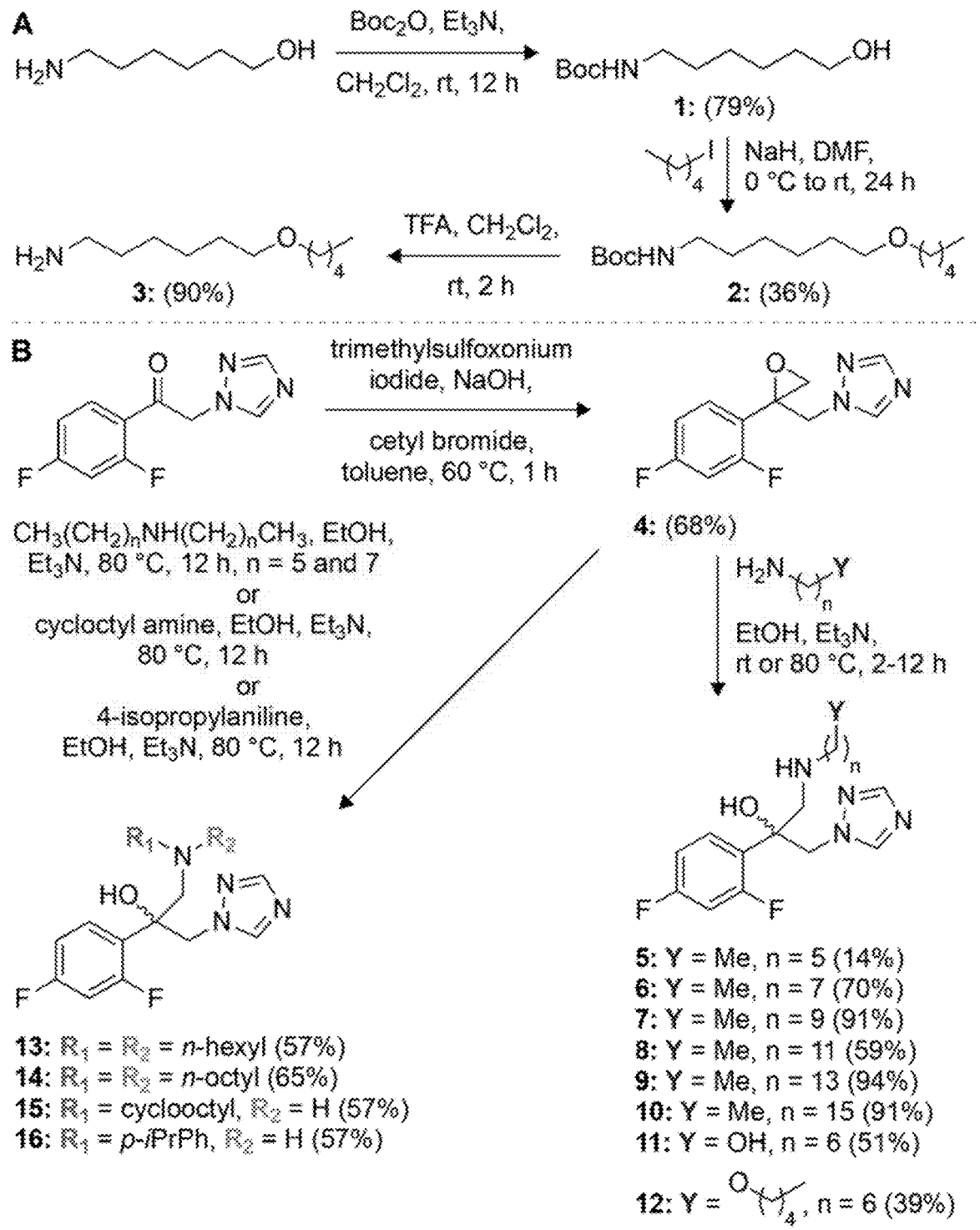
FIG. 16A Synthetic schemes for the preparation of amine derivative 3, and FIG. 16B. synthetic schemes for the preparation of novel azole analogues 5-16.

We synthesized the alkyl-/aryl- and cycloalkyl-amino FLC derivatives 5-16 in two steps by using the commercially available fluorinated compound 2,4-difuoro-2-(1H-1, 2,4-triazo-1-yl)acetophenone as a starting material (FIG. 16B). We first converted the carbonyl group of 2,4-difuoro-2-(1H-1,2,4-triazo-1-yl)acetophenone to an epoxide by using trimethylsulfoxonium iodide in the presence of a strong base and a surfactant to yield the oxirane intermediate 4, which we then reacted with various amines (all commercially available, with the exception of amine 3 used in the synthesis of derivative 12) under mild basic conditions to afford derivatives 5-16. The amine 3 used for the synthesis of derivative 12 was prepared in three steps (FIG. 16A). The amino group of 6-aminohexanol was protected with Boc to yield compound 1, which was then subjected to nucleophilic substitution reaction with 1-iodopentane. The deprotection of the Boc group of intermediate 2 yielded the desired amine 3.

2.2. Antifungal Activity and Structure-Activity-Relationship (SAR) Analysis.

We first evaluated the antifungal activity of the newly prepared FLC derivatives 5-16 against a panel of seven C. albicans (ATCC 10231 (A), ATCC 64124(R) (B), ATCC MYA-2876(S) (C), ATCC 90819(R) (D), ATCC MYA-2310 (S) (E), ATCC MYA-1237(R) (F), and ATCC MYA-1003(R) (G)), three non-*albicans Candida* (*C. glabrata* ATCC 2001 (H), *C. krusei* ATCC 6258 (I), and *C. parapsilosis* ATCC 22019 (J)), and three *Aspergillus* (*A. flavus* ATCC MYA-3631 (K), *A. nidulans* ATCC 38163 (L), and *A. terreus* ATCC MYA-3633 (M)) strains using a concentration range of 0.03-31.3 μg/mL (Tables 1 and S1). We used the commercially available antifungal agents such as AmB, caspofungin (CAS), FLC, and VOR as positive controls for comparison. For derivatives 5-16 as well as the reference drugs AmB and CAS, we reported MIC-0 values, which correspond to no visible growth. We reported MIC-2 values (i.e., 50% growth inhibition) for FLC and VOR against all fungal strains tested with the exception of strain A by VOR. We defined antifungal activity as excellent (0.03-1.95 μg/mL), good (3.9 μg/mL), moderate (7.8-15.6 μg/mL), or poor (≥31.3 μg/mL) based on MIC values. In this manuscript, we performed all activity comparisons by using the MIC values reported in μg/mL (Note: the corresponding MIC values are also provided in μM into parentheses in Tables 1, 2, S1, and S2).

By a survey of the data reported in Table 1, the following observations could rapidly be made. The introduction of a side-chain comprising (i) a terminal hydroxyl group as in compound 11, (ii) a dialkyl-amino moiety as in derivatives 13 and 14, (iii) a cycloalkyl-amino group as in compound 15, and (iv) an aryl-amino functionality as in compound 16, resulted in all cases in molecules that were generally poor antifungals. A few exceptions were noted: compounds 14 and 15 displayed excellent (0.975 μg/mL) and good (3.9 μg/mL) activity against the *C. parapsilosis* strain J. In contrary, we found that mono-alkylation resulted in much better antifungals. For derivatives 5-10, we generally observed better activity against non-*albicans Candida* and *Aspergillus* strains than against *C. albicans*. More specifically, when exploring the data for strains H-M, we found that compounds 7 and 8 displayed excellent (0.03-1.95 μg/mL) activity against the non-*albicans Candida* strains H, I, and J, as well as against the *Aspergillus* strain L. Additionally, both compounds 7 and 8 exhibited moderate (7.8 μg/mL) and good (3.9 μg/mL) activity against the *Aspergillus* strains K and M, respectively. Compounds 5, 6, 9, and 10, displayed excellent activity (0.06-1.95 μg/mL) against strains J, (I, J and L), (H and J), and (H and J), respectively. Compounds 5, 6, and 9 displayed moderate activity (7.8-15.6 μg/mL) against strains (H and I), (H and M), and M, respectively. In addition, derivatives 9 and 10 showed good (3.9 μg/mL) activity against strains I and L. When assessing the data for the *C. albicans* strains A-G, we found that compounds 6-9 exhibited excellent activity (0.48-1.95 μg/mL) against strain A. We also observed that derivatives 7 and 8 generally displayed good to moderate (3.9-15.6 μg/mL) activity against strains B-G, with the exception of compound 8 displaying excellent (1.95 μg/mL) activity against strain D. In addition, compounds 7 and 8 displayed excellent to good antifungal activity against most strains tested and derivative 9 displayed strong activity against non-*albicans Candida* and *Aspergillus* strains. These data indicated that the optimal chain lengths for maximal antifungal activity were $C_{10}$ and $C_{12}$, and the general trend for activity versus chain length was $C_{10}>C_{12}>C_8>C_{14}>C_{16}=C_6$. Finally, we observed that replacing one of the carbon atom in the side-chain by an oxygen as in compound 12 was detrimental as its activity against all strains was generally lower (higher MIC values) than that of its counterpart 8.

Having established that derivatives 5-16 displayed excellent antifungal activity against non-*albicans Candida* strains, we further evaluated these compounds against three clinical strains of *C. glabrata* (CG1, CG2, and CG3) and *C. parapsilosis* (CP1, CP2, and CP3), as well as three *Cryptococcus neoformans* (CN1, CN2, and CN3) clinical isolates (Table 2). The trends observed in Table 2 correlated perfectly to those described for the data presented in Table 1. Compounds 11 and 13 were inactive against all nine clinical isolates tested, whereas compounds 14-16 exhibited excellent to good (0.975-3.9 μg/mL) activity against *C. parapsilosis* CP1, CP2, and CP3. For derivatives 5-10, we generally observed excellent activity against most *C. glabrata*, *C. parapsilosis*, and *C. neoformans* clinical isolates. More precisely, we found that compound 8 displayed excellent (0.06-1.95 μg/mL) activity against all clinical isolates tested. Compounds 7, 9, and 10 displayed excellent (0.03-1.95 μg/mL) activity against all isolates, with the exception of *C. glabrata* CG3. In addition, compound 6 displayed excellent (0.12-1.95 μg/mL) activity against CG2, CP1, CP2, CP3, and CN1, whereas compound 5 was found to display excellent (0.975 μg/mL) activity against *C. parapsilosis* CP1, CP2, and CP3 isolates. Overall, compounds 6-10 displayed better activity against the clinical isolates presented in Table 3 than they did against the commercially available strains for which the data are presented in Table 2. In general, we found that the three most active compounds synthesized (based on the data from Tables 1 and 2), 7-9, displayed better activity than FLC and similar or better activity than AmB against most of the fungal strains tested, as well as better activity than CAS against the three *Aspergillus* strains tested. When examining the data obtained with clinical isolates of *C. glabrata*, *C. parapsilosis*, and *C. neoformans* (Table 2), we observed that compounds 7-9 displayed similar or better activity than both CAS and FLC. When comparing compounds 7-9 to VOR, we found them to display stronger activity against some of the clinical strains tested.

TABLE 3

MIC values[a] (in μg/mL) determined for compounds 7, 9, 20, 22, 25, and 26, as well as for two control antifungal agents (AmB and VOR) against various yeast strains and filamentous fungi.

| | Yeast strains | | | | Filamentous fungi | |
| --- | --- | --- | --- | --- | --- | --- |
| Cpd # | *Candida albicans* ATCC 10231 (A) (no FBS) | *Candida albicans* ATCC 10231 (A) (+10% FBS) | *Candida parapsilosis* ATCC 22019 (J) (no FBS) | *Candida parapsilosis* ATCC 22019 (J) (+10% FBS) | *Aspergillus nidulans* ATCC 38163 (L) (no FBS) | *Aspergillus nidulans* ATCC 38163 (L) (+10% FBS) |
| 7 | 1.95 | 3.9 | 1.95 | 7.8 | 1.95 | 7.8 |
| 9 | 0.975 | 7.8 | 0.975 | 7.8 | 0.975 | 7.8 |
| 20 | 0.975 | 0.975 | 0.015 | 0.06 | 0.975 | 0.975 |
| 22 | 1.95 | 1.95 | 0.015 | 0.06 | 3.9 | 3.9 |
| 25 | 1.95 | 1.95 | 0.24 | 0.24 | 3.9 | 3.9 |
| 26 | 1.95 | 1.95 | 0.24 | 0.24 | 1.95 | 3.9 |

TABLE 3-continued

MIC values[a] (in μg/mL) determined for compounds 7, 9, 20, 22, 25, and 26, as well as for two control antifungal agents (AmB and VOR) against various yeast strains and filamentous fungi.

| | Yeast strains | | | | Filamentous fungi | |
|---|---|---|---|---|---|---|
| Cpd # | Candida albicans ATCC 10231 (A) (no FBS) | Candida albicans ATCC 10231 (A) (+10% FBS) | Candida parapsilosis ATCC 22019 (J) (no FBS) | Candida parapsilosis ATCC 22019 (J) (+10% FBS) | Aspergillus nidulans ATCC 38163 (L) (no FBS) | Aspergillus nidulans ATCC 38163 (L) (+10% FBS) |
| AmB | 3.9 | 7.8 | 1.95 | 15.6 | 3.9 | 15.6 |
| VOR | 0.48 | 0.48 | 0.015 | 0.015 | 0.12 | 0.12 |

The antifungals currently on the market are known to bind to proteins and be less efficient in intracellular matrices. For this reason, we tested the three best compounds, 7-9, against three representative strains, the *C. albicans* A, the non-*albicans Candida* (*C. parapsilosis*) J, and the *Aspergillus* L, in presence and absence of fetal bovine serum (FBS) (Table 3). We found that the alkyl-amino azole analogue 7 retained its full antifungal activity (only 1 double dilution difference in some cases) against all three strains tested in the presence of FBS. Compound 8 retained its full activity against strain J and experienced a 2- and 4-fold decrease in activity in the presence of FBS against strains A and L, respectively. Compound 9 displayed a 2- to 8-fold decrease in activity against the strains tested. Even though there was a small loss in activity in some instances, analogues 7-9 still remained good antifungal with the exception of compound 9 against strain L.

2.3. Time-Kill Studies

Figures 17A, 17B, 17C, 17D:
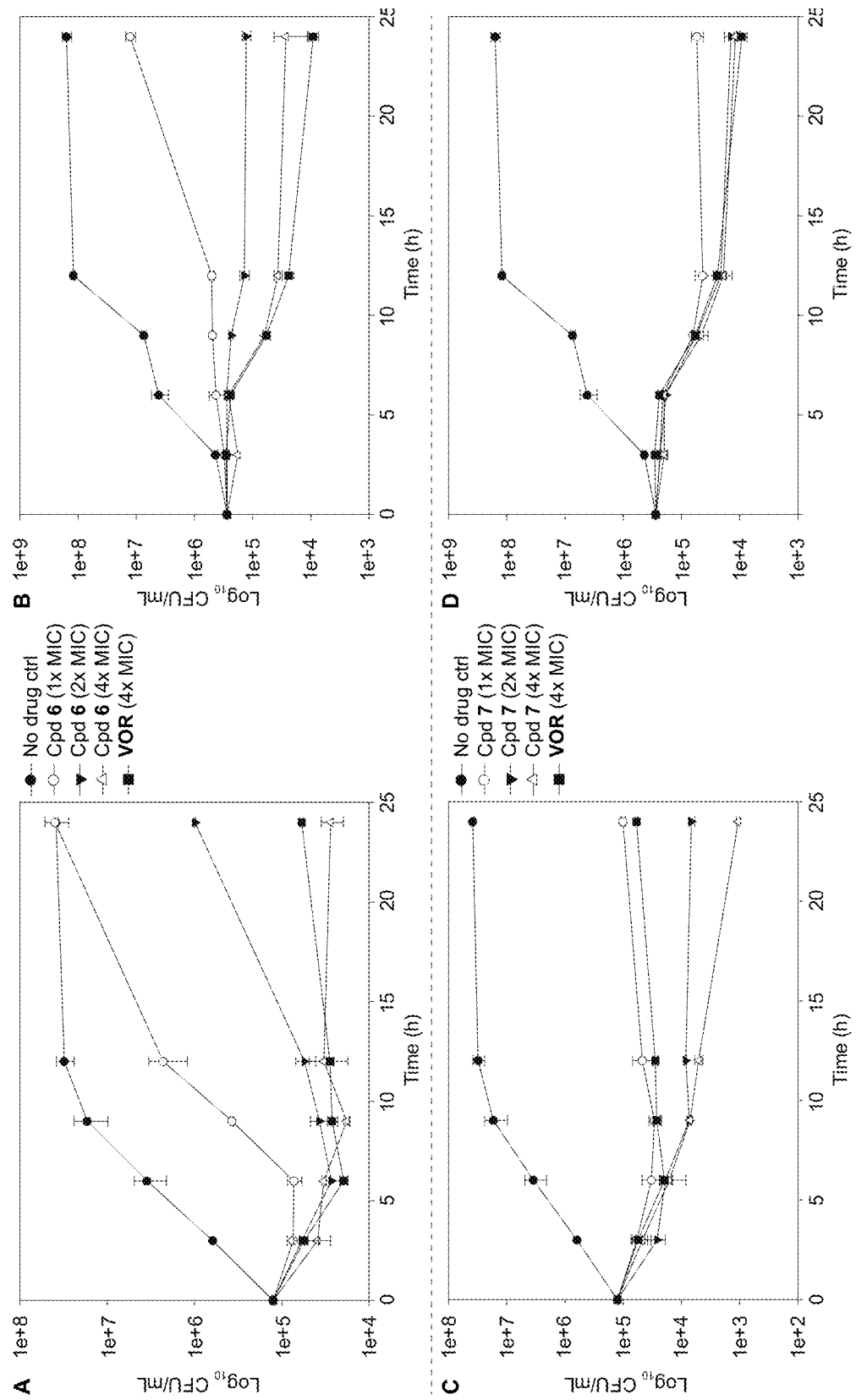
FIG. 17A-17D Representative time-kill curves for FIG. 17A compound 6 and FIG. 17C compound 7 against C. albicans ATCC 10231 (strain A) and representative time-kill curves for FIG. 17B compound 6 and FIG. 17D compound 7 against C. parapsilosis ATCC 22019 (strain J). Fungal strains were treated with no drug (black circles), 1×MIC (white circles), 2×MIC (inverted black triangles), or 4×MIC (white triangles) of compounds 6 or 7, or with 4×MIC (black squares) of VOR. The experiments were performed in duplicate.

The information regarding the rate and extend of fungicidal activity can be gathered by time-kill assays. To determine the fungistatic or fungicidal nature of the compounds generated, we performed time-kill assays over a 24-h period with one of the best FLC derivatives, compound 7, and one of the good ones, compound 6. These compounds and VOR (positive control) were tested against fungal strains *C. albicans* ATCC 10231 (A) and *C. parapsilosis* ATCC 22019 (J) (FIG. 17). At 4× their respective MIC values, when tested against strain A, compounds 6 and 7 were found to be fungistatic and to be better than the control drug VOR. When tested against strain J, both compounds also displayed fungistatic activity at up to 4× their MIC values. However, against strain J, compound 6 displayed lower reduction in fungal growth than VOR, but compound 7 displayed activity equal to VOR. Overall, the compounds 6 and 7 performed better in time-kill studies than the control drug VOR.

2.4. Hemolysis Assay

Figure 18:
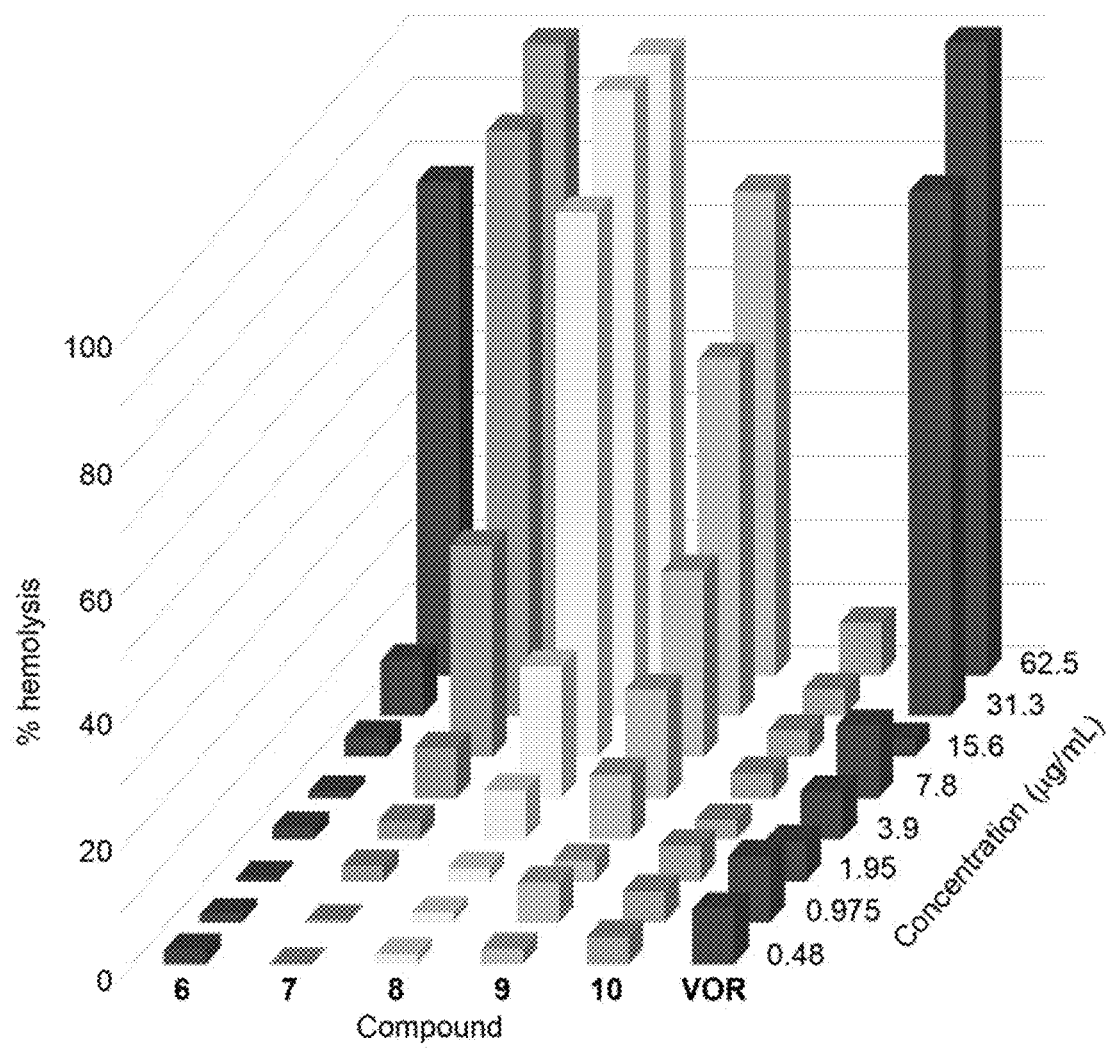
FIG. 18 includes a 3D bar graph depicting the dose-dependent hemolytic activity of azole derivatives 6-10 and VOR against mRBCs, which were treated and incubated for 1 h at 37° C. with each compound tested at concentrations ranging from 0.48-62.5 μg/mL. Triton X-100® (1% v/v) was used as a positive control (100% hemolysis, not shown).

The promising antifungal activity shown by the synthetic analogues demanded further safety analysis for these compounds. We tested compounds 6-10 for their hemolytic activity against murine red blood cells (mRBCs) (FIG. 18). Compounds 6 ($C_8$) and 7 ($C_{10}$) displayed <10% and <40% hemolysis at concentrations of 31.3 μg/mL (1- to 512-fold of its overall MIC values) and 15.6 μg/mL (1- to 512-fold of its overall MIC values), respectively. Similarly, compound 8 ($C_{12}$) induced only 21% lysis at 7.8 μg/mL (1- to 218-fold of its overall MIC values). In addition, compounds 9 ($C_{14}$) and 10 ($C_{16}$) displayed <50% and <10% hemolysis at concentrations of 31.3 μg/mL (1- to 256-fold of its overall MIC values) and 62.5 μg/mL (2- to 128-fold of its overall MIC values), respectively. By comparing the hemolysis of compounds 6-10 with their corresponding MIC values against the non-*albicans Candida, A. nidulans*, and *C. neoformans* strains tested, we concluded that all of these compounds displayed minimal hemolytic activity. Overall, compounds 6 and 10 displayed the lowest hemolytic activity. Importantly, some of the newly synthesized compounds displayed less hemolytic effect than the FDA-approved control drug VOR.

2.5. In Vitro Cytotoxicity Assay

Another crucial parameter to consider when developing antifungal drugs is their selectivity for fungal over mammalian cells. We tested our active compounds 6-10 against three different cell lines, HEK-293, BEAS-2B, and A549, along with the FDA-approved antifungal agent VOR as a positive control (FIG. 19). Against HEK-293, compounds 6, 7, and 10 exhibited no toxicity up to 31 μg/mL (1- to 512-fold of its overall MIC values), 7.8 μg/mL (1- to 256-fold of its overall MIC values), and 7.8 μg/mL (1- to 16-fold of its overall MIC values), respectively. However, compounds 8 and 9 exhibited some toxicity (>50% cell survival) at a concentration of 3.9 μg/mL (1- to 64-fold of its overall MIC values) against HEK-293. Interestingly, compounds 8-10 were non-toxic to both BEAS-2B and A549 at up to 7.8 μg/mL (1- to 128-fold of its overall MIC values). In the case of compound 6, no toxicity was observed against BEAS-2B (at 31 μg/mL) (1- to 512-fold of its overall MIC values) and A549 (at 15.5 μg/mL) (1- to 256-fold of its overall MIC values). With compound 10 we basically observed no toxicity against BEAS-2B and A549 at 7.8 μg/mL (1- to 16-fold of its overall MIC values). A general trend of greater toxicity with respect to longer chain substitution was observed against the three cell lines. Compounds 6 and 7 exhibited better overall safety profiles than compounds 8-10. When considering the very low MIC values for these analogues against clinical isolates, these cytotoxicity data provide us with a reasonable therapeutic window.

2.6. Membrane Permeabilization Assay

Some amphiphilic molecules have been shown to cause membrane disruption and fungal cell death. Therefore, we decided to study the potential effect of compounds 8 and 9 with $C_{12}$ and $C_{14}$ linear alkyl chains to determine the impact of chain length on membrane disruption (FIG. 20). The control drug VOR and the KANB ($C_{14}$) derivative with a 14-carbon linear alkyl chain, were used as negative and positive controls, respectively. The propidium iodide (PI) dye was used as a probe as it can only enter cells with compromised membrane and bind to nucleic acid to emit fluorescence, which can be observed under a fluorescence microscope. At 4×MIC, the positive control KANB ($C_{14}$) significantly increased PI dye uptake by *C. albicans* ATCC 10231 (strain A), whereas the negative control VOR (at 4×MIC) did not allow for PI uptake by fungal cells. Compound 8 with a $C_{12}$ linear alkyl chain (at 4×MIC) induced cellular uptake of PI dye into *C. albicans* ATCC 10231 (strain A), whereas compound 9 (with a $C_{14}$ linear alkyl chain) did not cause cell membrane disruption. Interestingly, the chain length played a crucial role on membrane disruption of *C. albicans* ATCC 10231 (strain A), surprisingly with $C_{12}$ being more membrane disrupting than $C_{14}$. In order to completely understand the effect of chain length on membrane disruption, we additionally performed membrane permeabilization with compounds 5, 6, and 7 ($C_6$-$C_{10}$ linear alkyl chains) at 4×MIC. None of these compounds induced cellular uptake of the PI drug. From this study, we can conclude that one of the possible mechanisms of action for compound 8 is membrane disruption. Interestingly, any other linear chains beside the $C_{12}$ displayed no membrane disruption.

2.7. Sterol Profile by GC-MS.

Since out of our compounds displaying antifungal activity only compound 8 caused membrane disruption of *C. albicans* ATCC 10231 (strain A) in the membrane permeabilization assay (section 2.6), we decided to explore by using gas chromatography-mass spectrometry (GC-MS) the effect of compounds 8 and 9 on sterol composition during ergosterol biosynthesis (the mechanism of action of other conventional azoles). We evaluated the effect of the compounds 8 and 9 on sterol composition in *C. albicans* ATCC 10231 (strain A) at sub-MIC levels of 0.48 µg/mL and 0.975 µg/mL. We also used VOR at 0.12 µg/mL and no drug control for comparison. In the absence of drug, strain A accumulated 100% ergosterol (2), suggesting that the sterol biosynthesis was fully functional in this fungal strain. When treating strain A with VOR, we detected a lower amount of ergosterol (2, 50.80%), and an increased amount of lanosterol (1, 15.21%) and eburicol (3, 1.73%). However, when strain A was treated with compound 8, we observed a relatively low amount of ergosterol (2, 36.62%) compared to VOR, but observed lower amounts of lanosterol (1, 10.03%), eburicol (3, 0.57%), and the fungistatic metabolite 14α-methyl ergosta-8,24(28)-diene-3β,6α-diol (4, 4.69%) with respect to VOR. Interestingly, when strain A was treated with compound 9, we observed similar reduction in the amount of ergosterol (2, 36.43%) along with a related increase in lanosterol (1, 15.56%), eburicol (3, 1.16%) and the fungistatic metabolite 14α-methyl ergosta-8,24(28)-diene-3β,6α-diol (4, 15.56%). From these experiments, we can conclude that our compounds inhibit ergosterol biosynthesis similarly to the azole drug control VOR.

3. Conclusions

In summary, we have synthesized novel FLC derivatives in which the triazole ring on the carbon alpha to the dihalophenyl ring of FLC was displaced by various linear alkyl-, aryl-, dialkyl-, and cycloalkyl-amino substituents. We did not detect any antifungal activity with the aryl- and cycloalkyl-amino substituted FLC analogues. We observed that the antifungal activity of the alkyl-amino FLC derivatives depends on the length of the alkyl chains. Compounds 6-9 were identified as promising antifungal agents with low hemolytic activity and low cytotoxicity. These analogues displayed great activity against some of the *C. albicans*, non-*albicans Candida*, and *Aspergillus* strains, and, in addition they were particularly excellent against the clinical strains of *C. glabrata, C. parapsilosis*, as well as *C. neoformans* tested. These compounds also exhibited superior activity against the clinical strains when compared to the control drugs CAS, FLC, and VOR. The possible mechanism of action for these FLC analogues was identified as membrane disruption with compound 8 with a $C_{12}$ alkyl chain being more membrane disrupting than compound 9 with a $C_{14}$ alkyl chain. Additionally, they were found to inhibit ergosterol biosynthesis.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Example 1 References

1. Kathiravan, M. K., Salake, A. B., Chothe, A. S., Dudhe, P. B., Watode, R. P., Mukta, M. S., and Gadhwe, S. (2012) The biology and chemistry of antifungal agents: a review, *Bioorg. Med. Chem.* 20, 5678-5698.
2. Zhang, P. Z., Zhou, S. F., Li, T. R., and Jiang, L. (2012) Efficient synthesis and in vitro antifungal activity of 1H-benzimidazol-1-yl acetates/propionates containing 1H-1,2,4-triazole moiety, *Chin. Chem. Lett.* 23, 1381-1384.
3. Jiang, Z., Wang, Y., Wang, W., Wang, S., Xu, B., Fan, G., Dong, G., Liu, Y., Yao, J., Miao, Z., Zhang, W., and Sheng, C. (2013) Discovery of highly potent triazole antifungal derivatives by heterocycle-benzene bioisosteric replacement, *Eur. J. Med. Chem.* 64, 16-22.
4. Fosso, M. Y., Shrestha, S. K., Green, K. D., and Garneau-Tsodikova, S. (2015) Synthesis and bioactivities of kanamycin B-derived cationic amphiphiles, *J. Med. Chem.* 58, 9124-9132.
5. Shrestha, S. K., Fosso, M. Y., Green, K. D., and Garneau-Tsodikova, S. (2015) Amphiphilic tobramycin analogues as antibacterial and antifungal agents, *Antimicrob. Agents Chemother.* 59, 4861-4869.
6. Ngo, H. X., Shrestha, S. K., and Garneau-Tsodikova, S. (2016) Identification of ebsulfur analogues with broad-spectrum antifungal activity, *ChemMedChem* 11, 1507-1516.
7. Ngo, H. X., Shrestha, S. K., Green, K. D., and Garneau-Tsodikova, S. (2016) Development of ebsulfur analogues as potent antibacterials against methicillin-resistant *Staphylococcus aureus, Bioorg. Med. Chem.*
8. Loeffler, J., and Stevens, D. A. (2003) Antifungal drug resistance, *Clin. Infect. Dis.* 36, S31-S41.
9. Bal, A. M. (2010) The echinocandins: three useful choices or three too many?, *Int. J. Antimicrob. Agents* 35, 13-18.
10. Correa, J. C. R., and Salgado, H. R. N. (2011) Review of fluconazole properties and analytical methods for its determination, *Crit. Rev. Anal. Chem.* 41, 124-132.
11. Kale, P., and Johnson, L. B. (2005) Second-generation azole antifungal agents, *Drugs Today* 41, 91-105.
12. Girmenia, C., and Finolezzi, E. (2011) New-generation triazole antifungal drugs: review of the Phase II and III trials, *Clin. Invest.* 1, 1577-1594.
13. Ruden, C., and Hansson, S. O. (2003) How accurate are the European Union's classifications of chemical substances, *Toxicol. Lett.* 144, 159-172.

14. Chopra, D., Mohan, T. P., Rao, K. S., and Row, T. N. G. (2004) 2-(2,4-Dichlorophenyl)-1-(1H-1,2,4-triazol-1-yl)hexan-2-ol (hexaconazole), *Acta Crystallogr. E* 60, 2410-2412.
15. Ueda, Y., Matiskella, J. D., Golik, J., Connolly, T. P., Hudyma, T. W., Venkatesh, S., Dali, M., Kang, S. H., Barbour, N., Tejwani, R., Varia, S., Knipe, J., Zheng, M., Mathew, M., Mosure, K., Clark, J., Lamb, L., Medin, I., Gao, Q., Huang, S., Chen, C. P., and Bronson, J. J. (2003) Phosphonooxymethyl prodrugs of the broad spectrum antifungal azole, ravuconazole: synthesis and biological properties, *Bioorg. Med. Chem. Lett.* 13, 3669-3672.
16. Thamban Chandrika, N., Shrestha, S. K., Ngo, H. X., and Garneau-Tsodikova, S. (2016) Synthesis and investigation of novel benzimidazole derivatives as antifungal agents, *Bioorg. Med. Chem.* 24, 3680-3686.
17. Chang, C.-W., Fosso, M., Kawasaki, Y., Shrestha, S., Bensaci, M. F., Wang, J., Evans, C. K., and Takemoto, J. Y. (2010) Antibacterial and antifungal conversion of neamine aminoglycosids through alkyl modification. Strategy for reviving old drugs into agrofungicides, *J. Antibiot.* 63, 667-672.
18. Shrestha, S. K., Fosso, M. Y., and Garneau-Tsodikova, S. (2015) A combination approach to treating fungal infections, *Sci. Rep.* 5, 17070.
19. Shrestha, S. K., Chang, C. W., Meissner, N., Oblad, J., Shrestha, J. P., Sorensen, K. N., Grilley, M. M., and Takemoto, J. Y. (2014) Antifungal amphiphilic aminoglycoside K20: bioactivities and mechanism of action, *Front. Microbiol.* 5, 671.

Example 2 References

1. Kathiravan, M. K.; Salake, A. B.; Chothe, A. S.; Dudhe, P. B.; Watode, R. P.; Mukta, M. S.; Gadhwe, S. The biology and chemistry of antifungal agents: a review. *Bioorg. Med. Chem.* 2012, 20, 5678-5698.
2. Beck-Sague, C.; Jarvis, W. R. Secular trends in the epidemiology of nosocomial fungal infections in the United States, 1980-1990. National Nosocomial Infections Surveillance System. *J. Infect. Dis.* 1993, 167, 1247-1251.
3. Pfaller, M. A.; Diekema, D. J. Epidemiology of invasive candidiasis: a persistent public health problem. *Clin. Microbiol. Rev.* 2007, 20, 133-163.
4. Pannuti, C.; Gingrich, R.; Pfaller, M. A.; Kao, C.; Wenzel, R. P. Nosocomial pneumonia in patients having bone marrow transplant. Attributable mortality and risk factors. *Cancer* 1992, 69, 2653-2662.
5. Carmona, E. M.; Limper, A. H. Overview of treatment approaches for fungal infections. *Clin. Chest Med.* 2017, 38, 393-402.
6. Wiederhold, N. P. Antifungal resistance: current trends and future strategies to combat. *Infect. Drug Resist.* 2017, 10, 249-259.
7. McCarthy, M. W.; Kontoyiannis, D. P.; Cornely, O. A.; Perfect, J. R.; Walsh, T. J. Novel agents and drug targets to meet the challenges of resistant fungi. *J. Infect. Dis.* 2017, 216, S474-S483.
8. McCarthy, M. W.; Walsh, T. J. Drug development challenges and strategies to address emerging and resistant fungal pathogens. *Expert Rev. Anti Infect. Ther.* 2017, 15, 577-584.
9. Berkow, E. L.; Lockhart, S. R. Fluconazole resistance in *Candida* species: a current perspective. *Infect. Drug Resist.* 2017, 10, 237-245.
10. Jiang, Z.; Wang, Y.; Wang, W.; Wang, S.; Xu, B.; Fan, G.; Dong, G.; Liu, Y.; Yao, J.; Miao, Z.; Zhang, W.; Sheng, C. Discovery of highly potent triazole antifungal derivatives by heterocycle-benzene bioisosteric replacement. *Eur. J. Med. Chem.* 2013, 64, 16-22.
11. Morschhauser, J. Regulation of multidrug resistance in pathogenic fungi. *Fungal Genet. Biol.* 2010, 47, 94-106.
12. Perlin, D. S.; Shor, E.; Zhao, Y. Update on antifungal drug resistance. *Curr. Clin. Microbiol. Rep.* 2015, 2, 84-95.
13. Sanglard, D. Emerging threats in antifungal-resistant fungal pathogens. *Front. Med. (Lausanne)* 2016, 3, 11.
14. Srinivasan, A.; Lopez-Ribot, J. L.; Ramasubramanian, A. K. Overcoming antifungal resistance. *Drug Discov. Today Technol.* 2014, 11, 65-71.
15. Vandeputte, P.; Ferrari, S.; Coste, A. T. Antifungal resistance and new strategies to control fungal infections. *Int. J. Microbiol.* 2012, 2012, 713687.
16. Zhou, C. H.; Wang, Y. Recent researches in triazole compounds as medicinal drugs. *Curr. Med. Chem.* 2012, 19, 239-280.
17. Zhang, L.; Peng, X. M.; Damu, G. L.; Geng, R. X.; Zhou, C. H. Comprehensive review in current developments of imidazole-based medicinal chemistry. *Med. Res. Rev.* 2014, 34, 340-437.
18. Garibotto, F. M.; Garro, A. D.; Masman, M. F.; Rodriguez, A. M.; Luiten, P. G.; Raimondi, M.; Zacchino, S. A.; Somlai, C.; Penke, B.; Enriz, R. D. New small-size peptides possessing antifungal activity. *Bioorg. Med. Chem.* 2010, 18, 158-167.
19. Menzin, J.; Meyers, J. L.; Friedman, M.; Perfect, J. R.; Langston, A. A.; Danna, R. P.; Papadopoulos, G. Mortality, length of hospitalization, and costs associated with invasive fungal infections in high-risk patients. *Am. J. Health Syst. Pharm.* 2009, 66, 1711-1717.
20. Hahn-Ast, C.; Glasmacher, A.; Muckter, S.; Schmitz, A.; Kraemer, A.; Marklein, G.; Brossart, P.; von Lilienfeld-Toal, M. Overall survival and fungal infection-related mortality in patients with invasive fungal infection and neutropenia after myelosuppressive chemotherapy in a tertiary care centre from 1995 to 2006. *J. Antimicrob. Chemother.* 2010, 65, 761-768.
21. Sheehan, D. J.; Hitchcock, C. A.; Sibley, C. M. Current and emerging azole antifungal agents. *Clin. Microbiol. Rev.* 1999, 12, 40-79.
22. Vanden Bossche, H.; Koymans, L.; Moereels, H. P450 inhibitors of use in medical treatment: focus on mechanisms of action. *Pharmacol. Ther.* 1995, 67, 79-100.
23. Emami, S.; Tavangar, P.; Keighobadi, M. An overview of azoles targeting sterol 14alpha-demethylase for anti-leishmanial therapy. *Eur. J. Med. Chem.* 2017, 135, 241-259.
24. Shrestha, S. K.; Fosso, M. Y.; Green, K. D.; Garneau-Tsodikova, S. Amphiphilic tobramycin analogues as antibacterial and antifungal agents. *Antimicrob. Agents Chemother.* 2015, 59, 4861-4869.
25. Fosso, M. Y.; Shrestha, S. K.; Green, K. D.; Garneau-Tsodikova, S. Synthesis and bioactivities of kanamycin B-derived cationic amphiphiles. *J. Med. Chem.* 2015, 58, 9124-9132.
26. Chandrika, N. T.; Shrestha, S. K.; Ngo, H. X.; Garneau-Tsodikova, S. Synthesis and investigation of novel benzimidazole derivatives as antifungal agents. *Bioorg. Med. Chem.* 2016, 24, 3680-3686.

27. Ngo, H. X.; Shrestha, S. K.; Garneau-Tsodikova, S. Identification of ebsulfur analogues with broad-spectrum antifungal activity. *ChemMedChem* 2016, 11, 1507-1516.
28. Shrestha, S. K.; Garzan, A.; Garneau-Tsodikova, S. Novel alkylated azoles as potent antifungals. *Eur. J. Med. Chem.* 2017, 133, 309-318.
29. Shrestha, S.; Grilley, M.; Fosso, M. Y.; Chang, C. W.; Takemoto, J. Y. Membrane lipid-modulated mechanism of action and non-cytotoxicity of novel fungicide aminoglycoside FG08. *PLoS One* 2013, 8, e73843.
30. Chang, C. W.; Fosso, M.; Kawasaki, Y.; Shrestha, S.; Bensaci, M. F.; Wang, J.; Evans, C. K.; Takemoto, J. Y. Antibacterial to antifungal conversion of neamine aminoglycosides through alkyl modification. Strategy for reviving old drugs into agrofungicides. *J. Antibiot.* 2010, 63, 667-672.
31. Bladocha, M.; Benveniste, P. Manipulation by tridemorph, a systemic fungicide, of the sterol composition of maize leaves and roots. *Plant Physiol.* 1983, 71, 756-762.
32. Pore, V. S.; Agalave, S. G.; Singh, P.; Shukla, P. K.; Kumar, V.; Siddiqi, M. I. Design and synthesis of new fluconazole analogues. *Org. Biomol. Chem.* 2015, 13, 6551-6561.
33. Hawser, S. P.; Douglas, L. J. Resistance of *Candida albicans* biofilms to antifungal agents in vitro. *Antimicrob. Agents Chemother.* 1995, 39, 2128-2131.
34. Hargrove, T. Y.; Wawrzak, Z.; Lamb, D. C.; Guengerich, F. P.; Lepesheva, G. I. Structure-functional characterization of cytochrome P450 sterol 14alpha-demethylase (CYP51B) from *Aspergillus fumigatus* and molecular basis for the development of antifungal drugs. *J. Biol. Chem.* 2015, 290, 23916-23934.
35. Clinical and Laboratory Standards Institute. Reference method for broth dilution antifungal susceptibility testing of yeasts—Approved standard. CLSI document M27-A3. Wayne, P A. 2008.
36. Clinical and Laboratory Standards Institute. Reference method for broth dilution antifungal susceptibility testing of filamentous fungi—$2^{nd}$ Edition: CLSI document M38-A2. Wayne, P A. 2008.
37. Shrestha, S. K.; Fosso, M. Y.; Garneau-Tsodikova, S. A combination approach to treating fungal infections. *Sci. Rep.* 2015, 5, 17070.
38. Pierce, C. G.; Uppuluri, P.; Tristan, A. R.; Wormley, F. L., Jr.; Mowat, E.; Ramage, G.; Lopez-Ribot, J. L. A simple and reproducible 96-well plate-based method for the formation of fungal biofilms and its application to antifungal susceptibility testing. *Nat. Protoc.* 2008, 3, 1494-1500.
39. Oliveira, A. S.; Martinex-de-Oliveira, J.; Palmeira-de-Oliveira, R.; Palmeira-de-Oliveira, A. Antifungal activity of antidepressant sertraline against *Candida* species in vitro: A potential beneficial association with fluconazole. *Med. J. Obstet. Gynecol.* 2017, 5, 1095.
40. Emsley, P.; Cowtan, K. Coot: model-building tools for molecular graphics. *Acta Crystallogr. D* 2004, 60, 2126-2132.

Example 3 References

1. Garibotto, F. M.; Garro, A. D.; Masman, M. F.; Rodriguez, A. M.; Luiten, P. G.; Raimondi, M.; Zacchino, S. A.; Somlai, C.; Penke, B.; Enriz, R. D. New small-size peptides possessing antifungal activity. *Bioorg. Med. Chem.* 2010, 18, 158-167.
2. Beck-Sague, C.; Jarvis, W. R. Secular trends in the epidemiology of nosocomial fungal infections in the United States, 1980-1990. National Nosocomial Infections Surveillance System. *J. Infect. Dis.* 1993, 167, 1247-1251.
3. Pfaller, M. A.; Diekema, D. J. Epidemiology of invasive candidiasis: a persistent public health problem. *Clin. Microbiol. Rev.* 2007, 20, 133-163.
4. Pannuti, C.; Gingrich, R.; Pfaller, M. A.; Kao, C.; Wenzel, R. P. Nosocomial pneumonia in patients having bone marrow transplant. Attributable mortality and risk factors. *Cancer* 1992, 69, 2653-2662.
5. Latge, J. P. *Aspergillus fumigatus* and aspergillosis. *Clin. Microbiol. Rev.* 1999, 12, 310-350.
6. Steenbergen, J. N.; Casadevall, A. Prevalence of *Cryptococcus neoformans* var. *neoformans* (Serotype D) and *Cryptococcus neoformans* var. *grubii* (Serotype A) isolates in New York City. *J. Clin. Microbiol.* 2000, 38, 1974-1976.
7. Groll, A. H.; Walsh, T. J. Uncommon opportunistic fungi: new nosocomial threats. *Clin. Microbiol. Infect.* 2001, 7 Suppl 2, 8-24.
8. Wald, A.; Leisenring, W.; van Burik, J. A.; Bowden, R. A. Epidemiology of *Aspergillus* infections in a large cohort of patients undergoing bone marrow transplantation. *J. Infect. Dis.* 1997, 175, 1459-1466.
9. Viscoli, C.; Girmenia, C.; Marinus, A.; Collette, L.; Martino, P.; Vandercam, B.; Doyen, C.; Lebeau, B.; Spence, D.; Krcmery, V.; De Pauw, B.; Meunier, F. Candidemia in cancer patients: a prospective, multicenter surveillance study by the Invasive Fungal Infection Group (IFIG) of the European Organization for Research and Treatment of Cancer (EORTC). *Clin. Infect. Dis.* 1999, 28, 1071-1079.
10. Miceli, M. H.; Diaz, J. A.; Lee, S. A. Emerging opportunistic yeast infections. *Lancet Infect. Dis.* 2011, 11, 142-151.
11. Pfaller, M. A.; Diekema, D. J.; Gibbs, D. L.; Newell, V. A.; Ellis, D.; Tullio, V.; Rodloff, A.; Fu, W.; Ling, T. A.; Global Antifungal Surveillance, G. Results from the ARTEMIS DISK Global Antifungal Surveillance Study, 1997 to 2007: a 10.5-year analysis of susceptibilities of *Candida* Species to fluconazole and voriconazole as determined by CLSI standardized disk diffusion. *J. Clin. Microbiol.* 2010, 48, 1366-1377.
12. Puig-Asensio, M.; Peman, J.; Zaragoza, R.; Garnacho-Montero, J.; Martin-Mazuelos, E.; Cuenca-Estrella, M.; Almirante, B.; Prospective Population Study on Candidemia in Spain, P.; Hospital Infection Study, G.; Medical Mycology Study Group of the Spanish Society of Infectious, D.; Clinical, M.; Spanish Network for Research in Infectious, D. Impact of therapeutic strategies on the prognosis of candidemia in the ICU. *Crit. Care Med.* 2014, 42, 1423-1432.
13. Guo, F.; Yang, Y.; Kang, Y.; Zang, B.; Cui, W.; Qin, B.; Qin, Y.; Fang, Q.; Qin, T.; Jiang, D.; Li, W.; Gu, Q.; Zhao, H.; Liu, D.; Guan, X.; Li, J.; Ma, X.; Yu, K.; Chan, D.; Yan, J.; Tang, Y.; Liu, W.; Li, R.; Qiu, H.; China, S. T. Invasive candidiasis in intensive care units in China: a multicentre prospective observational study. *J. Antimicrob. Chemother.* 2013, 68, 1660-1668.
14. Pfaller, M. A.; Diekema, D. J. Epidemiology of invasive mycoses in North America. *Crit. Rev. Microbiol.* 2010, 36, 1-53.
15. Chen, S.; Slavin, M.; Nguyen, Q.; Marriott, D.; Playford, E. G.; Ellis, D.; Sorrell, T.; Australian Candidemia, S. Active surveillance for candidemia, Australia. *Emerg. Infect. Dis.* 2006, 12, 1508-1516.
16. Wang, H.; Xiao, M.; Chen, S. C.; Kong, F.; Sun, Z. Y.; Liao, K.; Lu, J.; Shao, H. F.; Yan, Y.; Fan, H.; Hu, Z. D.; Chu, Y. Z.; Hu, T. S.; Ni, Y. X.; Zou, G. L.; Xu, Y. C. In vitro susceptibilities of yeast species to fluconazole and voriconazole as determined by the 2010 National China Hospital Invasive Fungal Surveillance Net (CHIF-NET) study. *J. Clin. Microbiol.* 2012, 50, 3952-3959.
17. Nucci, M.; Queiroz-Telles, F.; Tobon, A. M.; Restrepo, A.; Colombo, A. L. Epidemiology of opportunistic fungal infections in Latin America. *Clin. Infect. Dis.* 2010, 51, 561-570.
18. Xiao, M.; Fan, X.; Chen, S. C.; Wang, H.; Sun, Z. Y.; Liao, K.; Chen, S. L.; Yan, Y.; Kang, M.; Hu, Z. D.; Chu, Y. Z.; Hu, T. S.; Ni, Y. X.; Zou, G. L.; Kong, F.; Xu, Y. C. Antifungal susceptibilities of *Candida glabrata* species complex, *Candida krusei*, *Candida parapsilosis* species complex and *Candida tropicalis* causing invasive candidiasis in China: 3 year national surveillance. *J. Antimicrob. Chemother.* 2015, 70, 802-810.
19. Pore, V. S.; Aher, N. G.; Kumar, M.; Shukla, P. K. Design and synthesis of fluconazole/bile acid conjugate using click reaction. *Tetrahedron* 2006, 62, 11178-11186.
20. Whaley, S. G.; Berkow, E. L.; Rybak, J. M.; Nishimoto, A. T.; Barker, K. S.; Rogers, P. D. Azole antifungal resistance in *Candida albicans* and emerging non-*albicans Candida* species. *Front. Microbiol.* 2016, 7, 2173.
21. Shrestha, S. K.; Fosso, M. Y.; Green, K. D.; Garneau-Tsodikova, S. Amphiphilic tobramycin analogues as antibacterial and antifungal agents. *Antimicrob. Agents Chemother.* 2015, 59, 4861-4869.
22. Fosso, M. Y.; Shrestha, S. K.; Green, K. D.; Garneau-Tsodikova, S. Synthesis and bioactivities of kanamycin B-derived cationic amphiphiles. *J. Med. Chem.* 2015, 58, 9124-9132.
23. Thamban Chandrika, N.; Shrestha, S. K.; Ngo, H. X.; Garneau-Tsodikova, S. Synthesis and investigation of novel benzimidazole derivatives as antifungal agents. *Bioorg. Med. Chem.* 2016, 24, 3680-3686.
24. Ngo, H. X.; Shrestha, S. K.; Garneau-Tsodikova, S. Identification of ebsulfur analogues with broad-spectrum antifungal activity. *ChemMedChem* 2016, 11, 1507-1516.
25. Shrestha, S. K.; Garzan, A.; Garneau-Tsodikova, S. Novel alkylated azoles as potent antifungals. *Eur. J. Med. Chem.* 2017, 133, 309-318.
26. Chang, C. W.; Fosso, M.; Kawasaki, Y.; Shrestha, S.; Bensaci, M. F.; Wang, J.; Evans, C. K.; Takemoto, J. Y. Antibacterial to antifungal conversion of neamine aminoglycosides through alkyl modification. Strategy for reviving old drugs into agrofungicides. *J. Antibiot.* 2010, 63, 667-672.
27. Shrestha, S.; Grilley, M.; Fosso, M. Y.; Chang, C. W.; Takemoto, J. Y. Membrane lipid-modulated mechanism of action and non-cytotoxicity of novel fungicide aminoglycoside FG08. *PLoS One* 2013, 8, e73843.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound of the formula:

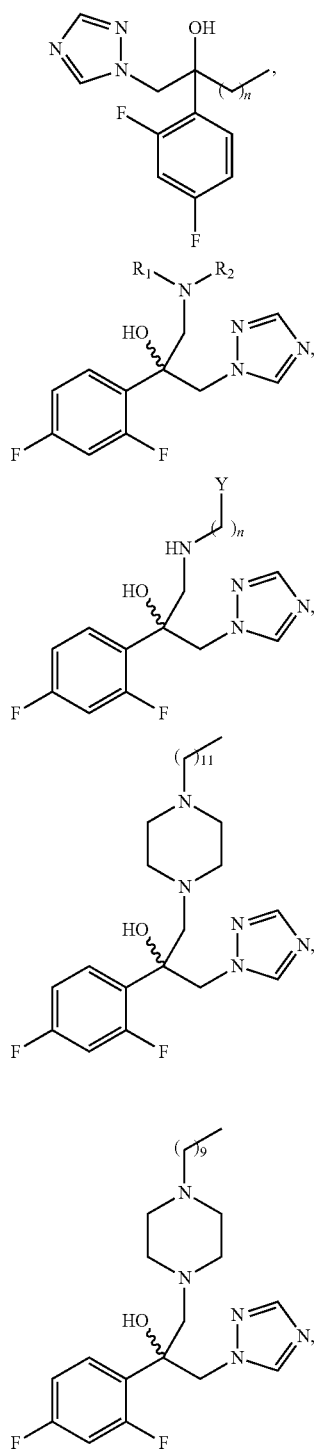

-continued

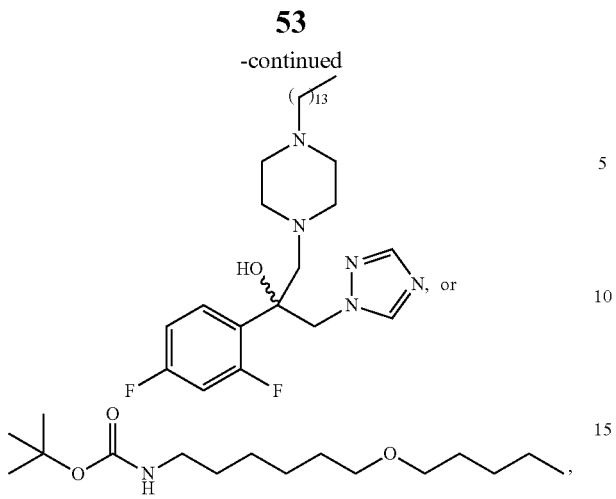

wherein $n_1$ is 6-11;

wherein $R_1$ and $R_2$ are n-hexyl, $R_1$ and $R_2$ are n-octyl, $R_1$ is cyclooctyl and $R_2$ is H, or $R_1$ is p-iPrPh and $R_2$ is H; and wherein $n_3$ is 9, 11, 13, or 15 when Y is Me, or $n_3$ is 6 when Y is OH or —O(CH$_2$)$_4$CH$_3$.

2. A pharmaceutical composition comprising the compound of claim 1, and a suitable pharmaceutical carrier.

3. The compound of claim 1, having the formula:

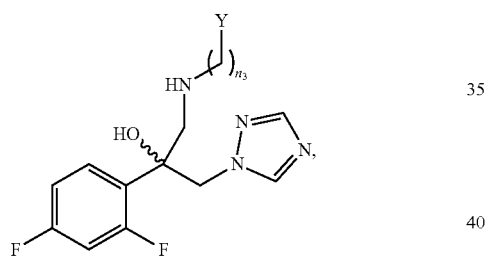

wherein Y is Me and $n_3$ is 9, 11, or 13.

4. A method of treating a fungal infection in a subject, comprising administering to the subject an effective amount of a compound of the formula:

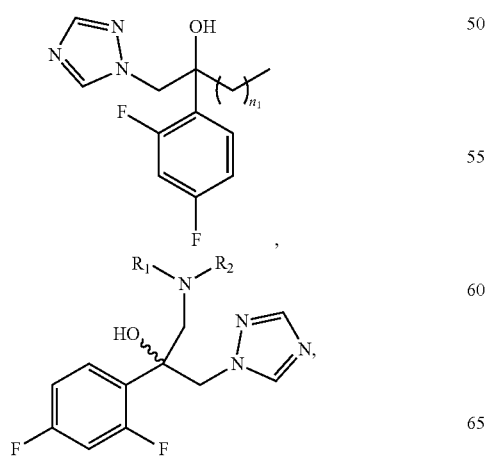

-continued

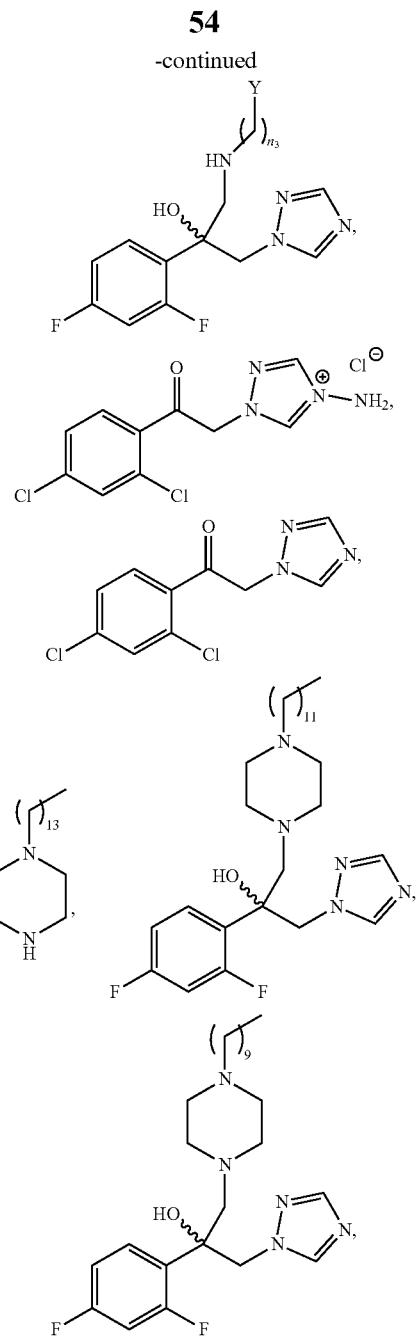

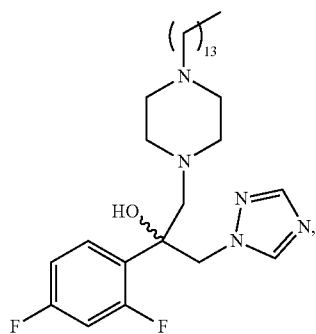

-continued

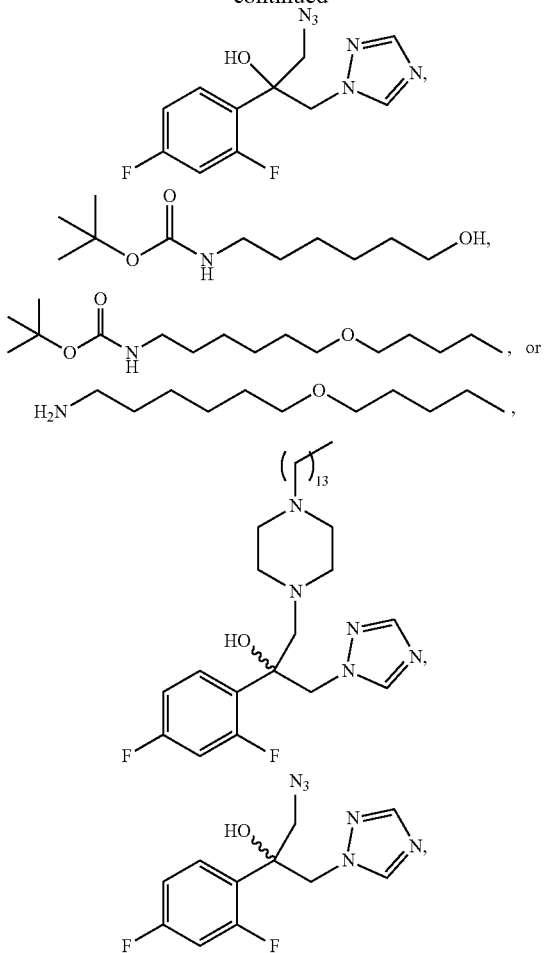

-continued

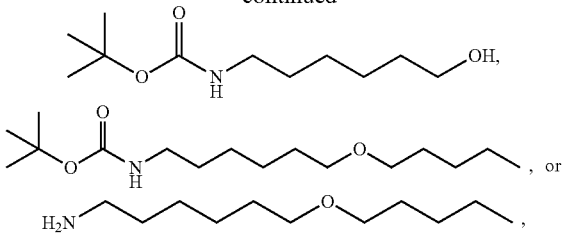

wherein $n_1$ is 6-11;
wherein $R_1$ and $R_2$ are n-hexyl, $R_1$ and $R_2$ are n-octyl, $R_1$ is cyclooctyl and $R_2$ is H, or $R_1$ is p-iPrPh and $R_2$ is H; and
wherein $n_3$ is 9, 11, 13, or 15 when Y is Me, or $n_3$ is 6 when Y is OH or —O(CH$_2$)$_4$CH$_3$.

5. The method of claim 4, wherein the subject is a human subject.

6. The method of claim 4, wherein the subject is a plant or crop.

7. The method of claim 4, wherein the compound is of the formula

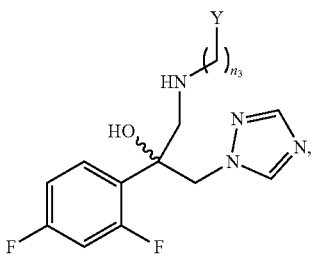

wherein Y is Me and $n_3$ is 7, 9, 11, or 13.

* * * * *